(12) United States Patent
Slassi et al.

(10) Patent No.: US 7,816,354 B2
(45) Date of Patent: Oct. 19, 2010

(54) OXAZOLIDINONE COMPOUNDS AND THEIR USE AS METABOTROPIC GLUTAMATE RECEPTOR POTENTIATORS

(75) Inventors: Abdelmalik Slassi, Toronto (CA); Methvin Isaac, Toronto (CA); Ian Egle, Toronto (CA); Fupeng Ma, Toronto (CA); Babu Joseph, Toronto (CA); Joshua Clayton, Toronto (CA); Krzysztof Swierczek, West Jordan, UT (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 11/634,250

(22) Filed: Dec. 6, 2006

(65) Prior Publication Data

US 2007/0275966 A1    Nov. 29, 2007

Related U.S. Application Data

(60) Provisional application No. 60/750,347, filed on Dec. 15, 2005.

(51) Int. Cl.
*A61K 31/421*    (2006.01)
*A61K 31/497*    (2006.01)
*C07D 239/02*    (2006.01)
*C07D 413/02*    (2006.01)

(52) U.S. Cl. ............... 514/235.8; 514/236.8; 514/376; 514/253.1; 514/254.02; 514/274; 514/340; 544/124; 544/138; 544/316; 544/364; 544/369; 546/271.1; 548/229

(58) Field of Classification Search ............... 514/376; 548/229
See application file for complete search history.

(56) References Cited

U.S. PATENT DOCUMENTS

| | | | |
|---|---|---|---|
| 4,186,126 A | 1/1980 | Messick | |
| 5,106,867 A | 4/1992 | Bloom et al. | |
| 5,410,081 A | 4/1995 | Konde et al. | |
| 5,420,291 A | 5/1995 | Cain et al. | |
| 5,461,163 A | 10/1995 | Bellon et al. | |
| 5,482,971 A | 1/1996 | Epstein et al. | |
| 5,491,134 A | 2/1996 | Sher et al. | |
| 5,574,030 A | 11/1996 | Masaki et al. | |
| 5,663,360 A * | 9/1997 | Bortolaso et al. | 548/229 |
| 5,688,785 A | 11/1997 | Vaccaro | |
| 5,965,607 A | 10/1999 | Venkatesan | |
| 6,117,895 A | 9/2000 | Wachtel et al. | |
| 2004/0220244 A1 | 11/2004 | Takagi et al. | |
| 2005/0197361 A1 | 9/2005 | Jirgensons | |
| 2006/0040999 A1 * | 2/2006 | Ali et al. | 514/376 |

FOREIGN PATENT DOCUMENTS

| DE | 153 682 A1 | 1/1982 |
|---|---|---|
| EP | 0 294 995 A1 | 12/1988 |
| EP | 0 455 006 A2 | 11/1991 |
| EP | 0 579 169 A1 | 1/1994 |
| EP | 0 657 439 A1 | 6/1995 |
| EP | 0 659 737 A2 | 6/1995 |
| EP | 1 236 723 A | 9/2002 |
| EP | 1 435 353 A1 | 7/2004 |
| JP | 9-268171 A | 10/1997 |
| JP | 10-036359 A | 2/1998 |
| JP | 11-035534 A | 2/1999 |
| WO | WO-86/02268 A1 | 4/1986 |
| WO | WO-95/28926 A1 | 11/1995 |
| WO | WO-98/29405 A | 7/1998 |
| WO | WO-99/59586 A | 11/1999 |
| WO | WO-00/40560 A | 7/2000 |
| WO | WO-02/094770 A | 11/2002 |
| WO | WO-2004-056814 A | 7/2004 |
| WO | WO-2006-014357 A | 2/2006 |
| WO | WO 2006014357 A1 * | 2/2006 |
| WO | WO-2006/090792 A | 8/2006 |

OTHER PUBLICATIONS

Schoepp et al., Trends Pharmacol. Sci. 14:13 (1993).
Schoepp, Neurochem. Int. 24:439 (1994).
Pin et al., Neuropharmacology 34:1 (1995).
Bordi and Ugolini, Pro. Neurobiol. 59:55 (1999).
Nakanishi, Neuron 13:1031 (1994).
Knopfel et al., J. Med. Chem. 38:1417 (1995).
Bashir et al., Nature 363:347 (1993).
Bortolotto et al., Nature 368:740 (1994).
Aiba et al., Cell 79:365 (1994).
Aiba et al., Cell 79:377 (1994).
Meller et al., Neuroreport 4:879 (1993).
Bordi and Ugolini, Brainb Res. 871:223 (2000).
Pin et al., Eur. J. Pharmacol. vol. 375, p. 277-294 (1999).
Monge et al., J. Heterocyclic Chem., vol. 32, p. 1429 (1995).

(Continued)

*Primary Examiner*—Yong Chu
(74) *Attorney, Agent, or Firm*—Kenneth F. Mitchell

(57) ABSTRACT

The present invention is directed to compounds of Formula I:

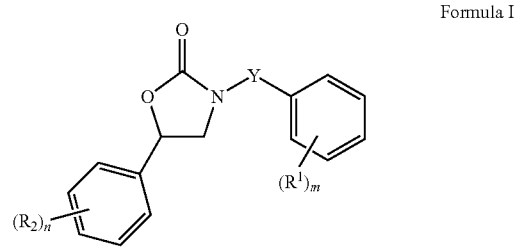

Formula I

Wherein $R^1$, $R^2$, Y, m and n are further defined in the description. The invention also relates to processes for the preparation of the compounds and to new intermediates employed in the preparation, pharmaceutical compositions containing the compounds, and to the use of the compounds in therapy.

6 Claims, No Drawings

OTHER PUBLICATIONS

Mieczkowski, Bulletin of the Polish Academy of Sciences, vol. 34, p. 109 (1986).
Das, Synthetic Communications, vol. 18, p. 907 (1988).
Tiecco et al., Chemistry—a European Journal, vol. 10, p. 1752 (2004).
Sugiyama et al., Heterocycles, vol. 57, p. 637 (2002).
Hancock et al., Tetrahedron Letters, vol. 44, p. 5457 (2003).
Hancock et al., Synthesis, vol. 14, p. 2347 (2004).
Dow et al.; Bioorganic & Medicinal Chemistry Letters, 14:12, p. 3235-3240, 2004; XP002434583.
Tiecco et al., Chemistry—A European Journal, 10:7, pp. 1752-1764, 2004, XP002434582.
Hancock et al., Tetrahedron Letters, 44:29, pp. 5457-5460, 2003, XP002434584.
Sugiyama et al., Heterocycles, 57:4, pp. 637-648, 2002, XP002434585.
Sher et al., Bioorganic & Medicinal Chemistry Letters, 7:12, pp. 1583-1588, 1997, XP002434586.
Monge et al., Journal of Heterocyclic Chemistry, 32:5, pp. 1429-1439, 1995, XP 002434587.
Bloom et al., Journal of Medicinal Chemistry, 35:16, pp. 3081-3084, 1992, XP002434588.
Das, Synthetic Communications, 18:9, pp. 907-915, 1988, XP002434589.
Mieczkowski, Bulletin of the Polish Academy of Sciences, Chemistry, 34:3-4, pp. 109-113, 1987, XP002434590.
Tsuge et al., Nippon Kagaku Zasshi, 90:10, pp. 1031-1035, 1970, XP002434591.
Burkhardt et al., Chemische Berichte, 99:6, pp. 1912-1917, 1966, XP002434592.
Gulbins et al., Chemische Berichte, 93, pp. 1975-1982, 1961, XP002434593.
Hara et al., Meijo Daigaku Sogo Kenkyusho Kiyo, 11, pp. 147-150, 2006, XP002434596.
Wrobel et al., Polish Journal of Chemistry, 80:6, pp. 907-912, 2006, XP002434597.
Siriwardana et al., Heterocycles, 66, pp. 333-339, 2006, XP002434598.

* cited by examiner

OXAZOLIDINONE COMPOUNDS AND THEIR USE AS METABOTROPIC GLUTAMATE RECEPTOR POTENTIATORS

This Non-provisional application claims priority under 35 U.S.C. §119(e) on U.S. Provisional Application No. 60/750,347 filed on Dec. 15, 2005, the entire contents of which are hereby incorporated by reference.

BACKGROUND OF THE INVENTION

The present invention relates to novel compounds which are potentiators of glutamate receptors, methods for their preparation, pharmaceutical compositions containing them and their use in therapy.

The metabotropic glutamate receptors (mGluR) constitute a family of GTP-binding-protein (G-protein) coupled receptors that are activated by glutamate, and have important roles in synaptic activity in the central nervous system, including neural plasticity, neural development and neurodegeneration.

Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels (Schoepp et al., 1993, Trends Pharmacol. Sci., 14:13; Schoepp, 1994, Neurochem. Int., 24:439; Pin et al., 1995, Neuropharmacology 34:1; Bordi & Ugolini, 1999, Prog. Neurobiol. 59:55).

Eight mGluR subtypes have been identified, which are divided into three groups based upon primary sequence similarity, signal transduction linkages, and pharmacological profile. Group-I includes mGluR1 and mGluR5, which activate phospholipase C and the generation of an intracellular calcium signal. The Group-II (mGluR2 and mGluR3) and Group-III (mGluR4, mGluR6, mGluR7, and mGluR8) mGluR5 mediate an inhibition of adenylyl cyclase activity and cyclic AMP levels. For a review, see Pin et al., 1999, Eur. J. Pharmacol., 375:277-294.

Members of the mGluR family of receptors are implicated in a number of normal processes in the mammalian CNS, and are important targets for compounds for the treatment of a variety of neurological and psychiatric disorders. Activation of mGluRs is required for induction of hippocampal long-term potentiation and cerebellar long-term depression (Bashir et al., 1993, Nature, 363:347; Bortolotto et al., 1994, Nature, 368:740; Aiba et al., 1994, Cell, 79:365; Aiba et al., 1994, Cell, 79:377). A role for mGluR activation in nociception and analgesia also has been demonstrated (Meller et al., 1993, Neuroreport, 4: 879; Bordi & Ugolini, 1999, Brain Res., 871:223). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex (Nakanishi, 1994, Neuron, 13:1031; Pin et al., 1995, Neuropharmacology, supra; Knopfel et al., 1995, J. Med. Chem., 38:1417).

Recent advances in the elucidation of the neurophysiological roles of mGluRs have established these receptors as promising drug targets in the therapy of acute and chronic neurological and psychiatric disorders and chronic and acute pain disorders. Because of the physiological and pathophysiological significance of the mGluRs, there is a need for new drugs and compounds that can modulate mGluR function.

SUMMARY OF THE INVENTION

The invention satisfies this need and others by providing, as one object, compounds of Formula I,

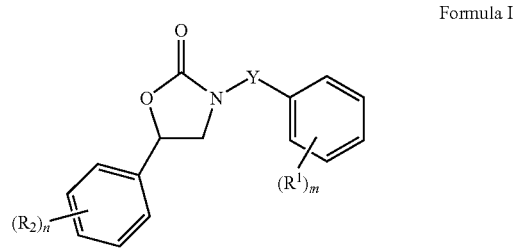

Formula I wherein:
$R^1$ is selected from the group consisting of H, hydroxy, F, Cl, Br, I, nitro, CN, alkyl, alkylhalo, O-alkyl, O-alkylhalo, alkenyl, O-alkenyl, alkynyl, O-alkynyl, cycloalkyl, alkylene-cycloalkyl, O-cycloalkyl, O-alkylene-cycloalkyl, heterocycloalkyl, alkylene-heterocycloalkyl, O-heterocycloalkyl, O-alkylene-heterocycloalkyl, aryl, alkylenearyl, O-aryl, O-alkylenearyl, heteroaryl, alkyleneheteroaryl, O-heteroaryl, O-alkyleneheteroaryl, (CO)cycloalkyl, (CO)heterocycloalkyl, (CO)aryl, (CO)heteroaryl, alkyleneOR$^4$, O-alkyleneOR$^4$, (CO)R$^7$, O(CO)R$^7$, alkyleneO(CO)R$^7$, alkylene(CO)R$^7$, O-alkylene(CO)R$^7$, CO$_2$R$^7$, alkyleneCO$_2$R$^7$, O-alkyleneCO$_2$R$^7$, alkylenecyano, O-alkylenecyano, NR$^4$R$^5$, alkyleneNR$^4$R$^5$, O-alkyleneNR$^4$R$^5$, (CO)NR$^4$R$^5$, alkylene(CO)NR$^4$R$^5$, O—(CO)NR$^4$R$^5$, O-alkylene(CO)NR$^4$R$^5$, NR$^4$(CO)R$^3$, alkyleneNR$^4$(CO)R$^3$, O-alkyleneNR$^4$(CO)R$^5$, NR$^4$(CO) NR$^4$R$^5$, alkyleneNR$^4$(CO)NR$^4$R$^5$, SR$^4$, alkyleneSR$^4$, O-alkyleneSR$^4$, (SO)R$^3$, alkylene(SO)R$^3$, O-alkylene(SO) R$^3$, SO$_2$R$^3$, alkyleneSO$_2$R$^3$, O-alkyleneSO$_2$R$^3$, (SO$_2$) NR$^4$R$^5$, alkylene(SO$_2$)NR$^4$R$^5$, O-alkylene(SO$_2$)NR$^4$R$^5$, NR$^4$(SO$_2$)R$^5$, alkyleneNR$^4$(SO$_2$)R$^5$, O-alkyleneNR$^4$ (SO$_2$)R$^5$, NR$^4$(SO$_2$)NR$^4$R$^5$, alkyleneNR$^4$(SO$_2$)NR$^4$R$^5$, O-alkyleneNR$^4$(SO$_2$)NR$^4$R$^5$, NR$^4$OR$^5$, NR$^4$(CO)OR$^7$, alkylNR$^4$(CO)OR$^7$, O-alkylNR$^4$(CO)OR$^7$ and any cyclic moiety is optionally substituted by one or more independently selected substituents R$^6$;

$R^2$ is selected from the group consisting of H, hydroxy, F, Cl, Br, I, CN, alkyl, alkylhalo, O-alkyl, O-alkylhalo, cycloalkyl, alkylene-cycloalkyl, O-cycloalkyl, O-alkylene-cycloalkyl, heterocycloalkyl, alkylene-heterocycloalkyl, O-heterocycloalkyl, O-alkylene-heterocycloalkyl, aryl, alkylenearyl, O-aryl, O-alkylenearyl, heteroaryl, alkyleneheteroaryl, O-heteroaryl, O-alkyleneheteroaryl, alkyleneOR$^4$, O-alkyleneOR$^4$, (CO)R$^7$, alkylene(CO)R$^7$, alkyleneNR$^4$R$^5$, O-alkyleneNR$^4$R$^5$, (CO) NR$^4$R$^5$, alkylene(CO)NR$^4$R$^5$, O-alkylene(CO)NR$^4$R$^5$, alkyleneNR$^4$(CO)R$^3$, and any cyclic moiety is optionally substituted by one or more independently selected substituents R$^6$;

$R^3$ is, in each instance, selected from the group consisting of H and alkyl, $R^4$ and $R^5$ are independently selected from the group consisting of H, alkyl, alkylhalo, alkenyl, alkynyl, cycloalkyl, alkylenecycloalkyl, heterocycloalkyl, alkyleneheterocycloalkyl, aryl, alkylenearyl, heteroaryl, and alkyleneheteroaryl, $NR^7R^8$, alkylene$NR^7R^8$, $OR^7$, alkylene$OR^7$, and any cyclic moiety is optionally substituted with a substituent selected from the group consisting of alkyl, halo, haloalkyl O-alkyl, O-haloalkyl, aryl, alkylenearyl, heteroaryl and alkyleneheteroaryl;

$R^6$ is, in each instance, selected from the group consisting of H, hydroxy, F, Cl, Br, I, nitro, CN, oxo, alkyl, alkylhalo, O-alkyl, O-alkylhalo, alkenyl, O-alkenyl, alkynyl, O-alkynyl, cycloalkyl, alkylene-cycloalkyl, O-cycloalkyl, O-alkyl-cycloalkyl, heterocycloalkyl, alkylene-heterocycloalkyl, O-heterocycloalkyl, O-alkylene-heterocycloalkyl, aryl, alkylenearyl, O-aryl, O-alkylenearyl, heteroaryl, alkyleneheteroaryl, O-heteroaryl, O-alkyleneheteroaryl, (CO)cycloalkyl, (CO)heterocycloalkyl, (CO)aryl, (CO)heteroaryl, alkylene$OR^4$, O-alkylene$OR^4$, $(CO)R^3$, $O(CO)R^3$, alkyleneO$(CO)R^3$, alkylene$(CO)R^3$, O-alkylene$(CO)R^3$, $CO_2R^4$, alkylene$CO_2R^3$, O-alkylene$CO_2R^3$, alkylenecyano, O-alkylenecyano, $NR^4R^5$, alkylene$NR^4R^5$, O-alkylene$NR^4R^5$, $(CO)NR^4R^5$, alkylene$(CO)NR^4R^5$, O—$(CO)NR^4R^5$, O-alkylene$(CO)NR^4R^5$, $NR^4(CO)R^3$, alkylene$NR^4(CO)R^3$, O-alkylene$NR^4(CO)R^3$, $NR^4(CO)NR^4R^{13}$, $SR^4$, alkylene$SR^5$, O-alkylene$SR^4$, $(SO)R^3$, alkylene$(SO)R^3$, O-alkylene$(SO)R^3$, $SO_2R^3$, alkylene$SO_2R^3$, O-alkylene$SO_2R^3$, $(SO_2)NR^4R^5$, alkylene$(SO_2)NR^4R^5$, O-alkylene$(SO_2)NR^7R^8$, $NR^7(SO_2)R^8$, alkylene$NR^7(SO_2)R^8$, O-alkylene$NR^4(SO_2)R^5$, $NR^4(CO)OR^5$, alkyl$NR^4(CO)OR^5$, O-alkyl$NR^4(CO)OR^5$, $SO_3R^4$ and any cyclic moiety is optionally substituted with a substituent selected from the group consisting of halo, alkyl, O-alkyl, haloalkyl, O-haloalkyl and $NR^4R^5$;

$R^7$ and $R^8$ are independently selected from the group consisting of H and alkyl;

Y is selected from the group consisting of alkylene, alkenylene and alkynylene wherein any hydrogen atom of Y may be independently substituted with one or more substituents selected from the group consisting of hydroxy, F, Cl, Br, I, alkyl, alkylhalo and O-alkyl; and m and n are independently selected from the group consisting of 0, 1, 2, 3 and 4;

with the proviso that the compound is not selected from the group consisting of:

3-Benzyl-5-phenyl-2-oxazolidinone,
3-(α-Methylbenzyl)-5-phenyl-2-oxazolidinone,
3-(α-Methyl-(4-methylbenzyl)-5-phenyl-2-oxazolidinone,
3-((2-Thienyl)methyl)-5-phenyl-2-oxazolidinone,
5-(3,4-Dimethoxyphenyl)-3-benzyl-2-oxazolidinone,
5-(3,4-Dimethoxyphenyl)-3-(2-(3,4-dimethoxyphenylethyl))-2-oxazolidinone,
Methyl 4[2-[5-(3-chlorophenyl)-2-oxazolidin-3-yl]propyl]phenoxy ethanoate,
4[2-[5-(3-Chlorophenyl)-2-oxazolidin-3-yl]propyl]phenoxy ethanoic acid,
3-[1-(4-Methylphenyl)ethyl]-5-phenyl-2-oxazolidinone,
5-(3-Chlorophenyl)-3-(2-(3,4-dihydroxyphenyl)-1-methylethyl)-2-oxazolidinone and
5-(3-Chlorophenyl)-3-[(3,4-dimethoxyphenyl)-butan-2-yl]-2-oxazolidinone.

Another object of the invention is to provide a pharmaceutical composition comprising a compound according to Formula I together with a pharmaceutically acceptable carrier or excipient.

Yet another object of the invention is a method for the treatment or prevention of neurological and psychiatric disorders associated with glutamate dysfunction in an animal in need of such treatment. The method comprises the step of administering to the animal a therapeutically effective amount of a compound of Formula I or a pharmaceutical composition thereof. Preferably, the animal is a mammal; more preferably a human being.

Still another object of the invention is the use of a compound according to Formula I, or a pharmaceutically acceptable salt or solvate thereof, for the manufacture of a medicament for the treatment of any of the conditions discussed herein.

Another object of the invention provides a compound of Formula I, or a pharmaceutically acceptable salt or solvate thereof, for use in therapy.

The invention additionally provides processes for the preparation of compounds of Formula I. General and specific processes are discussed in more detail below.

DETAILED DESCRIPTION OF THE PREFERRED EMBODIMENTS

The present invention is based upon the discovery of compounds that exhibit activity as pharmaceuticals, in particular as modulators of metabotropic glutamate receptors. More particularly, the compounds of the present invention exhibit activity as potentiators of the mGluR2 receptor, and are useful in therapy, in particular for the treatment of neurological and psychiatric disorders associated with glutamate dysfunction.

DEFINITIONS

Unless specified otherwise within this specification, the nomenclature used in this specification generally follows the examples and rules stated in *Nomenclature of Organic Chemistry*, Sections A, B, C, D, E, F, and H, Pergamon Press, Oxford, 1979, which is incorporated by references herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

The term "alkyl" as used herein means a straight- or branched-chain hydrocarbon radical having from one to six carbon atoms, and includes methyl, ethyl, propyl, isopropyl, t-butyl and the like.

The term "alkenyl" as used herein means a straight- or branched-chain alkenyl radical having from two to six carbon atoms, and includes ethenyl, 1-propenyl, 1-butenyl and the like.

The term "alkynyl" as used herein means a straight- or branched-chain alkynyl radical having from two to six carbon atoms, and includes 1-propynyl (propargyl), 1-butynyl and the like.

The term "cycloalkyl" as used herein means a cyclic group (which may be unsaturated) having from three to seven carbon atoms, and includes cyclopropyl, cyclohexyl, cyclohexenyl and the like.

The term "heterocycloalkyl" as used herein means a three- to seven-membered cyclic group (which may be unsaturated) having at least one heteroatom selected from the group consisting of N, S and O, and includes piperidinyl, piperazinyl, pyrrolidinyl, tetrahydrofuranyl and the like.

The term "alkoxy" as used herein means a straight- or branched-chain alkoxy radical having from one to six carbon atoms and includes methoxy, ethoxy, propyloxy, isopropyloxy, t-butoxy and the like.

The term "halo" as used herein means halogen and includes fluoro, chloro, bromo, iodo and the like, in both radioactive and non-radioactive forms.

The term "alkylene" as used herein means a difunctional branched or unbranched saturated hydrocarbon radical having one to six carbon atoms, and includes methylene, ethylene, n-propylene, n-butylene and the like.

The term "alkenylene" as used herein means a difunctional branched or unbranched hydrocarbon radical having two to six carbon atoms and having at least one double bond, and includes ethenylene, n-propenylene, n-butenylene and the like.

The term "alkynylene" as used herein means a difunctional branched or unbranched hydrocarbon radical having two to six carbon atoms and having at least one triple bond, and includes ethynylene, n-propynylene, n-butynylene and the like.

The term "aryl" as used herein means an aromatic group having five to twelve atoms, and includes phenyl, naphthyl and the like.

The term "heteroaryl" means an aromatic group which includes at least one heteroatom selected from the group consisting of N, S and O, and includes groups and includes pyridyl, indolyl, furyl, benzofuryl, thienyl, benzothienyl, quinolyl, oxazolyl and the like.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. The selection criteria for the appropriate salt will be known to one skilled in the art. Other non-pharmaceutically acceptable salts e.g. oxalates may be used for example in the isolation of compounds of Formula I for laboratory use, or for subsequent conversion to a pharmaceutically acceptable acid addition salt.

A "pharmaceutically acceptable basic addition salt" is any non-toxic organic or inorganic base addition salt of the acid compounds represented by Formula I or any of its intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

The term "solvate" means a compound of Formula I or the pharmaceutically acceptable salt of a compound of Formula I wherein molecules of a suitable solvent are incorporated into a crystal lattice. A suitable solvent is physiologically tolerable at the dosage administered as the solvate. Examples of suitable solvents are ethanol, water and the like. When water is the solvent, the molecule is referred to as a hydrate.

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

Compounds

Compounds of the invention conform generally to Formula I:

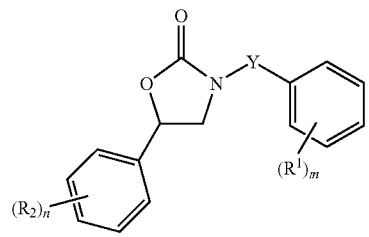

Formula I wherein:
$R^1$ is selected from the group consisting of H, hydroxy, F, Cl, Br, I, nitro, CN, alkyl, alkylhalo, O-alkyl, O-alkylhalo, alkenyl, O-alkenyl, alkynyl, O-alkynyl, cycloalkyl, alkylene-cycloalkyl, O-cycloalkyl, O-alkylene-cycloalkyl, heterocycloalkyl, alkylene-heterocycloalkyl, O-heterocycloalkyl, O-alkylene-heterocycloalkyl, aryl, alkylenearyl, O-aryl, O-alkylenearyl, heteroaryl, alkyleneheteroaryl, O-heteroaryl, O-alkyleneheteroaryl, (CO)cycloalkyl, (CO)heterocycloalkyl, (CO)aryl, (CO)heteroaryl, alkyleneOR$^4$, O-alkyleneOR$^4$, (CO)R$^7$, O(CO)R$^7$, alkyleneO(CO)R$^7$, alkylene(CO)R$^7$, O-alkylene(CO)R$^7$, CO$_2$R$^7$, alkyleneCO$_2$R$^7$, O-alkyleneCO$_2$R$^7$, alkylenecyano, O-alkylenecyano, NR$^4$R$^5$, alkyleneNR$^4$R$^5$, O-alkyleneNR$^4$R$^5$, (CO)NR$^4$R$^5$, alkylene(CO)NR$^4$R$^5$, O—(CO)NR$^4$R$^5$, O-alkylene(CO)NR$^4$R$^5$, NR$^4$(CO)R$^3$, alkyleneNR$^4$(CO)R$^3$, O-alkyleneNR$^4$(CO)R$^5$, NR$^4$(CO)NR$^4$R$^5$, alkyleneNR$^4$(CO)NR$^4$R$^5$, SR$^4$, alkyleneSR$^4$, O-alkyleneSR$^4$, (SO)R$^3$, alkylene(SO)R$^3$, O-alkylene(SO)R$^3$, SO$_2$R$^3$, alkyleneSO$_2$R$^3$, O-alkyleneSO$_2$R$^3$, (SO$_2$)NR$^4$R$^5$, alkylene(SO$_2$)NR$^4$R$^5$, O-alkylene(SO$_2$)NR$^4$R$^5$, NR$^4$(SO$_2$)R$^5$, alkyleneNR$^4$(SO$_2$)R$^5$, O-alkyleneNR$^4$(SO$_2$)R$^5$, NR$^4$(SO$_2$)NR$^4$R$^5$, alkyleneNR$^4$(SO$_2$)NR$^4$R$^5$, O-alkyleneNR$^4$(SO$_2$)NR$^4$R$^5$, NR$^4$OR$^5$, NR$^4$(CO)OR$^7$, alkylNR$^4$(CO)OR$^7$, O-alkylNR$^4$(CO)OR$^7$ and any cyclic moiety is optionally substituted by one or more independently selected substituents R$^6$;
$R^2$ is selected from the group consisting of H, hydroxy, F, Cl, Br, I, CN, alkyl, alkylhalo, O-alkyl, O-alkylhalo, cycloalkyl, alkylene-cycloalkyl, O-cycloalkyl, O-alkylene-cycloalkyl, heterocycloalkyl, alkylene-heterocycloalkyl, O-heterocycloalkyl, O-alkylene-heterocycloalkyl, aryl, alkylenearyl, O-aryl, O-alkylenearyl, heteroaryl, alkyleneheteroaryl, O-heteroaryl, O-alkyleneheteroaryl, alkyleneOR$^4$, O-alkyleneOR$^4$, (CO)R$^7$, alkylene(CO)R$^7$, alkyleneNR$^4$R$^5$, O-alkyleneNR$^4$R$^5$, (CO)NR$^4$R$^5$, alkylene(CO)NR$^4$R$^5$, O-alkylene(CO)NR$^4$R$^5$, alkyleneNR$^4$(CO)R$^3$, and any cyclic moiety is optionally substituted by one or more independently selected substituents R$^6$;

R$^3$ is, in each instance, selected from the group consisting of H and alkyl,

R$^4$ and R$^5$ are independently selected from the group consisting of H, alkyl, alkylhalo, alkenyl, alkynyl, cycloalkyl, alkylenecycloalkyl, heterocycloalkyl, alkyleneheterocycloalkyl, aryl, alkylenearyl, heteroaryl, and alkyleneheteroaryl, NR$^7$R$^8$, alkyleneNR$^7$R$^8$, OR$^7$, alkyleneOR$^7$, and any cyclic moiety is optionally substituted with a substituent selected from the group consisting of alkyl, halo, haloalkyl O-alkyl, O-haloalkyl, aryl, alkylenearyl, heteroaryl and alkyleneheteroaryl;

R$^6$ is, in each instance, selected from the group consisting of H, hydroxy, F, Cl, Br, I, nitro, CN, oxo, alkyl, alkylhalo, O-alkyl, O-alkylhalo, alkenyl, O-alkenyl, alkynyl, O-alkynyl, cycloalkyl, alkylene-cycloalkyl, O-cycloalkyl, O-alkyl-cycloalkyl, heterocycloalkyl, alkylene-heterocycloalkyl, O-heterocycloalkyl, O-alkylene-heterocycloalkyl, aryl, alkylenearyl, O-aryl, O-alkylenearyl, heteroaryl, alkyleneheteroaryl, O-heteroaryl, O-alkyleneheteroaryl, (CO)cycloalkyl, (CO)heterocycloalkyl, (CO)aryl, (CO)heteroaryl, alkyleneOR$^4$, O-alkyleneOR$^4$, (CO)R$^3$, O(CO)R$^3$, alkyleneO(CO)R$^3$, alkylene(CO)R$^3$, O-alkylene(CO)R$^3$, CO$_2$R$^4$, alkyleneCO$_2$R$^3$, O-alkyleneCO$_2$R$^3$, alkylenecyano, O-alkylenecyano, NR$^4$R$^5$, alkyleneNR$^4$R$^5$, O-alkyleneNR$^4$R$^5$, (CO)NR$^4$R$^5$, alkylene(CO)NR$^4$R$^5$, O—(CO)NR$^4$R$^5$, O-alkylene(CO)NR$^4$R$^5$, NR$^4$(CO)R$^3$, alkyleneNR$^4$(CO)R$^3$, O-alkyleneNR$^4$(CO)R$^3$, NR$^4$(CO)NR$^4$R$^{13}$, SR$^4$, alkyleneSR$^5$, O-alkyleneSR$^4$, (SO)R$^3$, alkylene(SO)R$^3$, O-alkylene(SO)R$^3$, SO$_2$R$^3$, alkyleneSO$_2$R$^3$, O-alkyleneSO$_2$R$^3$, (SO$_2$)NR$^4$R$^5$, alkylene(SO$_2$)NR$^4$R$^5$, O-alkylene(SO$_2$)NR$^7$R$^8$, NR$^7$(SO$_2$)R$^8$, alkyleneNR$^7$(SO$_2$)R$^8$, O-alkyleneNR$^4$(SO$_2$)R$^5$, NR$^4$(CO)OR$^5$, alkylNR$^4$(CO)OR$^5$, O-alkylNR$^4$(CO)OR$^5$, SO$_3$R$^4$ and any cyclic moiety is optionally substituted with a substituent selected from the group consisting of halo, alkyl, O-alkyl, haloalkyl, O-haloalkyl and NR$^4$R$^5$;

R$^7$ and R$^8$ are independently selected from the group consisting of H and alkyl;

Y is selected from the group consisting of alkylene, alkenylene and alkynylene wherein any hydrogen atom of Y may be independently substituted with one or more substituents selected from the group consisting of hydroxy, F, Cl, Br, I, alkyl, alkylhalo and O-alkyl; and m and n are independently selected from the group consisting of 0, 1, 2, 3 and 4;

with the proviso that the compound is not selected from the group consisting of:

3-Benzyl-5-phenyl-2-oxazolidinone,
3-(α-Methylbenzyl)-5-phenyl-2-oxazolidinone,
3-(α-Methyl-(4-methylbenzyl))-5-phenyl-2-oxazolidinone,
3-((2-Thienyl)methyl)-5-phenyl-2-oxazolidinone,
5-(3,4-Dimethoxyphenyl)-3-benzyl-2-oxazolidinone,
5-(3,4-Dimethoxyphenyl)-3-(2-(3,4-dimethoxyphenyl))-2-oxazolidinone,
Methyl 4[2-[5-(3-chlorophenyl)-2-oxazolidin-3-yl]propyl] phenoxy ethanoate,
4[2-[5-(3-Chlorophenyl)-2-oxazolidin-3-yl]propyl] phenoxy ethanoic acid,
3-[1-(4-Methylphenyl)ethyl]-5-phenyl-2-oxazolidinone,
5-(3-Chlorophenyl)-3-(2-(3,4-dihydroxyphenyl)-1-methylethyl)-2-oxazolidinone and
5-(3-Chlorophenyl)-3-[(3,4-dimethoxyphenyl)-butan-2-yl]-2-oxazolidinone.

In one embodiment Y is a CH$_2$ group.

In another embodiment R$^2$ is selected from the group consisting of alkyl, alkoxy, trifluoromethoxy and halo. In other embodiments R$^2$ is a 4-halo group; in yet another it is a 4-chloro group.

In still other embodiments R$^1$ is selected from the group consisting of optionally-substituted aryl, O-aryl, heteroaryl and O-heteroaryl groups. In another embodiment R$^1$ is an optionally-substituted phenyl group, in another it is an optionally-substituted O-pyridyl group.

In other embodiments R$^1$ is an aryl group further substituted with a substituent selected from the group consisting of alkyleneNR$_4$R$_5$, (CO)NR$_4$R$_5$ and O-alkyleneNR$_4$R$_5$.

It will be understood by those of skill in the art that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be appreciated by those of skill in the art that certain compounds of the present invention may exist as geometrical isomers, for example E and Z isomers of alkenes. The present invention includes any geometrical isomer of a compound of Formula I. It will further be understood that the present invention encompasses tautomers of the compounds of Formula I.

It will also be understood by those of skill in the art that certain compounds of the present invention may exist in solvated, for example hydrated, as well as unsolvated forms. It will further be understood that the present invention encompasses all such solvated forms of the compounds of Formula I.

Within the scope of the invention are also salts of the compounds of Formula I. Generally, pharmaceutically acceptable salts of compounds of the present invention are obtained using standard procedures well known in the art, for example, by reacting a sufficiently basic compound, for example an alkyl amine with a suitable acid, for example, HCl or acetic acid, to afford a physiologically acceptable anion. It is also possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment of the present invention, the compound of Formula I may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

Specific examples of the present invention include the compounds 1 to 125 as illustrated in the following table, their pharmaceutically acceptable salts, hydrates, solvates, optical isomers, and combinations thereof:

| No. | Structure | Name |
|---|---|---|
| 1 | 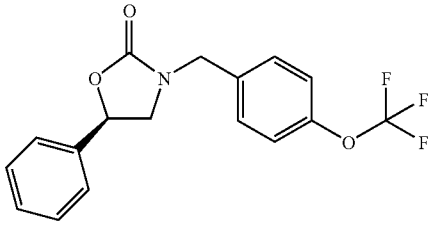 | 5-(R)-Phenyl-3-(4-trifluoromethoxybenzyl)-oxazolidin-2-one |
| 2 | 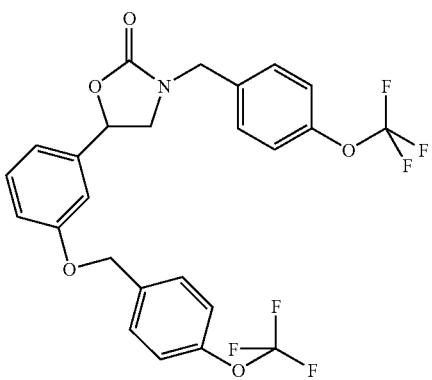 | 3-(4-Trifluoromethoxybenzyl)-5-[3-(4-trifluoromethoxybenzyloxy) phenyl]-oxazolidin-2-one |
| 3 | 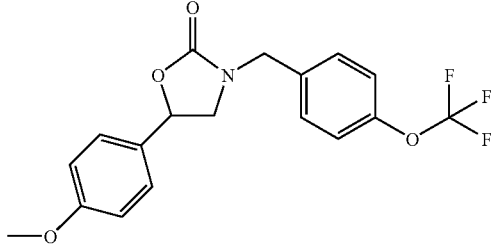 | 5-(4-Methoxyphenyl)-3-(4-trifluoromethoxybenzyl)-oxazolidin-2-one |
| 4 | 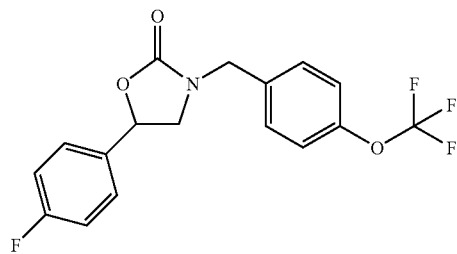 | 5-(4-Fluorophenyl)-3-(4-trifluoromethoxybenzyl)-oxazolidin-2-one |
| 5 | 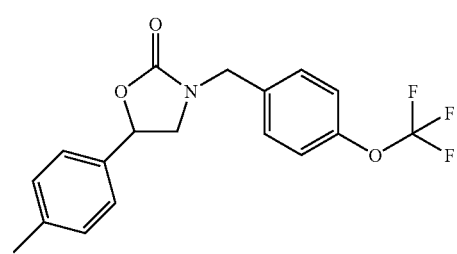 | 5-(4-Methylphenyl)-3-(4-trifluoromethoxybenzyl)-oxazolidin-2-one |

-continued

| No. | Structure | Name |
|---|---|---|
| 6 | 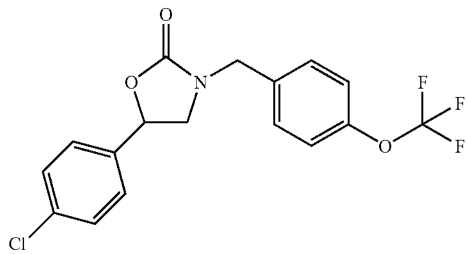 | 5-(4-Chlorophenyl)-3-(4-trifluoromethoxybenzyl)-oxazolidin-2-one |
| 7 | 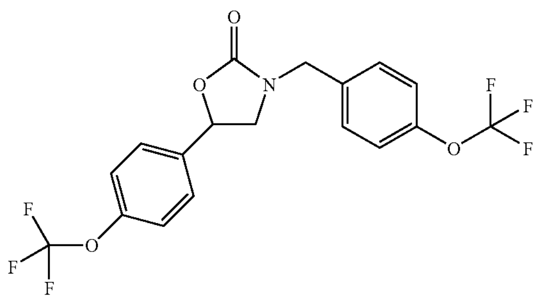 | 3-(4-Trifluoromethoxy-benzyl)-5-(4-trifluoromethoxy phenyl)-oxazolidin-2-one |
| 8 | 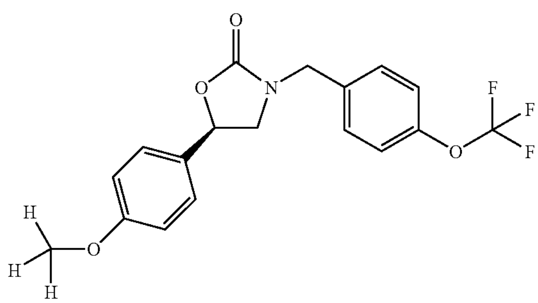 | 5-(4-Methoxyphenyl)-3-(4-trifluoromethoxybenzyl)-oxazolidin-2-one |
| 9 | 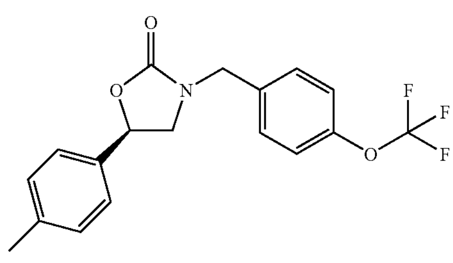 | 5-p-Tolyl-3-(4-trifluoromethoxybenzyl)-oxazolidin-2-one |
| 10 | 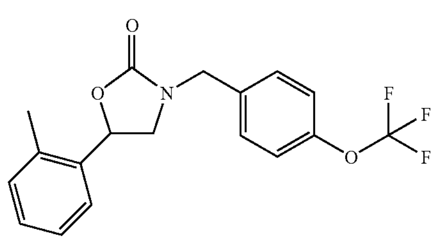 | 5-o-Tolyl-3-(4-trifluoromethoxybenzyl)-oxazolidin-2-one |

-continued

| No. | Structure | Name |
|---|---|---|
| 11 | 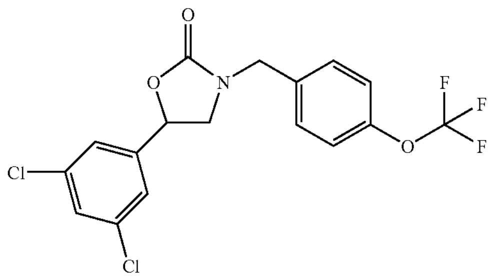 | 5-(3,5-Dichlorophenyl)-3-(4-trifluoromethoxybenzyl)-oxazolidin-2-one |
| 12 | 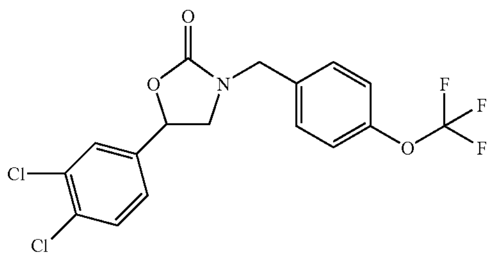 | 5-(3,4-Dichlorophenyl)-3-(4-trifluoromethoxybenzyl)-oxazolidin-2-one |
| 13 | 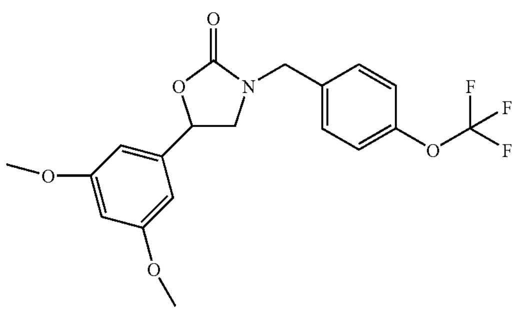 | 5-(3,5-Dimethoxyphenyl)-3-(4-trifluoromethoxybenzyl)-oxazolidin-2-one |
| 14 | 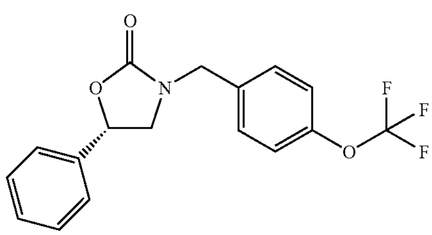 | 3-(4-Trifluoromethoxybenzyl)-5-(S)-phenyl-oxazolidin-2-one |
| 15 | 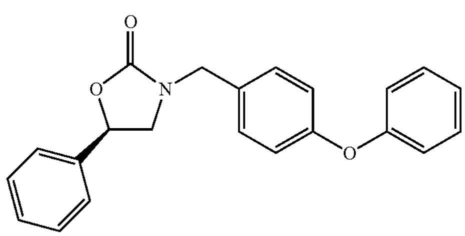 | 3-(4-Phenoxybenzyl)-5-(R)-phenyl-oxazolidin-2-one |
| 16 | 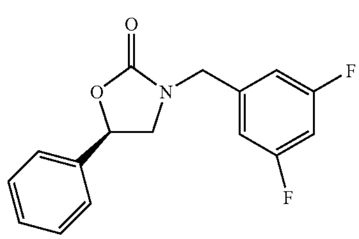 | 3-(3,5-Difluorobenzyl)-5-(R)-phenyl-oxazolidin-2-one |

-continued

| No. | Structure | Name |
|---|---|---|
| 17 | 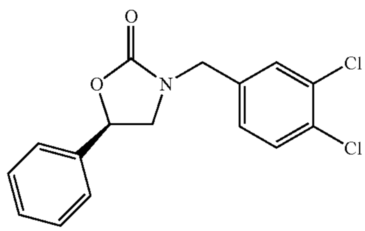 | 3-(3,4-Dichlorobenzyl)-5-(R)-phenyl-oxazolidin-2-one |
| 18 | 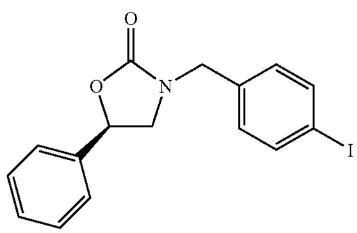 | 3-(4-Iodobenzyl)-5-(R)-phenyl-oxazolidin-2-one |
| 19 | 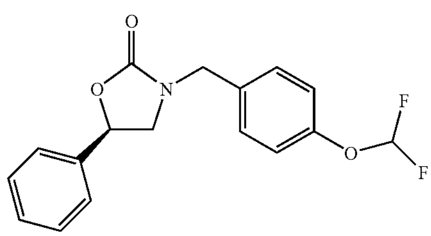 | 3-(4-Difluoromethoxbenzyl)-5-(R)-phenyl-oxazolidin-2-one |
| 20 | 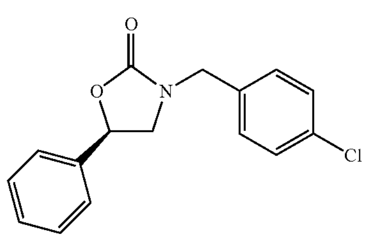 | 3-(4-Chlorobenzyl)-5-(R)-phenyl-oxazohdin-2-one |
| 21 | 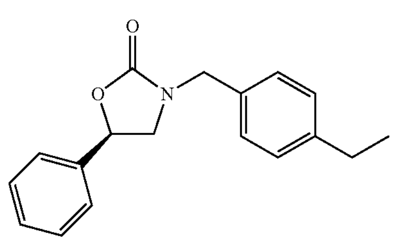 | 3-(4-Ethylbenzyl)-5-(R)-phenyl-oxazolidin-2-one |
| 22 | 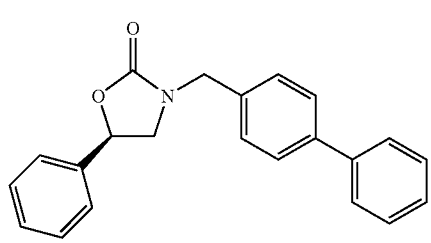 | 3-Biphenyl-4-ylmethyl-5-(R)-phenyl-oxazolidin-2-one |

-continued

| No. | Structure | Name |
| --- | --- | --- |
| 23 | 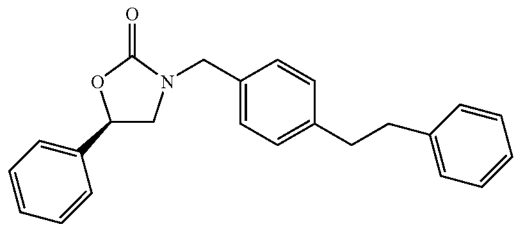 | 3-(4-Benzyloxybenzyl)-5-(R)-phenyl-oxazolidin-2-one |
| 24 | 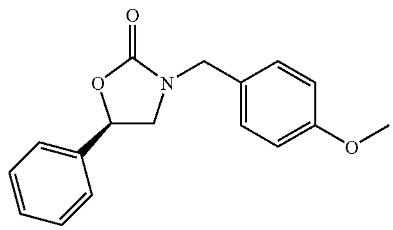 | 3-(4-Methoxybenzyl)-5-(R)-phenyl-oxazolidin-2-one |
| 25 | 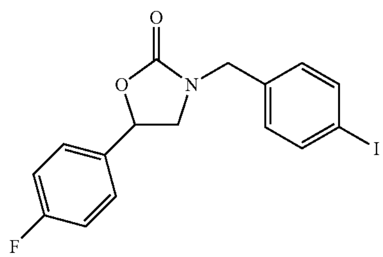 | 5-(4-Fluorophenyl)-3-(4-iodobenzyl)-oxazolidin-2-one |
| 26 | 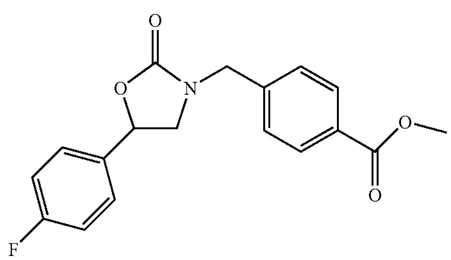 | 4-5[-(4-Fluorophenyl)-2-oxo-oxazolidin-3-ylmethyl]-benzoic acid methyl ester |
| 27 | 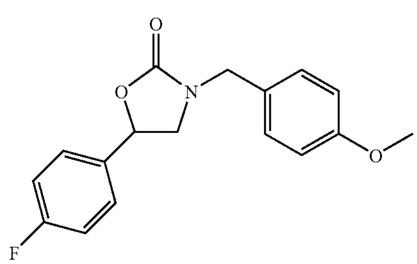 | 5-(4-Fluorophenyl)-3-(4-methoxybenzyl)-oxazolidin-2-one |
| 28 | 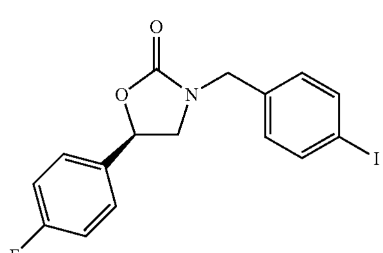 | 5-(R)-(4-Chlorophenyl)-3-(4-Iodobenzyl)-oxazolidin-2-one |

-continued

| No. | Structure | Name |
|---|---|---|
| 29 | 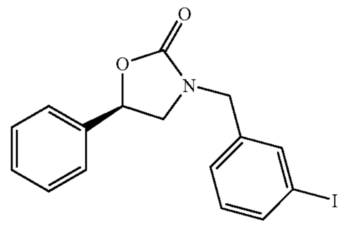 | 3-(3-Iodo-benzyl)-5-(R)-phenyl-oxazolidin-2-one |
| 30 | 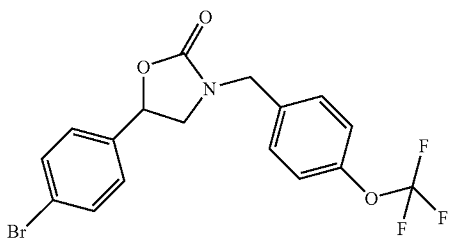 | 5-(4-Bromo-phenyl)-3-(4-trifluoromethoxy-benzyl)-oxazotidin-2-one |
| 31 | 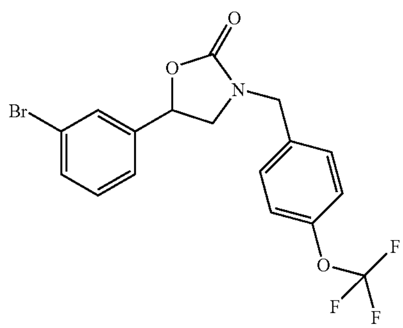 | 5-(3-Bromo-phenyl)-3-(4-trifluoromethoxy-benzyl)-oxazolidin-2-one |
| 32 | 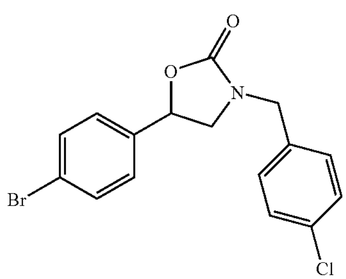 | 5-(4-Bromo-phenyl)-3-(4-chloro-benzyl)-oxazolidin-2-one |
| 33 | 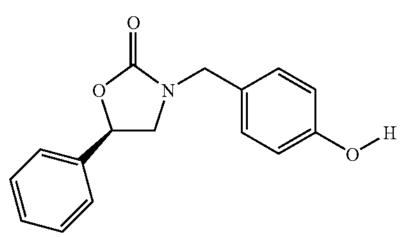 | 3-(4-Hydroxybenzyl)-5-(R)-phenyl-oxazolidin-2-one |
| 34 | 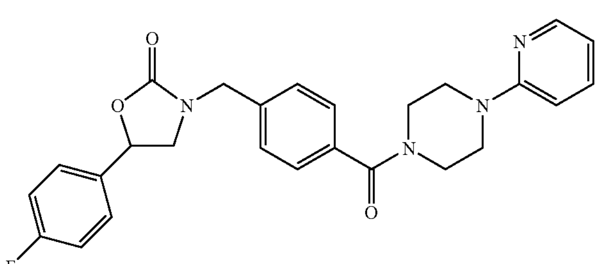 | 5-(4-Fluorophenyl-3-[4-(4-pyridin-2-yl-piperazine-1-carbonyl)-benzyl]-oxazolidin-2-one |

-continued

| No. | Structure | Name |
|---|---|---|
| 35 | 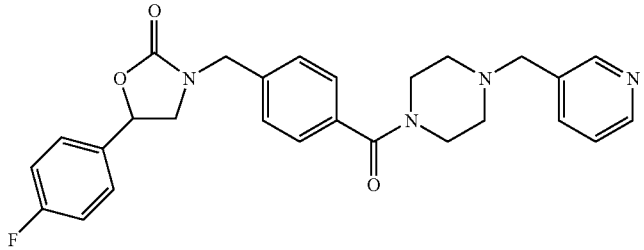 | 5-(4-Fluorophenyl)-3[4-(4-pyridin-3-ylmethyl-piperazine-1-carbonyl)-benzyl]-oxazolidin-2-one |
| 36 | 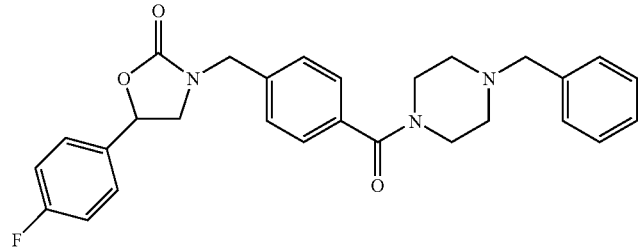 | 3-[4-(4-Benzyl-piperazine-1-carbonyl)-benzyl]-5-(4-fluorophenyl)-oxazolidin-2-one. |
| 37 | 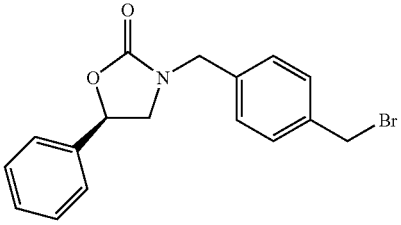 | 3-(4-Bromomethylbenzyl)-5-(R)-phenyl-oxazolidin-2-one |
| 38 | 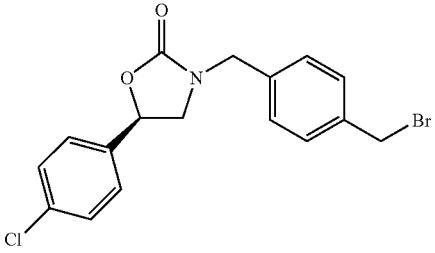 | 3-(4-Bromomethyl-benzyl)-5-(R)-(4-chlorophenyl)-oxazolidin-2-one |
| 39 | 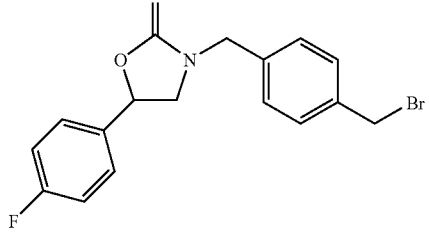 | 3-(4-Bromomethylbenzyl)-5-(4-fluorophenyl)-oxazolidin-2-one |
| 40 | 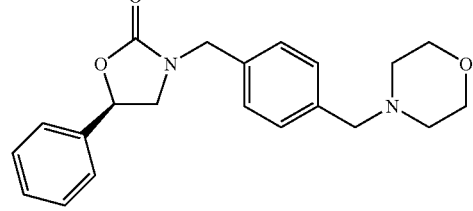 | 4-(Morpholin-4-ylmethyl-benzyl)-5-(R)-phenyl-oxazolidin-2-one |

-continued

| No. | Structure | Name |
|---|---|---|
| 41 | 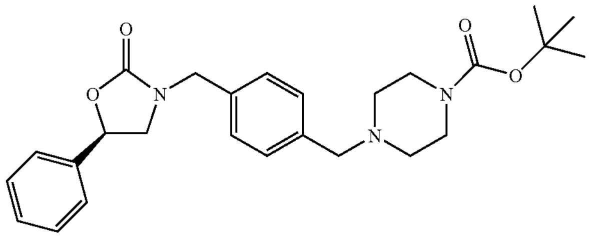 | 4-[4-(2-Oxo-5-(R)-phenyl-oxazolidin-3-ylmethyl)-benzyl]-piperazine-1-carboxylic acid tert-butyl-ester. |
| 42 | 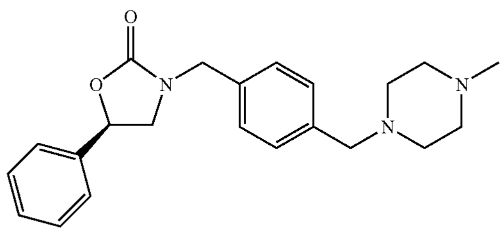 | 3-[4-(4-Methyl-piperazin-1-yhnethyl)-benzyl]-5-(R)-phenyl-oxazolidin-2-one |
| 43 | 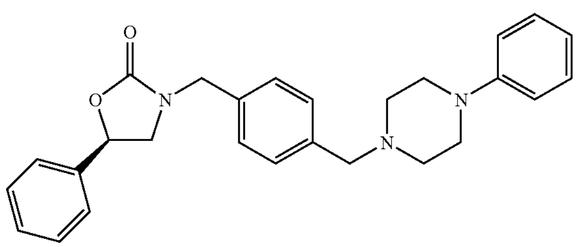 | 5-(R)-Phenyl-3-[4-(4-phenyl-piperazin-1-ylmethyl)-benyl]-oxazolidin-2-one |
| 44 | 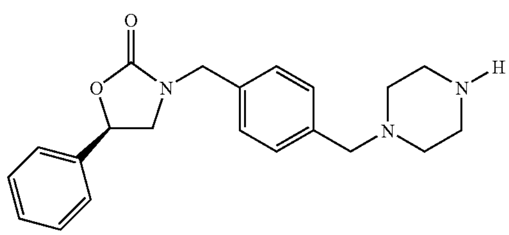 | 5-(R)-Phenyl-3-(4-piperazin-1-ylmethyl-benzyl)-oxazolidin-2-one |
| 45 | 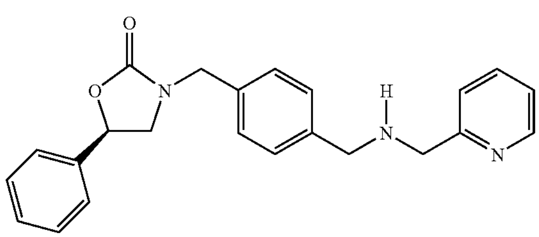 | 5-(R)-Phenyl-3-(4-{[(pyridine-2-yl methyl)-amino]-methyl}-benzyl)-oxazolidin-2-one |
| 46 | 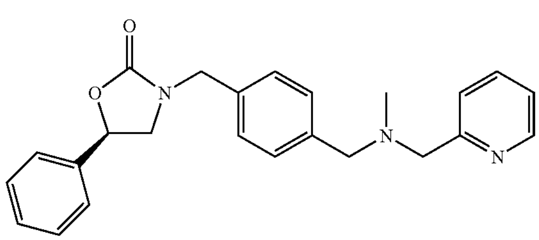 | 3-{4-[(Methyl-pyridin-2-ylmethyl-amino)-methyl]-benzyl}-5-(R)-phenyl-oxazolidine-2-one |

-continued

| No. | Structure | Name |
|---|---|---|
| 47 | 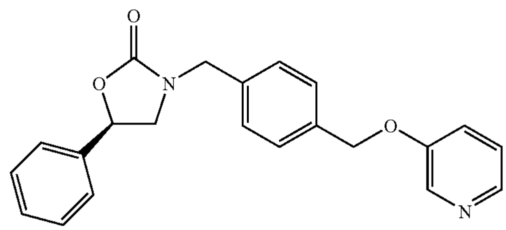 | 5-(R)-Phenyl-3-[4-(pyridine-3-yloxymethyl)-benzyl]-oxazolidin-2-one |
| 48 | 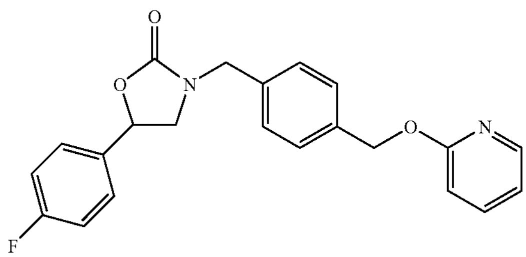 | 5-(4-Fluorophenyl)-3-[4-(pyridine-2-yloxymethyl)-benzyl]-oxazolidin-2-one |
| 49 | 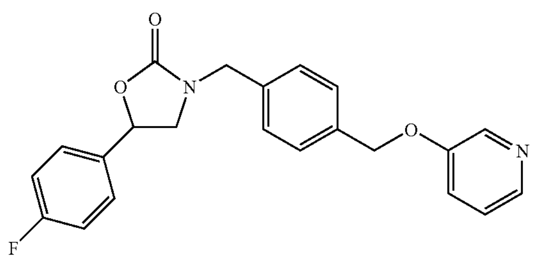 | 5-(4-Fluorophenyl)-3-[4-(pyridine-3-yloxymethyl)-benzyl]-oxazolidin-2-one |
| 50 | 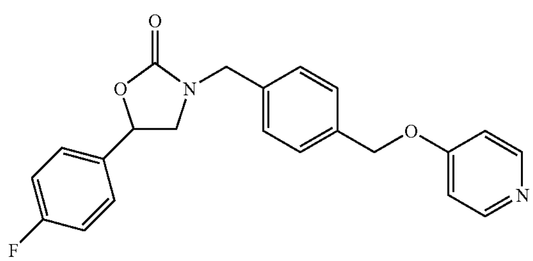 | 5-(4-Fluorophenyl)-3-(4-(pyridine-4-yloxymethyl)-beazyl]-oxazolidin-2-one |
| 51 | 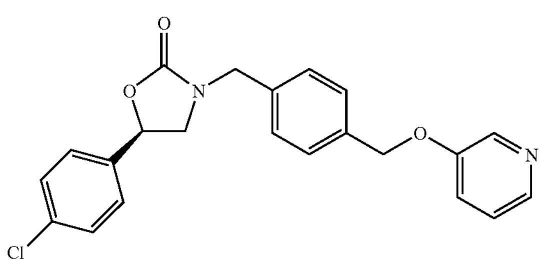 | 5-(R)-(4-Chlorophenyl)-3-[4-(pyridine-3-yloxymethyl)-benzyll-oxazolidin-2-one |
| 52 | 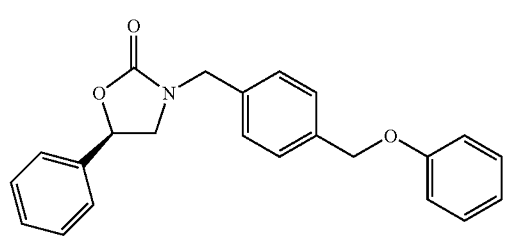 | 3-(4-Phenoxymethyl-benzyl)-5-(R)-phenyl-oxazolidin-2-one |

-continued

| No. | Structure | Name |
| --- | --- | --- |
| 53 | 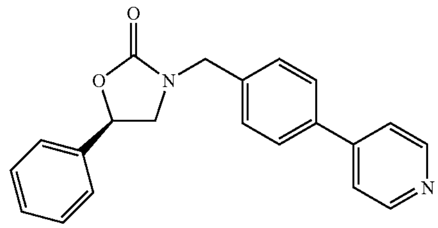 | 5-(R)-Phenyl-3-(4-Pyridin-4-yl-benzyl)-oxazolidin-2-one |
| 54 | 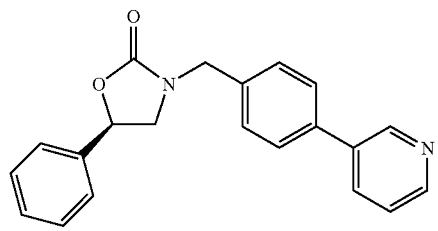 | 5-(R)-Phenyl-3-(4-Pyridin-3-yl-benzyl)-oxazolidin-2-one |
| 55 | 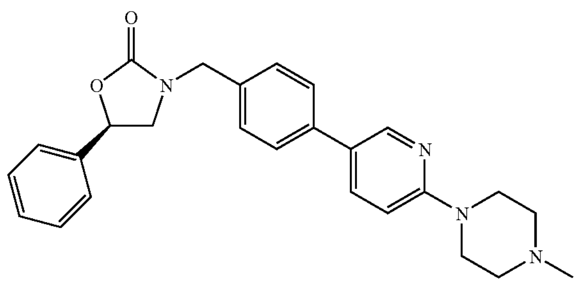 | 3-{4-[6-(4-Methyl-piperazin-1-yl)-pyridin-3-yl]-benzyl}-5-(R)-phenyl-oxazolidin-2-one |
| 56 | 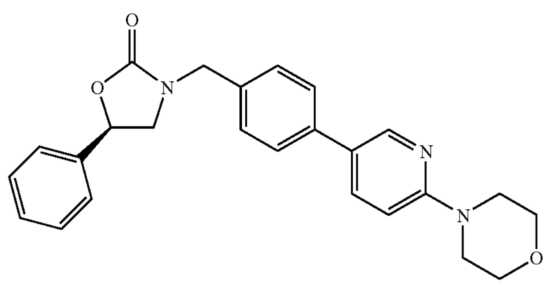 | 3-[4-(6-Morpholin-4-yl-pyridin-3-yl)-benzyl]-5-(R)-phenyl-oxazolidin-2-one |
| 57 | 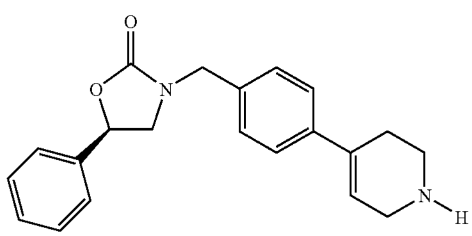 | 5-(R)-Phenyl-3-[4-(1,2,3,6-tetrahydro-pyridin-1-yl)-benzyl]-oxazolidin-2-one |
| 58 | 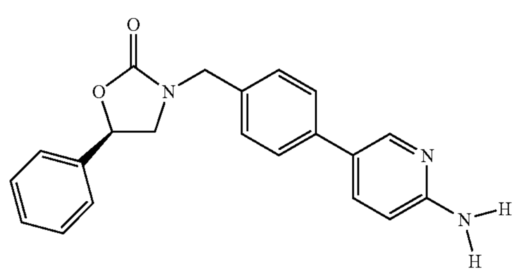 | 3-[4-(6-Amino-pyridin-3-yl)-benzyl]-5-(R)-phenyl-oxazolidin-2-one |

| No. | Structure | Name |
| --- | --- | --- |
| 59 | 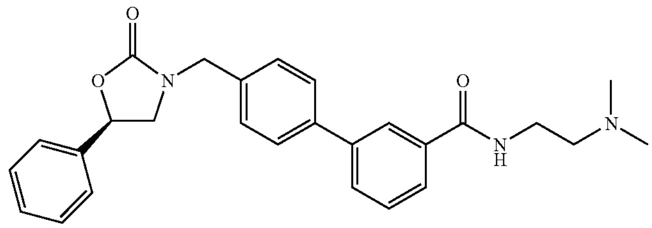 | 4'-(2-Oxo-5-(R)-phenyl-oxazolidin-3-ylmethyl) biphenyl-3-carboxylic acid (2-dimethylamino-ethyl)-amide |
| 60 | 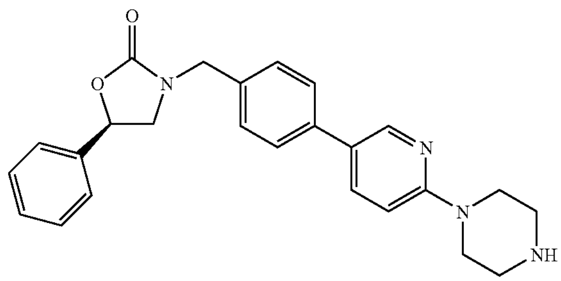 | 5-(R)-Phenyl-3-[4-(6-piperazin-1-yl-pyridin-3-yl)-benzyl]-oxazolidin-2-one |
| 61 | 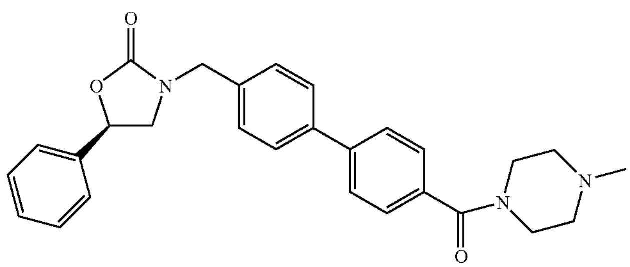 | 3-[4'-(4-Methyl-piperazine-1-carbonyl)-biphenyl-4-ylmethyl]-5-(R)-phenyl-oxazolidin-2-one |
| 62 | 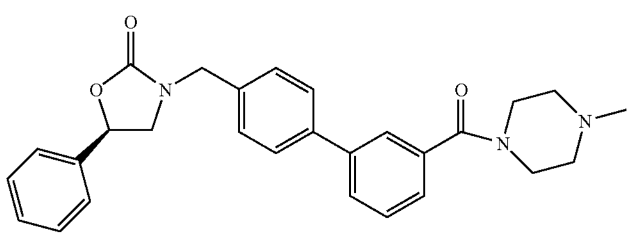 | 3-[3'-(4-Methyl-piperazine-1-carbonyl)-biphenyl-4-ylmethyl]-5-(R)-phenyl-oxazolidin-2-one |
| 63 | 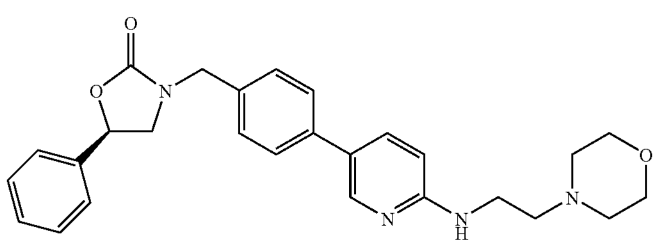 | 3-{4-[6-(2-Morpholin-4-yl-ethyl amino)-pyridin-3-yl]-benzyl}-5-(R)-phenyl-oxazolidin-2-one |
| 64 | 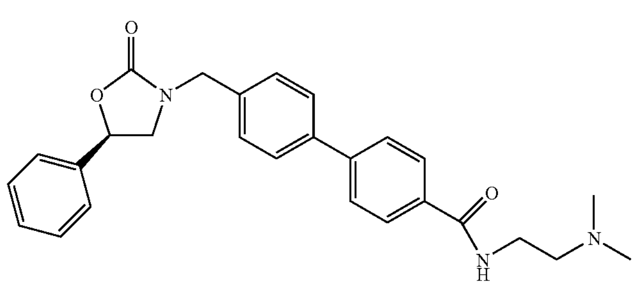 | 4'-(2-Oxo-5-(R)-phenyl-oxazolidin-3-ylmethyl) biphenyl-4-carboxylic acid (2-dimethylamino-ethyl)-amide |

| No. | Structure | Name |
|---|---|---|
| 65 | 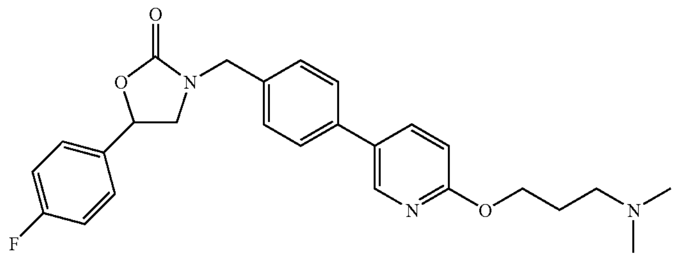 | 3-{4-[6-(3-Dimethyl amino-propoxy)-pyridin-3-yl]-benzyl}-5-(4-fluorophenyl-oxazolidin-2-one |
| 66 | 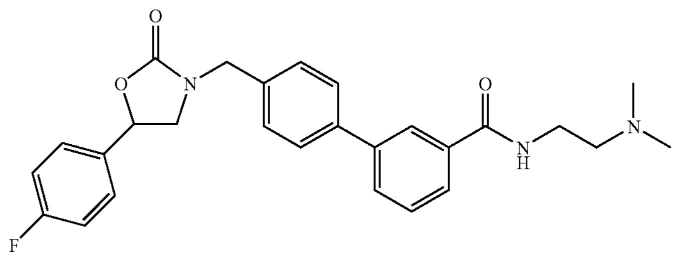 | 4'-[5-(4-Fluorophenyl)-2-oxo-oxazolidin-3-yl methyl]-biphenyl-3-carboxylic acid (2-dimethylamino-ethyl)-amide |
| 67 | 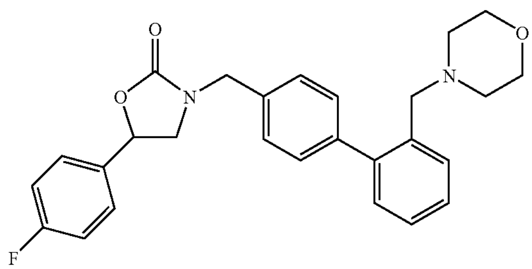 | 5-(4-Fluorophenyl)-3-(2'-morpholin-4-ylmethyl-biphenyl-4-ylmethyl)-oxazolidin-2-one |
| 68 | 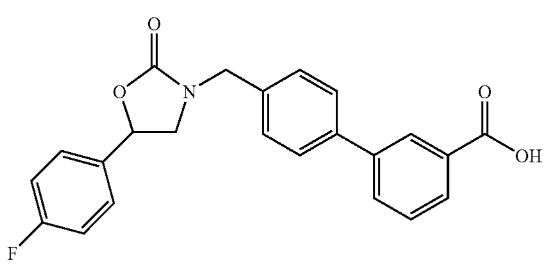 | 4'-[5-(4-Fluorophenyl)-2-oxo-oxazolidin-3-yl methyl]-biphenyl-3-carboxylic acid. |
| 69 | 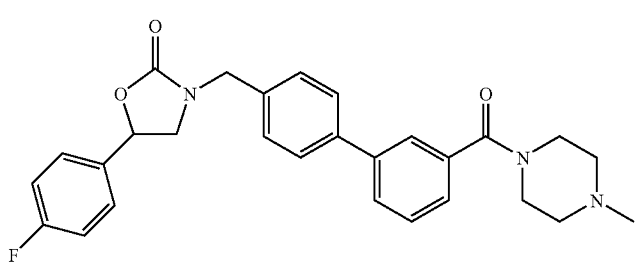 | 5-(4-Fluorophenyl)-3-[3'-(4-methyl-piperazine-1-carbonyl)-biphenyl4-ylmethyl]-oxazolidin-2-one. |

-continued

| No. | Structure | Name |
|---|---|---|
| 70 | 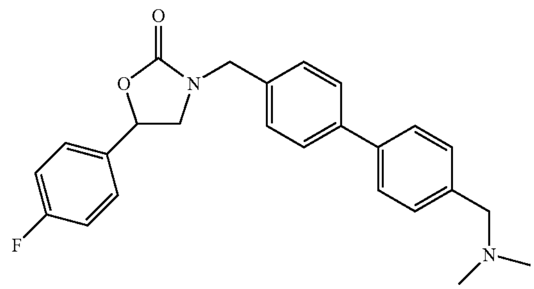 | 3-(4'-Dimethylamino methyl-biphenyl-4-ylmethyl)-5-(4-fluorophenyl)-oxazolidin-2-one. |
| 71 | 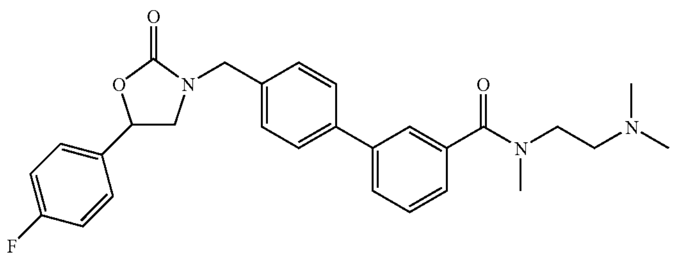 | 4'-[5-(4-Fluorophenyl)-2-oxo-oxazolidin-3-yl methyl]-biphenyl-3-carboxylic acid (2-dimethylamino-ethyl)-methyl-amide |
| 72 | 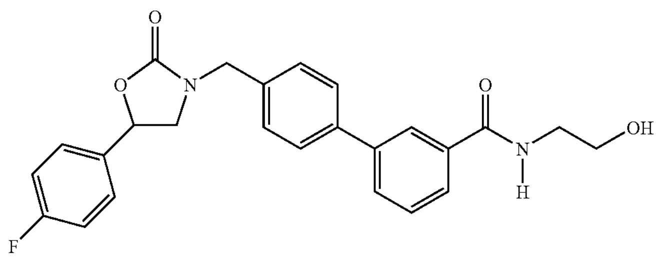 | 4'-[5-(4-Fluorophenyl)-2-oxo-oxazolidin-3-yl methyl]-biphenyl-3-carboxylic acid (2-hydroxyethyl)-amide |
| 73 | 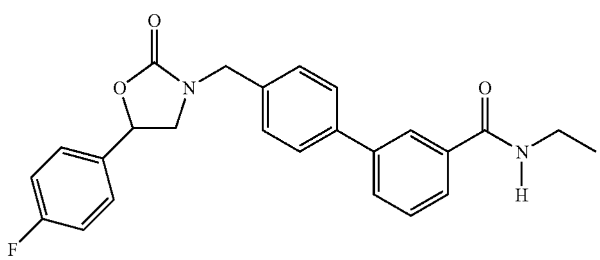 | 4'-[5-(4-Fluorophenyl)-2-oxo-oxazolidin-3-yl methyl]-biphenyl-3-carboxylic acid ethylamine |
| 74 | 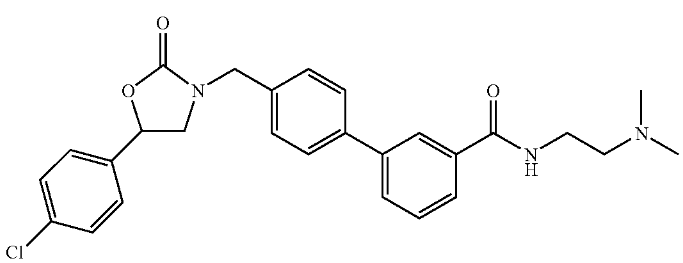 | 4'-[5-(R)-(4-Chlorophenyl)-2-oxo-oxazolidin-3-yl methyl]-biphenyl-3-carboxylic acid (2-dimethylamino-ethyl)-amide |
| 75 | 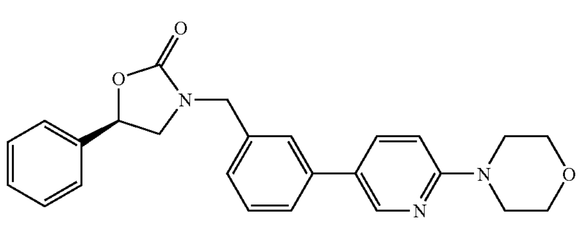 | 3-[3-(6-Morpholin-4-yl-pyridin-3-yl)-benzyl]-5-(R)-phenyl-oxazolidin-2-one |

-continued

| No. | Structure | Name |
|---|---|---|
| 76 | 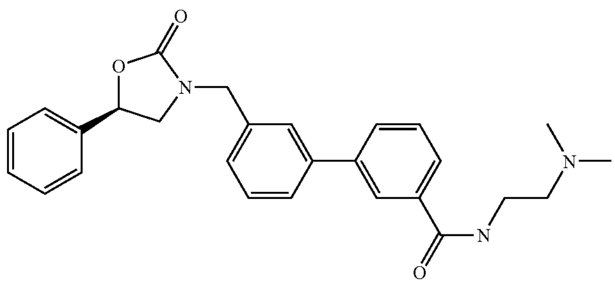 | 3'-(2-Oxo-5-(R)-phenyl-oxazolidin-3-yLrnethyl)-biphenyl-3-carboxylic acid (2-dimethylainino-ethyl)-amide |
| 77 | 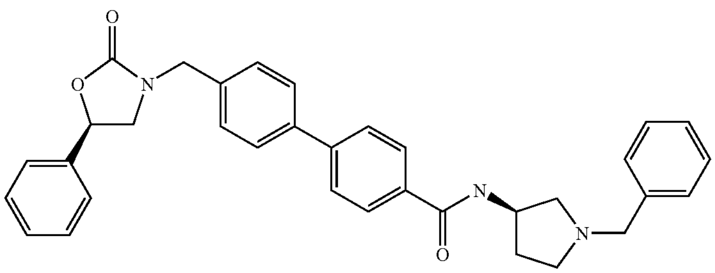 | 4'-(2-Oxo-5-(R)-phenyl-oxazolidin-3-ylmethyl)-biphenyl-4-carboxylic acid (1-benzyl-pyrrolidin-3-(S)-yl)-amide |
| 78 | 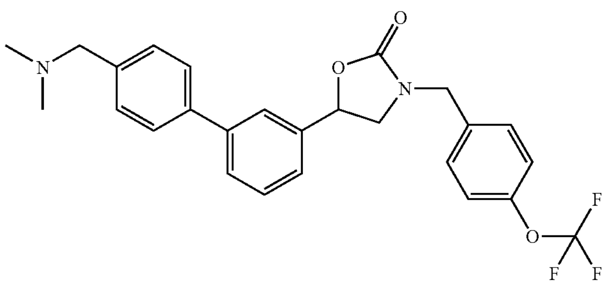 | 5-(4'-Dimethylaminomethyl-biphenyl-3-yl)-3-(4-trifluoromethoxy-beazyl)-oxazolidin-2-one |
| 79 | 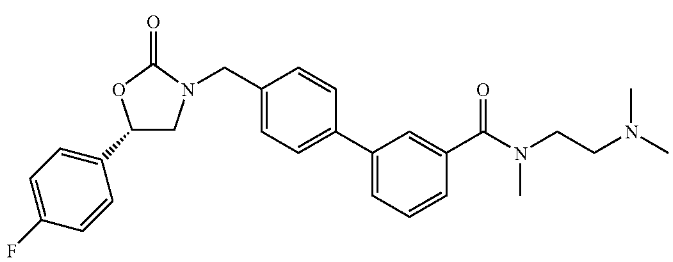 | 4'-[5-(S)-(4-Fluorophenyl)-2-oxo-oxazolidin-3-yl methyl]-biphenyl-3-carboxylic acid (2-dimethylamino-ethyl)-methyl-amide |
| 80 | 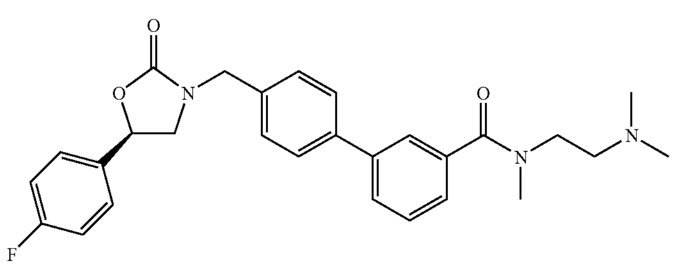 | 4'-[5-(R)-(4-Fluorophenyl)-2-oxo-oxazolidin-3-yl methyl]-biphenyl-3-cairboxylic acid (2-dimethylamino-ethyl)-methyl-amide |

| No. | Structure | Name |
| --- | --- | --- |
| 81 | 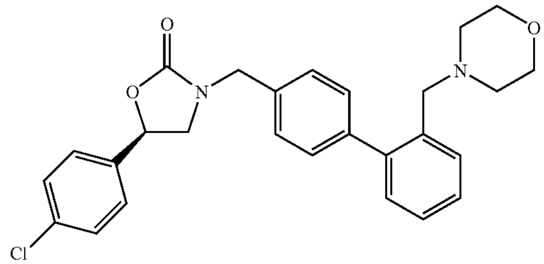 | 5-(R)-(4-Chlorophenyl)-3-(2'-morpholin-4-ylmethyl-biphenyl-4-ylmethyl)-oxazolidin-2-one |
| 82 | 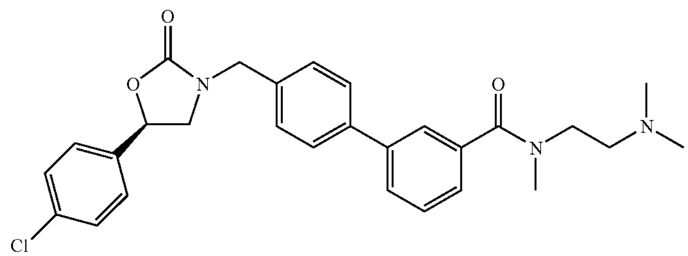 | 4'-[5-(R)-(4-Chlorophenyl)-2-oxo-oxazolidin-3-yl methyl]-biphenyl-3-carboxylic acid (2-dimethylamino-ethyl)-methyl-amide |
| 83 | 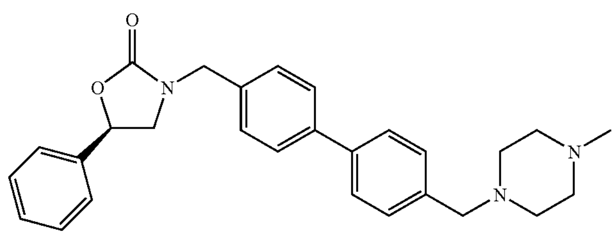 | 3-[4'-(4-Methyl-piperazin-1-ylmethyl)-biphenyl-4-yl methyl]-5-phenyl-oxazolidin-2-one |
| 84 | 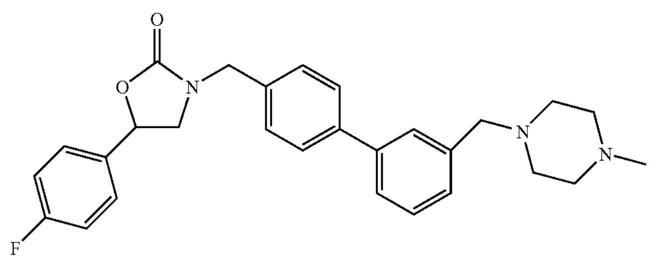 | 5-(4-Fluorophenyl)-3-[3'-(4-methyl-piperazin-1-ylmethyl)-biphenyl4-ylmethyl]-oxazolidin-2-one |
| 85 | 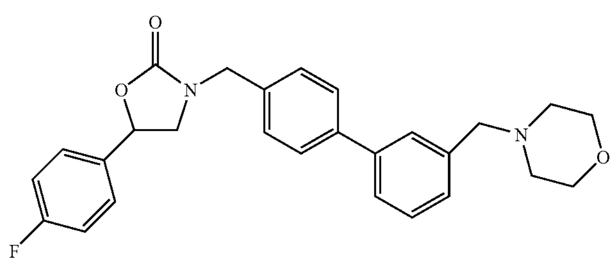 | 5-(4-Fluorophenyl)-3-(3'-morpholin-4-yl-methyl-biphenyl-4-ylmethyl)-oxazolidin-2-one |
| 86 | 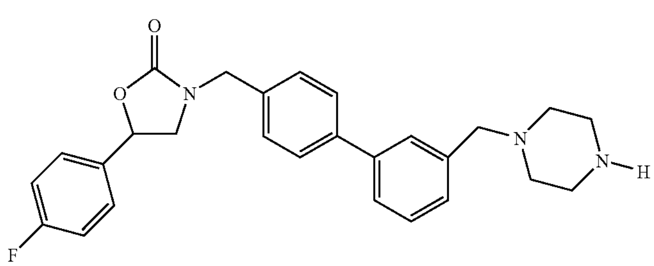 | 5-(4-Fluorophenyl)-3-(3'-piperazin-1-yl-methyl)-biphenyl-4-ylmethyl)-oxazolidin-2-one |

-continued

| No. | Structure | Name |
|---|---|---|
| 87 | 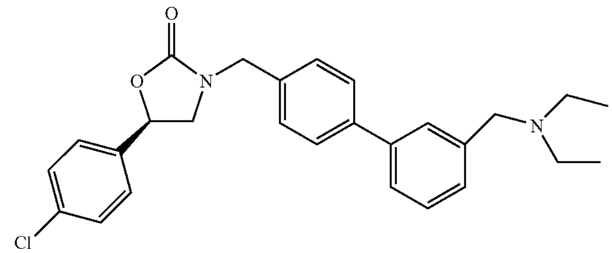 | 5-(R)-(4-Chlorophenyl)-3-(3'-diethylaminomethyl-biphenyl-4-ylmethyl)-oxazolidin-2-one |
| 88 | 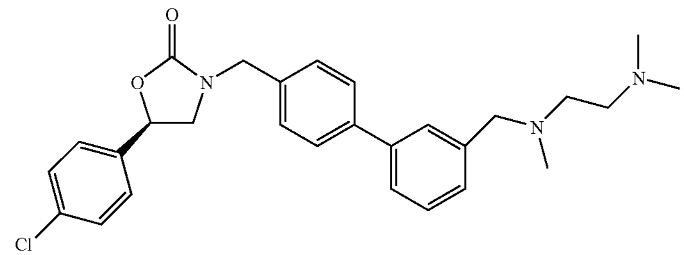 | 5-(R)-(4-Chlorophenyl)-3-(3'-{[(dimethylaminoethyl)-methylamino]-methyl}biphenyl-4-ylmethyl)-oxazolidin-2-one |
| 89 | 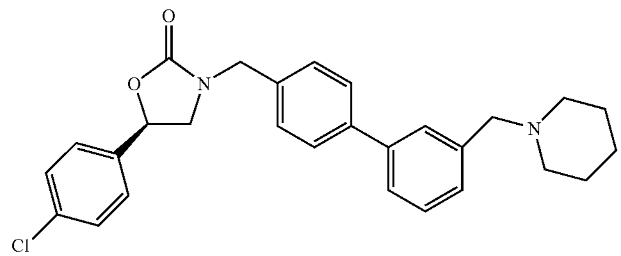 | 5-(R)-(4-Chlorophenyl)-3-(3'-piperidin-1-yl-methyl-biphenyl-4-ylmethyl)-oxazolidin-2-one |
| 90 | 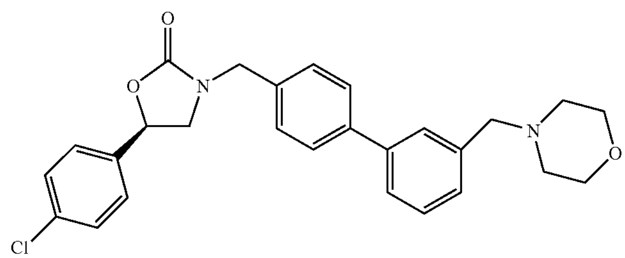 | 5-(R)-(4-Chlorophenyl)-3-(3'-morpholin-4-yl-methyl-biphenyl-4-ylmethyl)-oxazolidin-2-one |
| 91 | 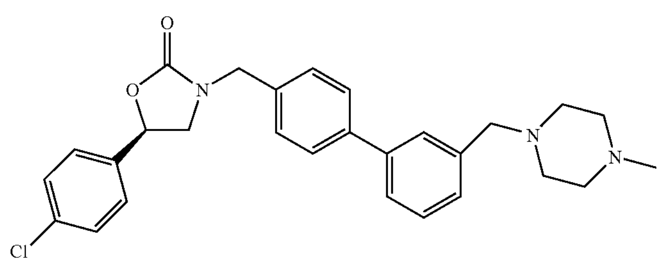 | 5-(R)-(4-Chlorophenyl)-3-[3'-(4-methyl-piperazin-1-ylmethyl)-biphenyl4-ylmethyl]-oxazolidin-2-one |
| 92 | 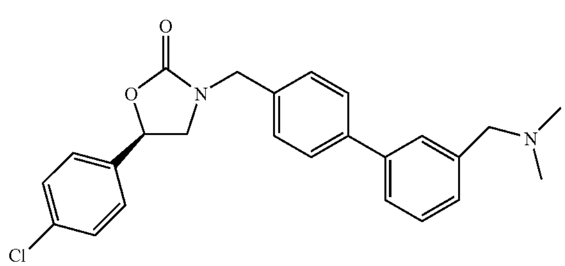 | 5-(R)-(4-Chlorophenyl)-3-(3'-dimethylaminomethyl-biphenyl-4-ylmethyl)-oxazolidin-2-one |

-continued

| No. | Structure | Name |
|---|---|---|
| 93 | 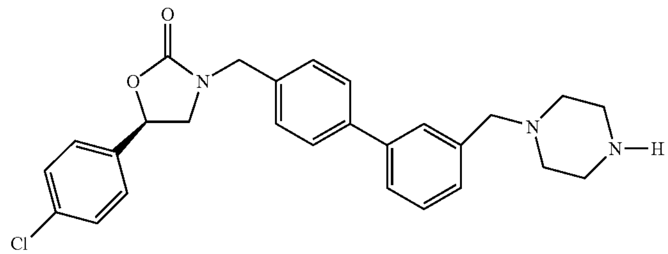 | 5-(R)-(4-Chlorophenyl)-3-(3'-piperazin-1-ylmethyl)-biphenyl-4-ylmethyl)-oxazolidin-2-one |
| 94 | 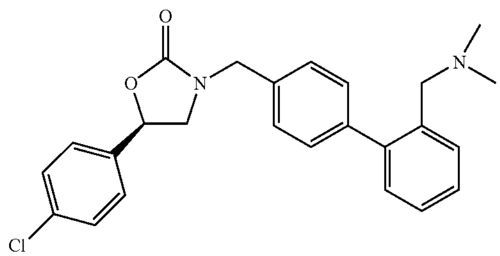 | 5-(R)-(4-Chlorophenyl)-3-(2'-dimethylaminomethyl-biphenyl-4-ylmethyl)-oxazolidin-2-one. |
| 95 | 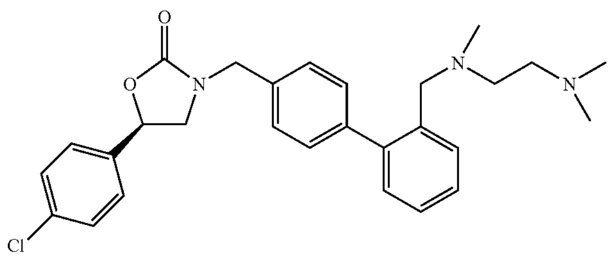 | 5-(R)-(4-Chlorophenyl)-3-(2'-{[(2-dimethylaminoethyl) - methyl-amino]-methyl}-biphenyl-4-yl methyl)-oxazohckn-2-one. |
| 96 | 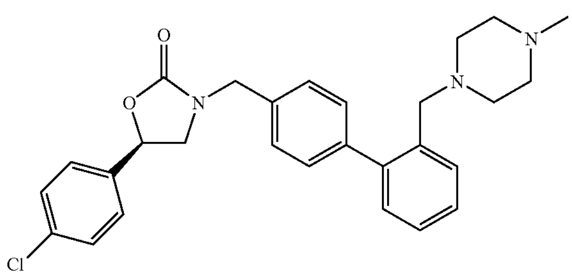 | 5-(R)-(4-Chlorophenyl)-3-[2'-(4-methyl-piperazin-1-yl methyl)-biphenyl-4-ylmethyl)-oxazolidin-2-one |
| 97 | 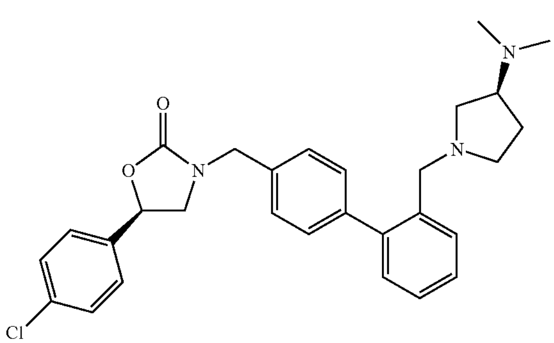 | 5-(R)-(4-Chlorophenyl)-3-[2'-(3-(S)-dimethylamino-pyrrolidin-1-yl methyl)-1-biphenyl-4-ylmethyl]-oxazolidin-2-one |

-continued

| No. | Structure | Name |
| --- | --- | --- |
| 98 | 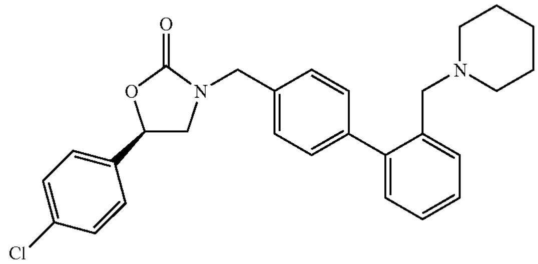 | 5-(R)-(4-Chlorophenyl)-3-(2'-piperidin-1-yl methyl-biphenyl-4-ylmethyl)-oxazolidin-2-one |
| 99 | 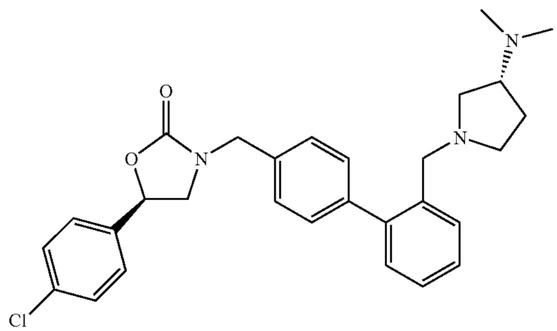 | 5-(R)-(4-Chlorophenyl)-3-[2'-(3-(R)-dimethylamino-pyrrolidin-1-yl methyl)-1-biphenyl-4-ylmethyl]-oxazolidiin-2-one |
| 100 | 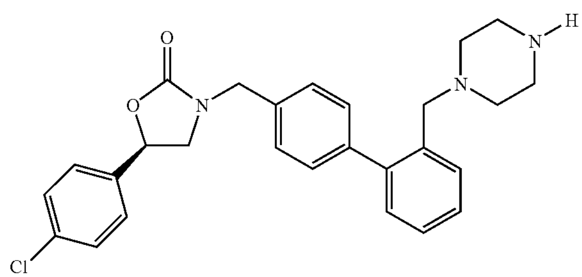 | 5-(R)-(4-Chlorophenyl)-3-(2'-piperazin-1-yl methyl-biphenyl-4-ylmethyl)-oxazotidin-2-one |
| 101 | 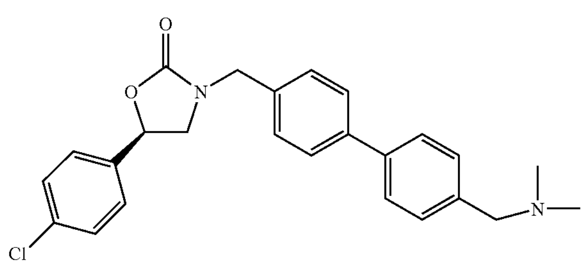 | 5-(R)-(4-Chlorophenyl)-3-(4'-dimetbylaminomethyl-biphenyl-4-ylmethyl)-oxazolidin-2-one. |
| 102 | 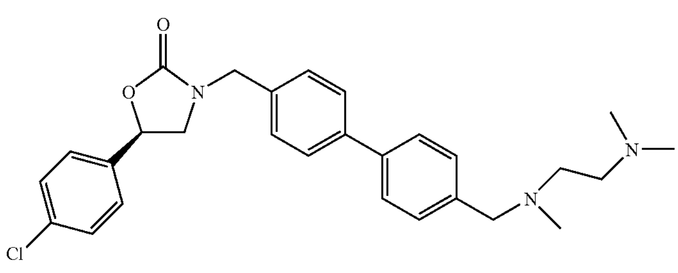 | 5-(R)-(4-Chlorophenyl)-3-(4'-{[(2-dimethylaminoethyl)-methyl-amino]-metnyl}-biphenyl-4-yl methyl)-oxazolidin-2-one. |

-continued

| No. | Structure | Name |
|---|---|---|
| 103 | 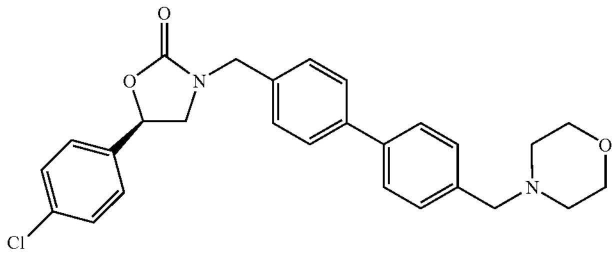 | 5-(R)-(4-Chlorophenyl)-3-(4'-morpholin-4-yl methyl-biphenyl-4-ylmethyl)-oxazolidin-2-one. |
| 104 | 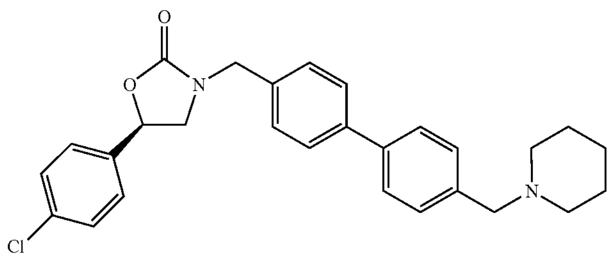 | 5-(R)-(4-Chlorophenyl)-3-(4'-piperidin-1-yl methyl-biphenyl-4-ylmethyl)-oxazolidin-2-one |
| 105 | 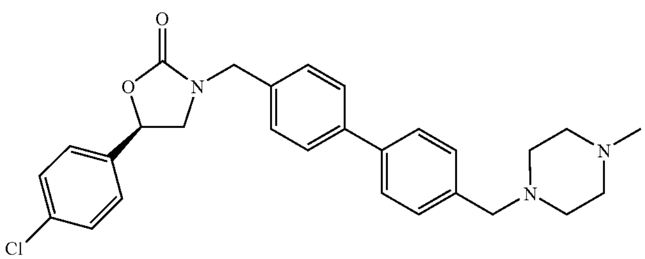 | 5-(R)-(4-Chlorophenyl)-3-[4'-(4-methyl-piperazin-1-yl methyl)-biphenyl-4-ylmethyl)-oxazolidin-2-one |
| 106 | 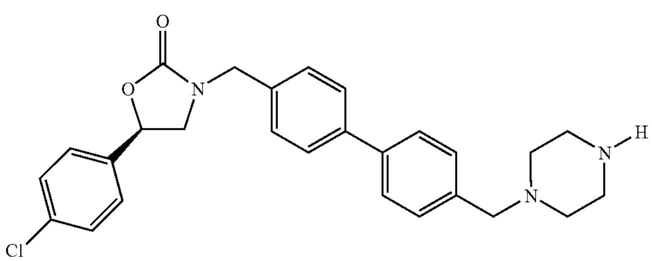 | 5-(R)-(4-Chlorophenyl)-3-(4'-piperazin-1-yl methyl-biphenyl-4-ylmethyl)-oxazolidin-2-one |
| 107 | 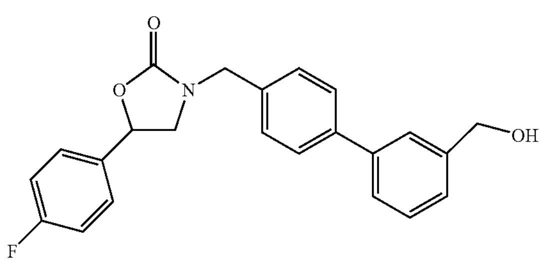 | 5-(4-Fluorophenyl)-3-(3'-hydroxymethyl biphenyl-4-ylmethyl)-oxazolidin-2-one |
| 108 | 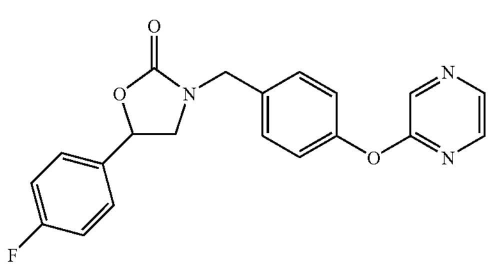 | 5-(4-Fluorophenyl)-3-[4-(pyrazin-2-yloxy)-benzyl]-oxazolidin-2-one |

-continued

| No. | Structure | Name |
|---|---|---|
| 109 | 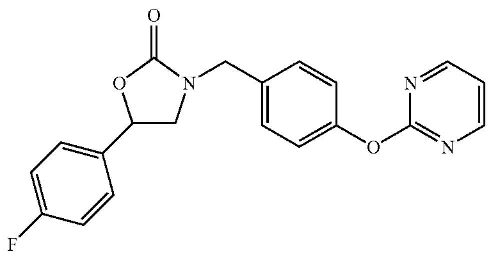 | 5-(4-Fluorophenyl)-3-[4-(pyrimidin-2-yloxy)-benzyl]-oxazolidin-2-one |
| 110 | 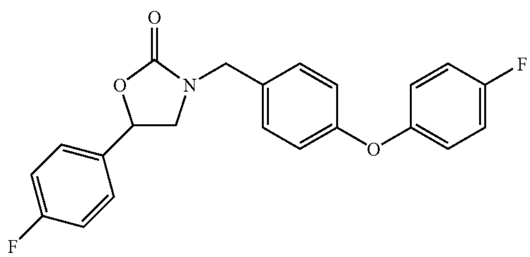 | 3-[4-(4-Fluorophenoxy)-benzyl]-5-(4-fluorophenyl)-oxazolidin-2-one |
| 111 | 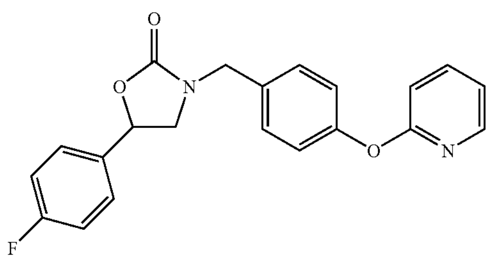 | 5-(4-Fluorophenyl)-3-[4-(pyridin-2-yloxy)-benzyl]-oxazolidin-2-one |
| 112 | 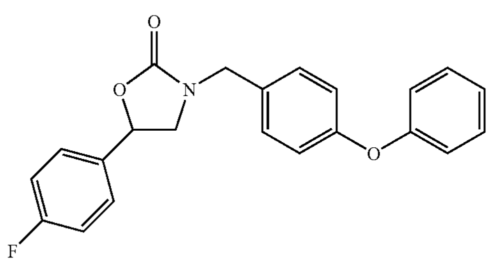 | 5-(4-Fluorophenyl)-3-(4-phenoxy-benzyl)-oxazolidin-2-one |
| 113 | 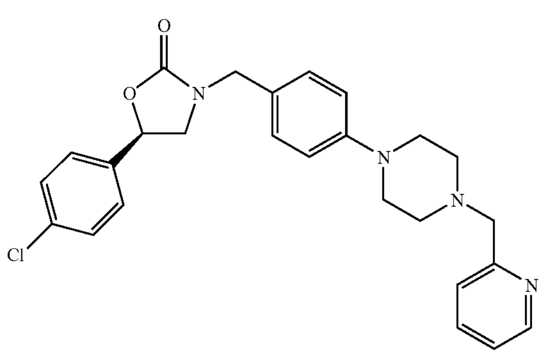 | 5-(R)-(4-Chlorophenyl)-3-[4-(4-pyridin-2-ylmethyl-piperazin-1-yl)-benzyl]-oxazolidin-2-one |

-continued

| No. | Structure | Name |
|---|---|---|
| 114 | 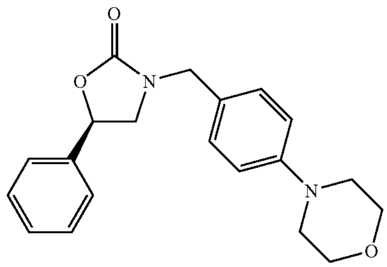 | 3-(4-Morpholin-4-yl-benzyl)-5-(R)-phenyl-oxazolidin-2-one |
| 115 | 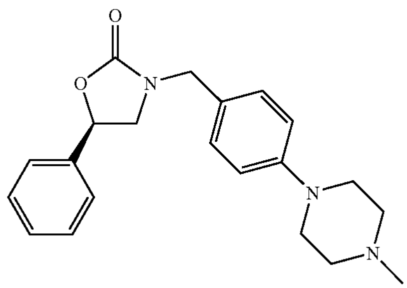 | 3-[4-(4-Methyl-piperazin-1-yl)-benzyl]-5-(R)-phenyl-oxazolidin-2-one |
| 116 | 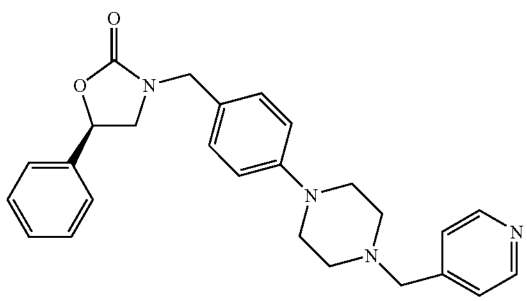 | 5-(R)-Phenyl-3-[4-(4-pyridin-4-ylmethyl-apiperazin-1-yl)-benzyl]-oxazolidin-2-one |
| 117 | 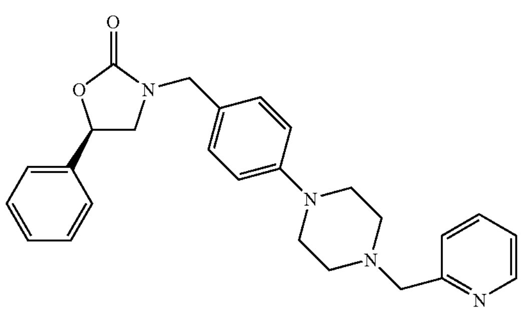 | 5-(R)-Phenyl-3-[4-(4-pyridin-2-ylmethyl-piperazin-1-yl)-benzyl]-oxazolidin-2-one |
| 118 | 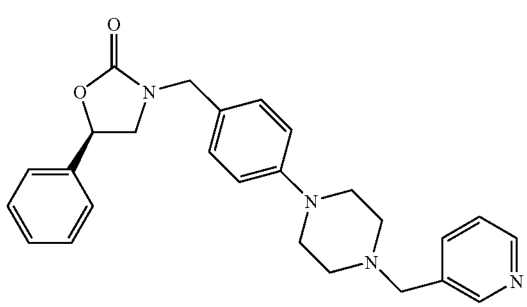 | 5-(R)-Phenyl-3-[4-(4-pyridin-3-ylmethyl-piperazin-1-yl)-benzyl]-oxazolidin-2-one |

-continued

| No. | Structure | Name |
|---|---|---|
| 119 | 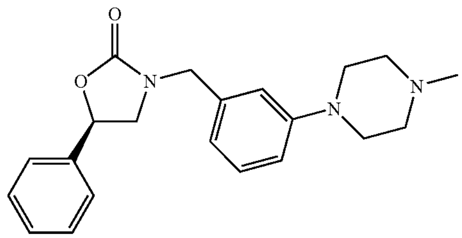 | 3-[3-(4-Methyl-piperazin-1-yl)-benzyl]-5-(R)-phenyl-oxazolidin-2-one |
| 120 | 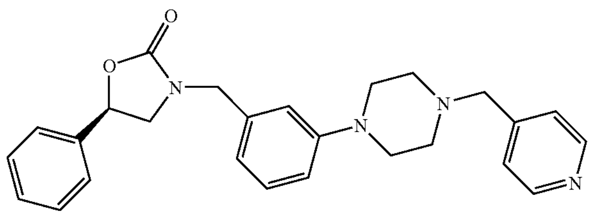 | 5-(R)-Phenyl-3-[3-(4-pyridin-4-ylmethyl-piperazin-1-yl)-benzyl]-oxazolidin-2-one |
| 121 | 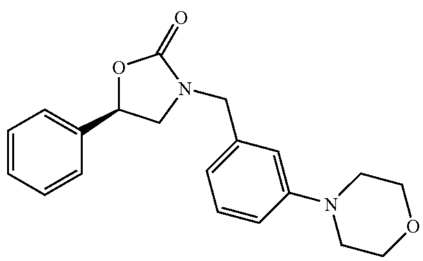 | 3-(3-Morpholin-4-yl-benzyl)-5-(R)-phenyl-oxazolidin-2-one |
| 122 | 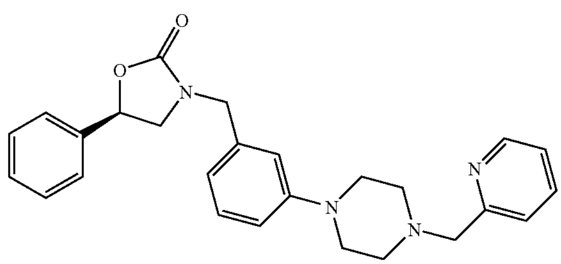 | 5-(R)-Phenyl-3-[4-(4-pyridin-2-ylmethyl-piperazin-1-ylmethyl)-benzyl]-oxazolidin-2-one |
| 123 | 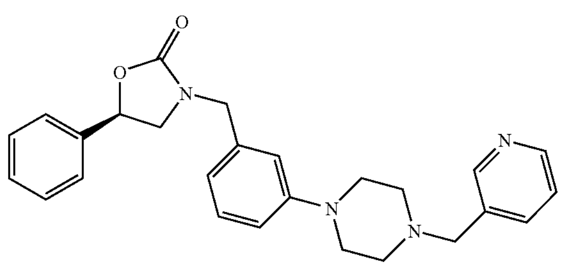 | 5-(R)-Phenyl-3-[4-(4-pynchn-3-ylmethyl-piperazin-1-ylmethyl)-benzyl]-oxazolidin-2-one |
| 124 | 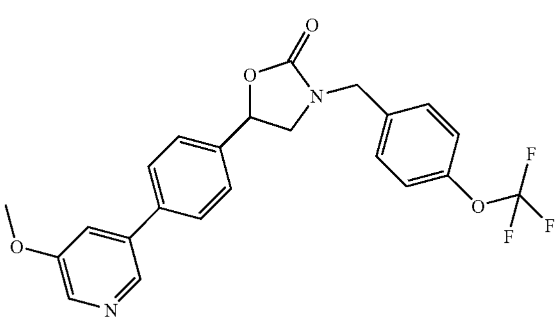 | 5-[4-(5-Methoxy-pyridin-3-yl)-phenyl]-3-(4-trifluoro-methoxy-benzyl)-oxazolidin-2-one |

-continued

| No. | Structure | Name |
|---|---|---|
| 125 | 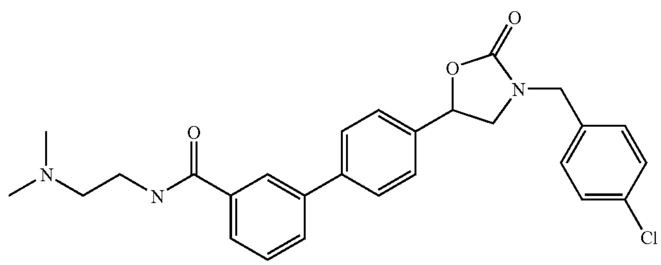 | 4'-[3-(4-Chloro-benzyl)-2-oxo-oxazolidin-5-yl]-biphenyl-3-carboxylic acid (2-dimethylamino-ethyl)-amide |

Pharmaceutical Composition

The compounds of the present invention may be formulated into conventional pharmaceutical composition comprising a compound of Formula I, or a pharmaceutically acceptable salt or solvate thereof, in association with a pharmaceutically acceptable carrier or excipient. The pharmaceutically acceptable carriers can be either solid or liquid. Solid form preparations include, but are not limited to, powders, tablets, dispersible granules, capsules, cachets, and suppositories.

A solid carrier can be one or more substances, which may also act as diluents, flavoring agents, solubilizers, lubricants, suspending agents, binders, or table disintegrating agents. A solid carrier can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized moulds and allowed to cool and solidify.

Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

Depending on the mode of administration, the pharmaceutical composition will include from about 0.05% w (percent by weight) to about 99% w, more particularly, from about 0.10% w to 50% w, of the compound of the invention, all percentages by weight being based on the total weight of the composition.

A therapeutically effective amount for the practice of the present invention can be determined by one of ordinary skill in the art using known criteria including the age, weight and response of the individual patient, and interpreted within the context of the disease which is being treated or which is being prevented.

Medical Use

It has been discovered that the compounds of the present invention exhibit activity as pharmaceuticals, in particular as modulators of metabotropic glutamate receptors. More particularly, the compounds of the present invention exhibit activity as potentiators of the mGluR2 receptor, and are useful in therapy, in particular for the treatment of neurological and psychiatric disorders associated with glutamate dysfunction in an animal.

More specifically, the neurological and psychiatric disorders include, but are not limited to, disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, and conduct disorder.

The invention thus provides a use of any of the compounds according to Formula I, or a pharmaceutically acceptable salt or solvate thereof, for the manufacture of a medicament for the treatment of any of the conditions discussed above.

Additionally, the invention provides a method for the treatment of a subject suffering from any of the conditions discussed above, whereby an effective amount of a compound according to Formula I or a pharmaceutically acceptable salt or solvate thereof, is administered to a patient in need of such treatment. The invention also provides a compound of Formula I or pharmaceutically acceptable salt or solvate thereof, as hereinbefore defined for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses the administration of an effective amount of a compound of the present invention, to mitigate either a pre-existing disease state, acute or chronic, or to mitigate a recurring condition. This definition also encompasses prophylactic therapies for prevention of recurring conditions and continued therapy for chronic disorders. In use for therapy in a warm-blooded animal such as a human, the compounds of the present invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints. In preferred embodiments of the invention, the route of administration is oral, intravenous, or intramuscular.

The dosage will depend on the route of administration, the severity of the disease, age and weight of the patient and other factors normally considered by the attending physician, who determines the individual regimen and dosage level for a particular patient.

As mentioned above, the compounds described herein may be provided or delivered in a form suitable for oral use, for example, in a tablet, lozenge, hard and soft capsule, aqueous solution, oily solution, emulsion, and suspension. Alternatively, the compounds may be formulated into a topical administration, for example, as a cream, ointment, gel, spray, or aqueous solution, oily solution, emulsion or suspension. The compounds described herein also may be provided in a form that is suitable for nasal administration, for example, as a nasal spray, nasal drops, or dry powder. The compounds can be administered to the vagina or rectum in the form of a suppository. The compounds described herein also may be administered parentally, for example, by intravenous, intravesicular, subcutaneous, or intramuscular injection or infusion. The compounds can be administered by insufflation (for example as a finely divided powder). The compounds may also be administered transdermally or sublingually.

In addition to their use in therapeutic medicine, the compounds of Formula I, or salts thereof, are useful as pharmacological tools in the development and standardization of in vitro and in vivo test systems for the evaluation of the effects of inhibitors of mGluR-related activity in laboratory animals as part of the search for new therapeutics agents. Such animals include, for example, cats, dogs, rabbits, monkeys, rats and mice.

Process for Preparing

Compounds of the present invention can be prepared by various synthetic processes. The selection of a particular process to prepare a given compound is within the purview of the person of skill in the art. The choice of particular structural features and/or substituents may therefore influence the selection of one process over another.

Within these general guidelines, the following processes can be used to prepare exemplary subsets of compounds of this invention. Unless indicated otherwise, the variables described in the following schemes and processes have the same definitions as those given for Formula I above.

In one process, for example, compounds of Formula I wherein $R^1$ is a phenyl group may be prepared as shown in Scheme 1, below:

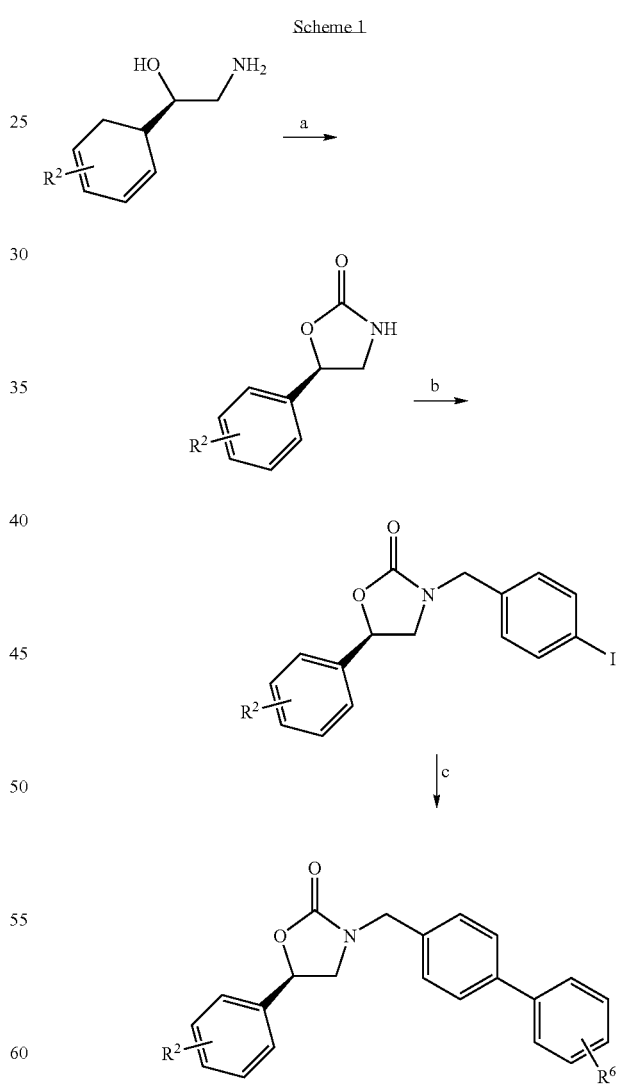

a) dichloromethane, di-2-pyridyl carbonate, O/N, RT.
b) acetonitrile, 4-iodobenzylbromide, cesium carbonate, 70° C., 4 h.
c) dimethoxy ethane, boronate ester, 2m aq. sodium carbonate, Pd(PPh$_3$)$_4$, 100°-110° C. 1.5 h Compounds of Formula I wherein R¹ is a (CO)piperazine group may be prepared as shown in Scheme 2, below:

Scheme 2

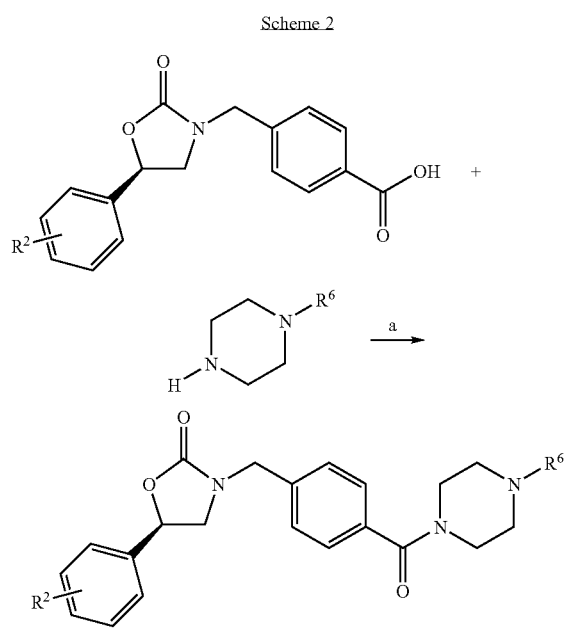

a) DMF, EDCl, HOBT, RT, O/N

Compounds of Formula I wherein R¹ is an alkyleneNR⁷R⁸ group may be prepared as shown in Scheme 3, below:

Scheme 3

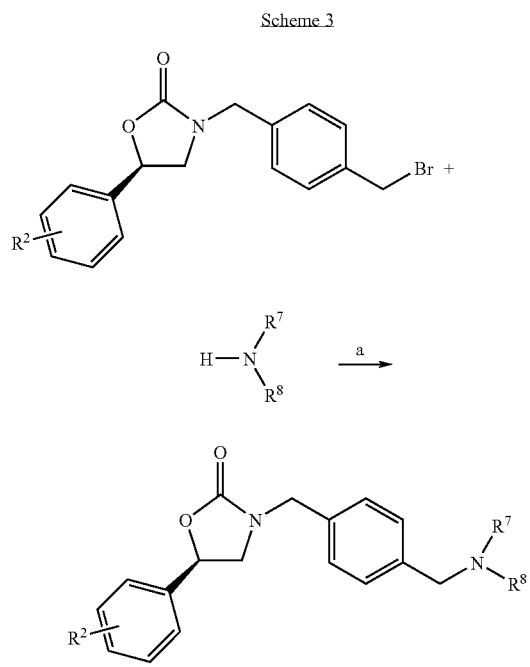

a) CH₃CN, 70° C., 4 h

Compounds of Formula I wherein R¹ is an alkyleneOR⁷ group may be prepared as shown in Scheme 4, below:

Scheme 4

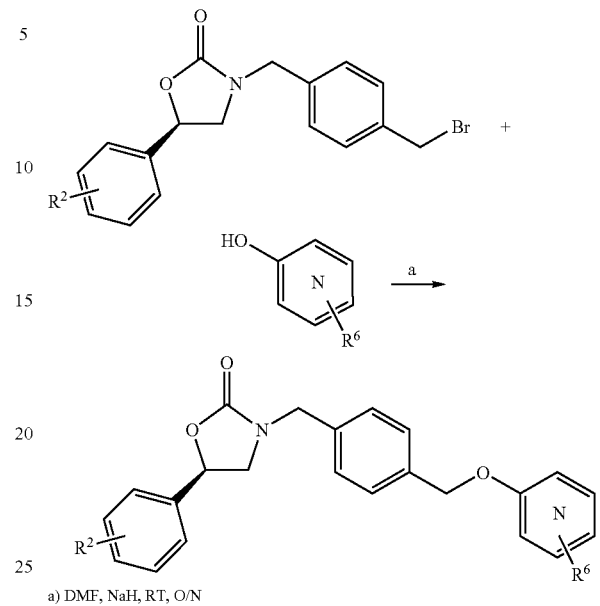

a) DMF, NaH, RT, O/N

Compounds of Formula I wherein R¹ is an O-aryl group may be prepared as shown in Scheme 5, below:

Scheme 5

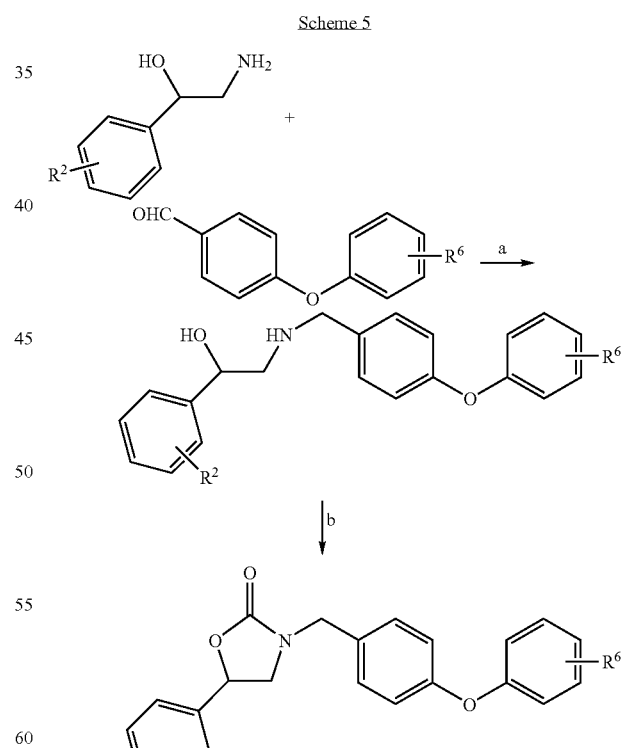

a) MeOH, Acetic acid, sodium cyanoborohydride, RT, O/N
b) dichloromethane, diisopropyl ethylamine, triphosgene Compounds of Formula I wherein R¹ is a heterocycloalkyl group may be prepared as shown in Scheme 6, below:

Scheme 6

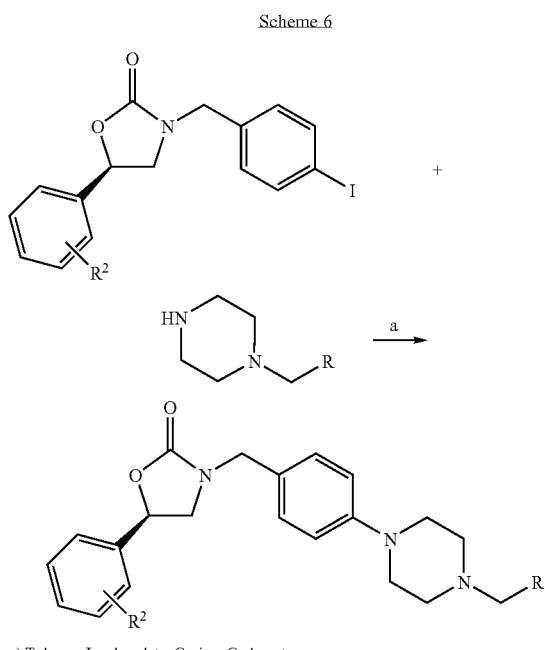

a) Toluene, Lead acelate, Cesium Carbonate,
2-(dicyclohaxyl phosphino)biphenyl, 100° C., 3 h Many variations of the foregoing processes and additions thereto appear throughout the examples that follow. The person of ordinary skill in the art thus will appreciate that the compounds of this invention can be prepared by following or adapting one or more of the processes disclosed herein.

The invention is further illustrated by way of the following examples, which are intended to elaborate several embodiments of the invention. These examples are not intended to, nor are they to be construed to, limit the scope of the invention. It will be clear that the invention may be practiced otherwise than as particularly described herein. Numerous modifications and variations of the present invention are possible in view of the teachings herein and, therefore, are within the scope of the invention.

General Methods

All starting materials are commercially available or earlier described in the literature.

The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, br s: broad singlet, d: doublet, t: triplet, q: quartet, m: multiplet).

Analytical in line liquid chromatography separations followed by mass spectra detections, were recorded on a Waters LCMS consisting of an Alliance 2795 (LC) and a ZQ single quadropole mass spectrometer. The mass spectrometer was equipped with an electrospray ion source operated in a positive and/or negative ion mode. The ion spray voltage was +3 kV and the mass spectrometer was scanned from m/z 100-700 at a scan time of 0.8 s. To the column, X-Terra MS, Waters, C8, 2.1×50 mm, 3.5 mm, was applied a linear gradient from 5% to 100% acetonitrile in 10 mM ammonium acetate (aq.), or in 0.1% TFA (aq.).

Preparative reversed phase chromatography was run on a Gilson preparative HPLC with UV detection at 254 nm, using a Chiralpak® AD 0.46×25 cm column (Daicel Chemical Industries, Ltd.).

Purification of products were also done using Chem Elut Extraction Columns (Varian, cat #1219-8002), Mega BE-SI (Bond Elut Silica) SPE Columns (Varian, cat #12256018; 12256026; 12256034), or by flash chromatography in silica-filled glass columns.

The pharmacological properties of the compounds of the invention can be analyzed using standard assays for functional activity. Examples of glutamate receptor assays are well known in the art as described in, for example, Aramori et al., 1992, Neuron, 8:757; Tanabe et al., 1992, Neuron, 8:169; Miller et al., 1995, J. Neuroscience, 15:6103; Balazs, et al., 1997, J. Neurochemistry, 1997, 69:151. The methodology described in these publications is incorporated herein by reference. Conveniently, the compounds of the invention can be studied by means of an assay that measures the mobilization of intracellular calcium, $[Ca^{2+}]_i$ in cells expressing mGluR2.

A [$^{35}$S]-GTPγS binding assay was used to functionally assay mGluR2 receptor activation. The allosteric activator activity of compounds at the human mGluR2 receptor were measured using a [$^{35}$S]-GTPγS binding assay with membranes prepared from CHO cells which stably express the human mGluR2. The assay is based upon the principle that agonists bind to G-protein coupled receptors to stimulate GDP-GTP exchange at the G-protein. Since [$^{35}$S]-GTPγS is a non-hydrolyzable GTP analog, it can be used to provide an index of GDP-GTP exchange and, thus, receptor activation. The GTPγS binding assay therefore provides a quantitative measure of receptor activation.

Membranes were prepared from CHO cells stably transfected with human mGluR2. Membranes (30 μg protein) were incubated with test compound (3 nM to 300 μM) for 15 minutes at room temperature prior to the addition of 1 μM glutamate, and incubated for 30 min at 30° C. in 500 μl assay buffer (20 mM HEPES, 100 mM NaCl, 10 mM $MgCl_2$), containing 30 μM GDP and 0.1 nM [$^{35}$S]-GTPγS (1250 Ci/mmol). Reactions were carried out in triplicate in 2 ml polypropylene 96-well plates. Reactions were terminated by vacuum filtration using a Packard 96-well harvester and Unifilter-96, GF/B filter microplates. The filter plates were washed 4×1.5 ml with ice-cold wash buffer (10 mM sodium phosphate buffer, pH 7.4). The filter plates were dried and 35 μl of scintillation fluid (Microscint 20) was added to each well. The amount of radioactivity bound was determined by counting plates on the Packard TopCount. Data was analyzed using GraphPad Prism, and $EC_{50}$ and $E_{max}$ values (relative to the maximum glutamate effect) were calculated using non-linear regression.

Generally, compounds of the present invention were active in the assays described herein at concentrations (or with $EC_{50}$ values) of less than about 10 μM. Preferred compounds of the invention have $EC_{50}$ values of less than 1 μM; more preferred compounds of less than about 100 nM. For example, compounds of Examples 3.1, 13.5, 10.29, 17.2 and 17.3 have $EC_{50}$ values of 1.96, 0.39, 0.12, 0.91 and 3.1 μM, respectively.

EXAMPLES

Example 1.1

5-(R)-phenyl-oxazolidin-2-one

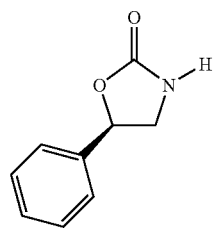

General Procedure (1): A solution of (R)-2-Amino-1-phenylethanol (0.675 g, 4.92 mmol) and di-2-pyridyl carbonate (1.06 g, 4.92 mmol) in anhydrous dichloromethane (50 ml) was stirred at RT overnight. The resultant reaction mixture was diluted with ethyl acetate (60 mL), washed with water (2×25 mL), brine (25 mL), dried over anhydrous sodium sulphate and concentrated in vacuo to get the product as a white solid. It was purified by chromatography on silica gel, eluting with 5-15% ethyl acetate in hexanes, to yield 0.695 g (87%) of the desired product as a white solid. $^1$H NMR (300 MHz, CDCl$_3$): δ 7.42 (m, 5H), 6.19 (bs, 1H) 5.64 (t, 1H), 4.0 (t, 1H), 3.56 (dd, 1H).

In a similar fashion the following compounds were synthesized. Triethyl amine was used as a base to neutralize, where the starting material (amino alcohol) was available as a salt.

| Ex. No. | Structure | Name | Form |
|---|---|---|---|
| 1.2 | 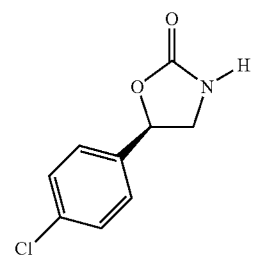 | 5-(R)-(4-Chloro-phenyl)-oxazolidin-2-one | 85 mg (95%) white solid |
| NMR | 7.35(m, 4H), 6.78(bs, 1H) 5.6(t, 1H), 3.97(t, 1H), 3.51(dd, 1H). | | |
| 1.3 | 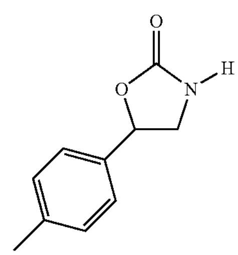 | 5-(4-Methyl-phenyl)-oxazolidin-2-one | 69 mg (99%) white solid |
| NMR | 7.28(dd, 2H), 7.219(dd, 2H), 6.79(bs, 1H) 5.8(t, 1H), 3.95(t, 1H), 3.53(dd, 1H), 2.4(s, 3H) | | |
| 1.4 | 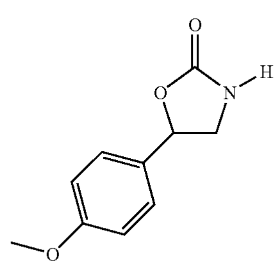 | 5-(4-Methoxy-phenyl)-oxazolidin-2-one | 74 mg (97%) white solid |
| NMR | 7.28(dd, 2H), 6.94(dd, 2H), 6.57(bs, 1H) 5.57(t, 1H), 3.94(t, 1H), 3.83(s, 3H), 3.53(dd, 1H | | |

-continued

| Ex. No. | Structure | Name | Form |
|---|---|---|---|
| 1.5 | 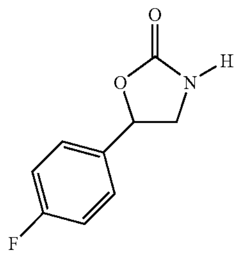 | 5-(4-Fluoro-phenyl)-oxazolidin-2-one | 907 mg 96% white solid |
| NMR | 7.39(m, 2H), 7.12(m, 2H), 5.66(bs, 1H) 5.63(t, 1H), 4(t, 1H), 3.54(dd, 1H) | | |
| 1.6 | 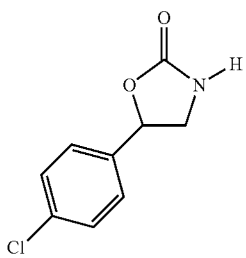 | 5-(4-Chloro-phenyl)-oxazolidm-2-one | 85 mg 95% white solid |
| NMR | 7.31(m, 4H), 6.78(bs, 1H) 5.6(t, 1H), 3.97(t, 1H), 3.51(dd, 1H). | | |
| 1.7 | 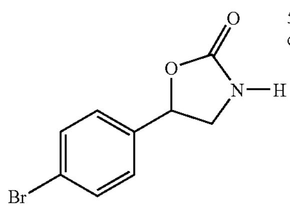 | 5-(4-Bromo-phenyl)-oxazolidin-2-one | 582 mg, 78% colourless solid |
| NMR | 7.59-7.54(d, 2H), 7.30-7.27(d, 2H), 5.61(t, 1H), 5.51(br s, 1H), 4.01(t, 1H), 3.45-3.46(m, 1H) | | |
| 1.8 | 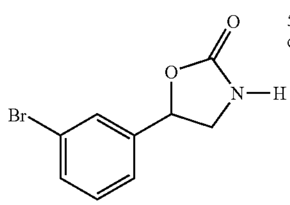 | 5-(3-Bromo-phenyl)-oxazolidin-2-one | 610 mg, 54% colourless solid |
| NMR | 7.56-7.52(m, 2H), 7.33-7.30(m, 2H), 5.79(br s, 1H), 5.61(t, 1H), 3.56(t, 1H). | | |

Example 2

5-(R)-(4-chlorophenyl)-oxazolidin-2-one

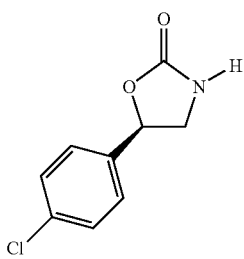

General Procedure (2): To a solution of (2R)-(4-chlorophenyl)(hydroxy)ethane nitrite (0.5 g, 2.98 mmol) in anhydrous THF (6 mL), was added BH3.THF complex (6 mL, 1M in THF, 6 mmol) drop wise at RT and refluxed for 3 h. The reaction mixture was quenched by the drop wise addition of Methanol (6 mL). After 20 min. of stirring, the reaction mixture was concentrated in vacuo to get the amino alcohol. This was dissolved in anhydrous dichloromethane (5 mL) and stirred with di-2-pyridyl carbonate (613 mg, 2.83 mmol,) at RT overnight. The resultant reaction mixture was diluted with ethyl acetate (25 mL), washed with water (2×10 mL), brine (10 mL), dried over sodium sulphate (anhydrous) and concentrated in vacuo to yield the desired product, with good purity, as a white solid (573 mg, 97% over 2 steps). $^1$H NMR (300 MHz, $CDCl_3$): δ 7.4 (m, 2H), 7.35 (m, 2H), 5.8 (bs, 5.62 (t, 1H), 4.15 (t, 1H), 3.52 (t, 1H).

5-substituted oxazolidin-2-one compounds were made by using one of the above two methods, based on the availability of the starting material. The product so obtained was used for the subsequent step without further purification.

Example 3.1

5-(R)-Phenyl-3-(4-trifluoromethoxy-benzyl)-oxazolidin-2-one

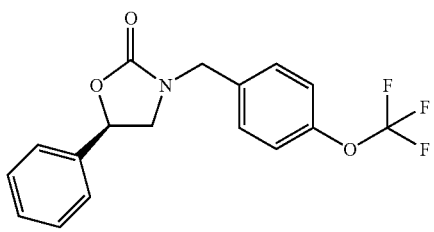

General Procedure (3): A suspension of 5-(R)-Phenyl-oxazolidin-2-one (74 mg, 0.45 mmol), 4-(trifluoro methoxy) benzyl bromide (173 mg, 0.68 mmol) and Cesium carbonate (443 mg, 1.36 mmol) in anhydrous acetonitrile (3 mL) was stirred at 70° C. for 4 h. The resulting suspension was diluted with ethyl acetate (6 mL), washed with water (3 mL), brine (3 mL), dried over anhydrous sodium sulphate and concentrated in vacuo to give the product as a pale brown oil. Purification by chromatography on silica gel using 20-25% ethyl acetate/hexanes as eluent yielded a colorless oil as the title compound (128 mg, 84%). $^1$H NMR (300 MHz, CDCl$_3$): δ 7.36 (m, 7H), 7.22 (d, 2H), 5.5 (t, 1H), 4.49 (dd, 3H), 3.8 (t, 1H), 3.34 (dd, 1H).

In a similar fashion, the following compounds were made:

| Ex. No. | Structure | Name | Form |
|---|---|---|---|
| 3.2 | 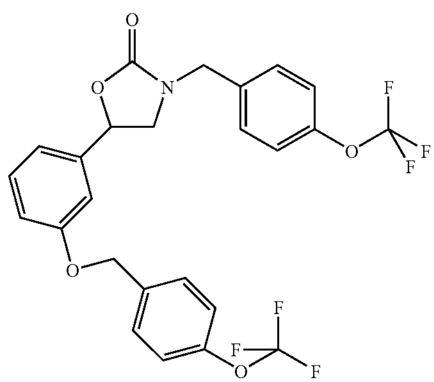 | 3-(4-Trifluoromethoxybenzyl)-5-[3-(4-trifluoromethoxy- benzyloxy) phenyl]-oxazolidin-2-one | 67 mg (33%), colorless oder |
| NMR | 7.47(d, 2H), 7.3(m, 7H), 6.95(m, 3H), 5.5(t, 1H), 5.06(s, 2H), 4.49(dd, 2H), 3.8(t, 2H), 3.32(dd, 1H). | | |
| 3.3 | 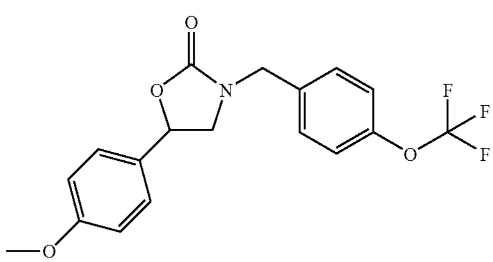 | 5-(4-Methoxy-phenyl)-3-(4-trifluoromethoxy-benzyl)-oxazolidin-2-one | 103 mg(73%) Pale yellow solid |
| NMR | 7.35(d, 2H), 7.23(m, 4H), 6.90(d, 2H), 5.45(t, 1H), 4.56(d, 1H), 4.42(d, 1H), 3.81 (s, 3H), 3.76(t, 1H), 3.33(dd, 1H). | | |
| 3.4 | 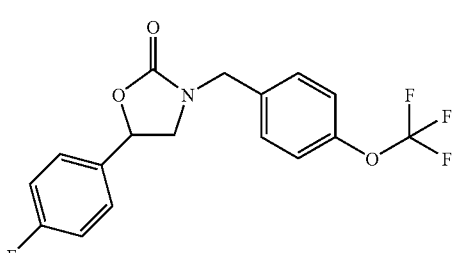 | 5-(4-Fluoro-phenyl)-3-(4-trifluoromethoxy-benzyl)-oxazolidin-2-one | 96 mg(67%) Pale yellow oil |
| NMR | 7.32(m, 4H), 7.23(m, 2H), 7.07(m, 2H), 5.48(t, 1H), 4.56(d, 1H), 4.41(d, 1H), 3.80 (t, 1H), 3.31(dd, 1H). | | |

| Ex. No. | Structure | Name | Form |
|---|---|---|---|
| 3.5 | 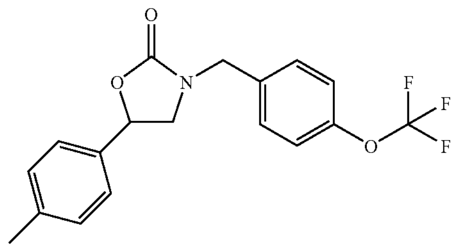 | 5-(4-Methyl-phenyl)-3-(4-trifluoromethoxy-benzyl)-oxazolidin-2-one | 108 mg, (79%) White solid |
| NMR | 7.34(dd, 2H), 7.23(m, 6H), 5.48(t, 1H), 4.58(d, 1H), 4.42(d, 1H), 3.78(t, 1H), 3.32 (dd, 1H), 2.36(s, 3H) | | |
| 3.6 | 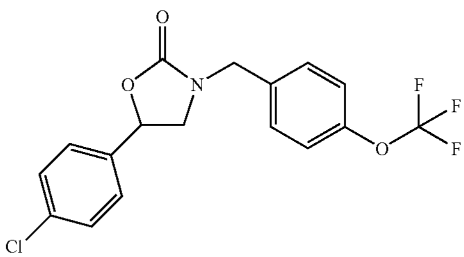 | 5-(4-Chloro-phenyl)-3-(4-trifluoromethoxybenzyl)-oxazolidin-2-one | 127 mg, 88% Colorless oil |
| NMR | 7.31(m, 8H), 5.48(t, 1H), 4.57(dd, 1H), 4.39(d, 1H), 3.80(t, 1H), 3.29(dd, 1H). | | |
| 3.7 | 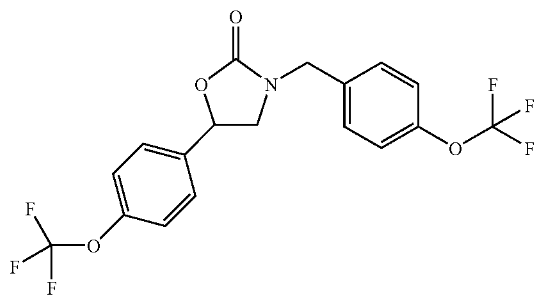 | 3-(4-Trifluoromethoxy-benzyl)-5-(4-trifluoromethoxy-phenyl)-oxazolidin-2-one | 130 mg, 80% Colorless oil |
| NMR | 7.65(d, 2H), 7.45(d, 2H), 7.33(d, 2H), 7.20(d, 2H), 5.48(t, 1H), 4~57(dd, 1H), 4.39 (d, 1H), 3.87(t, 1H), 3.30(dd, 1H). | | |
| 3.8 | 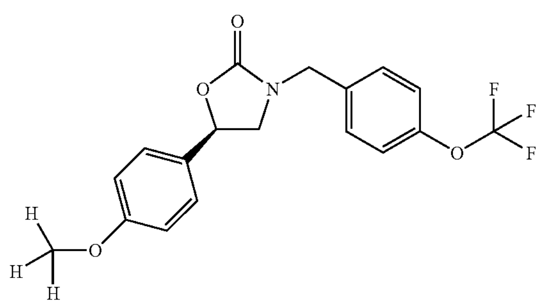 | 5-(4-Methoxyphenyl)-3-(4-trifluoromethoxy-benzyl)-oxazolidin-2-one | 142 mg, 79% Pale yellow oil |
| NMR | 7.34(d, 2H), 7.24(m, 1H), 6.91(d, 2H), 5.45(t, 1H), 4.56(dd, 1H), 4.42(d, 1H), 3.81 (s, 3H), 3.76(t, 1H), 3.33(dd, 1H). | | |
| 3.9 | 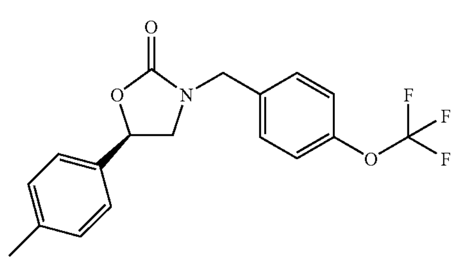 | 5-p-Tolyl-3-(4-trifluoromethoxy-benzyl)-oxazolidin-2-one | 108 mg, 99% White solid |
| NMR | 7.34(d, 2H), 7.22(m, 6H), 5.47(t, 1H), 4.54(d, 1H), 4.42(d, 1H), 3.78(t, 1H), 3.33 (t, 1H), 2.37(s, 3H). | | |

| Ex. No. | Structure | Name | Form |
|---|---|---|---|
| 3.10 | 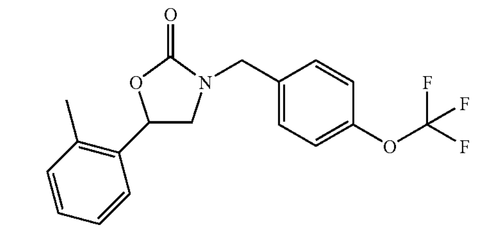 | 5-o-Tolyl-3-(4-trifluoromethoxy-benzyl)-oxazolidin-2-one | 106 mg, 64% white solid |
| NMR | 7.41(m, 1H), 7.35(d, 2H), 7.23(m, ~H), 5.7(dd, 1H), 4.56(d, 1H), 4.42(d, 1H), 3.85 (t, 1H), 3.25(dd, 1H). | | |
| 3.11 | 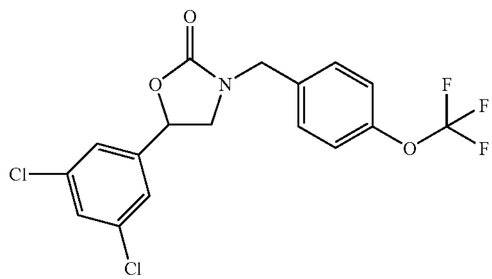 | 5-(3,5-Dichloro-phenyl)-3-(4-trifluoromethoxybenzyl)-oxazolidin-2-one | 129 mg, 75% Colorless oil |
| NMR | 7.33(m, 1H), 7.21(m, 1H), 5.45(dd, 1H), 4.56(d, 1H), 4.39(d, 1H), 3.83(t, 1H), 3.28 (dd, 1H). | | |
| 3.12 | 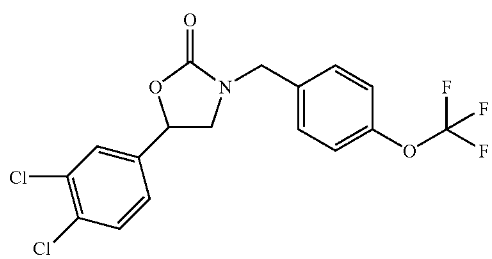 | 5-(3,4-Dichloro-phenyl)-3-(4-trifluoromethoxybenzyl)-oxazolidin-2-one | 131 mg, 63% Colorless oil |
| NMR | 7.43(m, 2H), 7.33(m, 2H), 7.20(m, 1H), 5.45(dd, 1H), 4.46(d, 1H), 4.39(d, 1H), 3.83(t, 1H), 3.28(dd, 1H). | | |
| 3.13 | 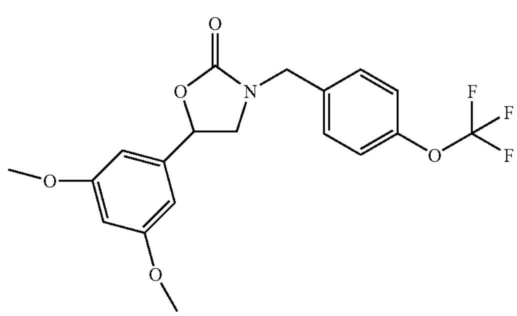 | 5-(3,5-Dimethoxy-phenyl)-3-(4-trifluoromethoxy-benzyl)-oxazolidin-2-one | 83 mg, 47% White solid |
| NMR | 7.35(dd, 2H), 7.25(dd, 2H), 6.43(m, 3H), 5.44(dd, 1H), 4.54(d, 1H), 4.41(d, 1H), 3.78(m, 7H), 3.17(dd, 1H). | | |
| 3.14 | 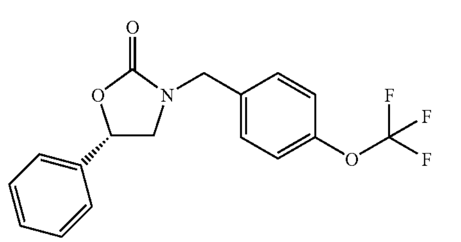 | 3-(4-trifluoro-methoxybenzyl)-5-(S)-Phenyl-oxazolidin-2-one | 57 mg, 28% white solid |
| NMR | 7.37(m, 7H), 7.21(d, 2H), 5.51(dd, 1H), 4.57(d, 1H), 4.42(d, 1H); 3.81(t, 1H), 3.34 (dd, 1H). | | |

| Ex. No. | Structure | Name | Form |
|---|---|---|---|
| 3.15 | 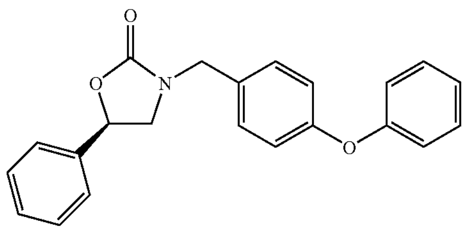 | 3-(4-phenoxy-benzyl)-5-(R)-Phenyl-oxazolidin-2-one | 27 mg, 88%<br>Brown oil |
| NMR | 7.38(m, 7H), 7.28(dd, 2H), 7.14(t, 1H), 7.02(m, 4H), 5.50(t, 1H), 4.53(d, 1H), 4.40 (d, 1H), 3.81(t, 1H), 3.34(dd, 1H). | | |
| 3.16 | 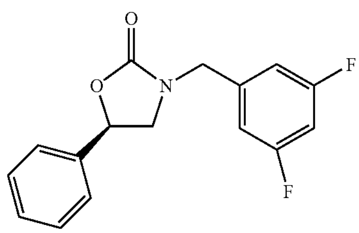 | 3-(3,5-Difluoro-benzyl)-5-(R)-phenyl-oxazolidin-2-one | 41 mg, 43%<br>White solid |
| NMR | 7.38(m, 5H), 6.83(m, 3H), 5.54(t, 1H), 4.55(d, 1H), 4.39(d, 1H), 3.84(1, 1H), 3.35 (dd, 1H). | | |
| 3.17 | 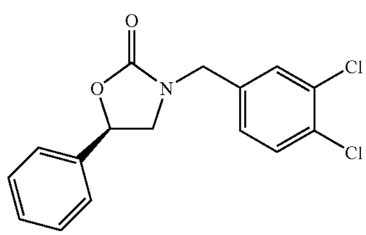 | 3-(3,4-Dichloro-benzyl)-5-(R)-phenyl)-oxazolidin-2-one | 45 mg, 57%<br>White solid |
| NMR | 7.39(m, 7H), 7.17(d, 1H), 5.52(t, 1H), 4.50(d, 1H), 4.37(d, 1H), 3.82(t, 1H), 3.33 (dd, 1H). | | |
| 3.18 | 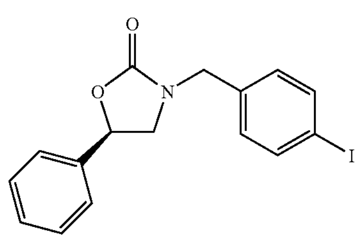 | 3-(4-Iodo-benzyl)-5-(R)-phenyl)-oxazolidin-2-one | 60 mg, 64%<br>White solid |
| NMR | 7.68(dd, 2H), 7.35(m, 5H), 7.05(d, 2H), 5.47(t, 1H), 4.49(d, 1H), 4.37(d, 1H), 3.78 (t, 1H), 3.31(dd, 1H). | | |
| 3.19 | 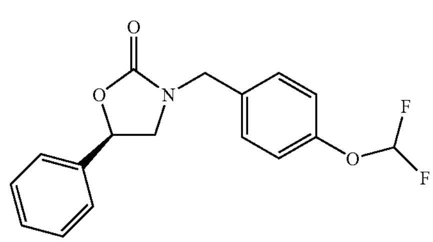 | 3-(4-Difluoromethoxy-benzyl)-5-(R)-phenyl)-oxazolidin-2-one | 39 mg, 52%<br>Colorless oil |
| NMR | 7.34(m, 7H), 7.12(d, 2H), 6.53(t, 1H), 5.50(t, 1H), 4.55(d, 1H), 4.40(d, 1H), 3.80 (t, 1H), 3.32(dd, 1H). | | |

-continued

| Ex. No. | Structure | Name | Form |
|---|---|---|---|
| 3.20 | 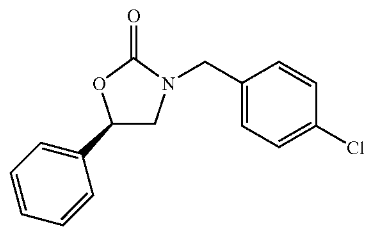 | 3-(4-Chloro-benzyl)-5-(R)-phenyl-oxazolidin-2-one | 60 mg, 64% White solid |
| NMR | 7.37(m, 1H), 5.51(t, 1H), 4.53(d, 1H), 4.40(d, 1H), 3.79(t, 1H), 3.32(dd, 1H). | | |
| 3.21 | 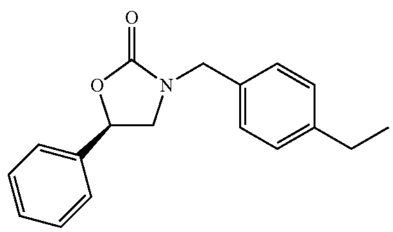 | 3-(4-Ethyl-benzyl)-5-(R)-phenyl-oxazolidin-2-one | 69 mg, 75% Off white solid |
| NMR | 7.33(m, 9H), 5.47(dd, 1H), 4.58(d, 1H), 4.39(d, 1H), 3.79(t, 1H), 3.32(dd, 1H), 2.66(g, 2H), 1.26(t, 3H) | | |
| 3.22 | 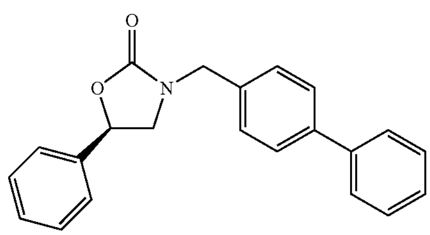 | 3-Biphenyl-4-ylmethyl-5-(R)-phenyl)-oxazolidin-2-one | 52 mg, 64% White solid |
| NMR | 7.60(m, 4H), 7.40(m, 10H), 5.52(t, 1H), 4.62(d, 1H), 4.48(d, 1H), 3.84(t, 1H), 3.38 (dd, 1H). | | |
| 3.23 | 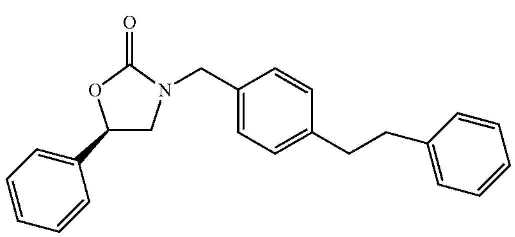 | 3-(4-Benzyloxy-benzyl)-5-(R)-phenyl)-oxazolidin-2-one | 61 mg, 69% White solid |
| NMR | 7.25(m, 12H), 6.98(d, 2H), 5.47(t, 1H), 5.08(s, 2H), 4.50(d, 1H), 4.37(d, 1H), 3.77 (t, 1H), 3.31(dd, 1H). | | |
| 3.24 | 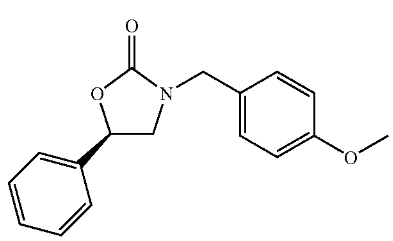 | 3-(4-Methoxy-benzyl)-5-(R)-phenyl-oxazolidin-2-one | 344 mg, 99% Colorless oil |
| NMR | 7.32(m, 7H), 7.89(d, 2H), 5.48(dd, 1H), 4.50(d, 1H), 4.36(d, 1H), 3.83(s, 3H), 3.77 (t, 1H), 3.30(dd, 1H). | | |

-continued

| Ex. No. | Structure | Name | Form |
|---|---|---|---|
| 3.25 | 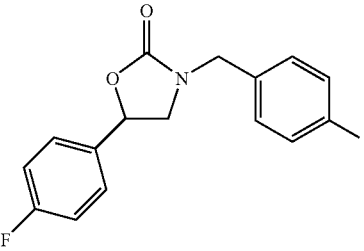 | 5-(4-Fluoro-phenyl)-3-(4-Iodo-benzyl)-oxazolidin-2-one | 2.5 g, 98%<br>Off white solid |
| NMR | 7.66(m, 2H), 7.28(m, 2H), 7.05(m, 4H), 5.45(t, 1H), 4.46(d, 1H), 4.35(d, 1H), 3.76 (t, 1H), 3.27(dd, 1H). | | |
| 3.26 | 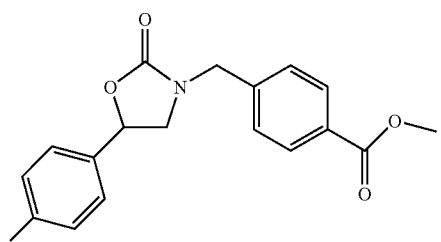 | 4-5[-(4-Fluoro-phenyl)-2-oxo-oxazolidin-3-ylmethyl]-benzoic acid methyl ester | 124 mg, 46%<br>White solid |
| NMR | 8.02(m, 2H), 7.35(d, 2H), 7.29(m, 2H), 7.05(m, 2H), 5.48(t, 1H), 4.58(d, 1H), 4.47 (d, 1H), 3.91(s, 3H), 3.79(t, 1H), 3.29 dd, 1H). | | |
| 3.27 | 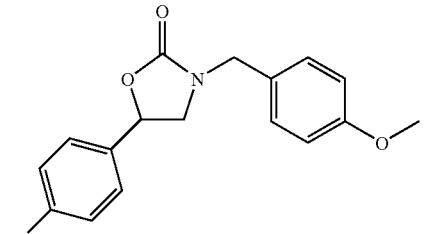 | 5-(4-Fluoro-phenyl)-3-(4-methoxy-benzyl)-oxazolidin-2-one | 510 mg, 77%<br>Colorless oil |
| NMR | 7.30(m, 4H), 7.08(m, 2H), 6.89(m, 2H), 5.45(t, 1H), 4.50(d, 1H), 4.37(d, 1H), 3.83 (s, 3H), 3.76(t, 1H), 3.27(dd, 1H). | | |
| 3.28 | 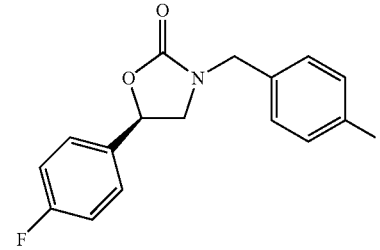 | 5-(R)-(4-Chloro-phenyl)-3-(4-Iodo-benzyl)-oxazolidin-2-one | 186 mg, 90%<br>White solid |
| NMR | 7.70(m, 2H), 7.37(m, 2H), 7.26(m, 2H), 7.04(m, 2H), 5.48(t, 1H), 4.50(d, 1H), 4.37(d, 1H), 3.78(t, 1H), 3.27(dd, 1H). | | |
| 3.29 | 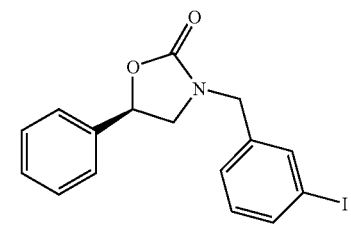 | 3-(3-Iodo-benzyl)-5-(R)-phenyl-oxazolidin-2-one | 786 mg, 100%<br>yellow oil |
| NMR | 7.66(d, 2H), 7.41-7.27(m, 6H), 7.12(t, 1H), 5.52(t, 1H), 4.52(d, 1H), 4.37(d, 1H), 3.81(t, 1H), 3.33(t, 3H) | | |

| Ex. No. | Structure | Name | Form |
|---|---|---|---|
| 3.30 | 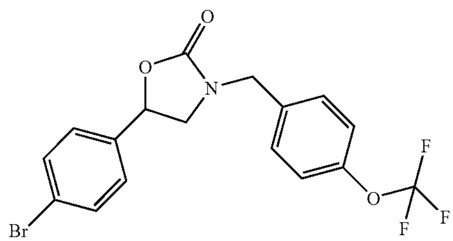 | 5-(4-Bromo-phenyl)-3-(4-trifluoromethoxy-benzyl)-oxazotidin-2-one | 374 mg, 96% colourless oil |
| NMR | 7.52(d, 2H), 7.33(d, 2H), 7.23-7.18(m, 4H), 5.47(t, 1H), 4.57(d, 1H), 4.41(d, 1H), 3.81(t, 1H), 3.29(t, 1H) | | |
| 3.31 | 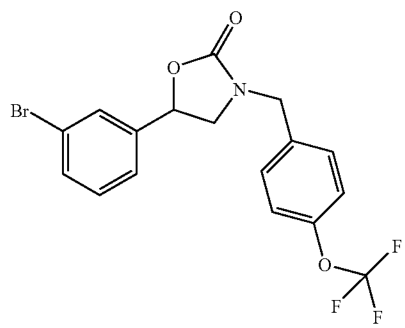 | 5-(3-Bromo-phenyl)-3-(4-trifluoromethoxy-benzyl)-oxazolidin-2-one | 424 mg, 99% yellow oil |
| NMR | 7.50-7.48(m, 2H), 7.34(d, 2H), 7.27-7.20(m, 4H), 5.47(t, 1H), 4.57(d, 1H), 4.41(d, 1h), 3.82(t, 1H), 3.30(t, 1H). | | |
| 3.32 | 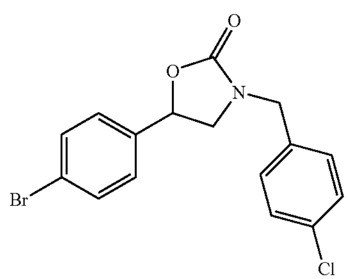 | 5-(4-Bromo-phenyl)-3-(4-chloro-benzyl)-oxazolidin-2-one | 139 mg, 73% colourless oil |
| NMR | 7.51(d, 2H), 7.32(d, 2H), 7.23-7.14(m, 4H), 5.45(t, 1H), 5.48(d, 1H), 4.38(d, 1H), 3.76(t, 1H), 3.25(t, 1H). | | |

Example 4

3-(4-hydroxy-benzyl)-5-(R)-phenyl-oxazolidin-2-one

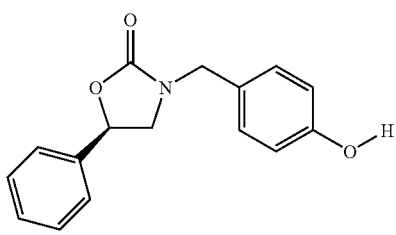

To a solution of 3-(4-Methoxy-benzyl)-5-(R)-phenyl-oxazolidin-2-one (60 mg, 0.21 mmol, prepared according to procedure 3) in dichloromethane (2 mL) at −78° C., was added BBr$_3$ (1M in dichloromethane) drop wise and the reaction mixture was allowed to warm up slowly to RT. After 1.5 h of stirring, the reaction mixture was quenched with saturated aqueous sodium bicarbonate solution and extracted with dichloromethane (3×4 mL). The combined organic phase was dried over anhydrous sodium sulfate and concentrated in vacuo to get the product. Purification by chromatography on silica gel, eluting with 1-2% methanol in dichloromethane yielded the title compound (32 mg, 56%) as a white powder. $^1$H NMR (300 MHz, CDCl$_3$): 7.34 (m, 5H), 7.18 (d, 2H), 6.83 (m, 2H), 5.48 (t, 1H), 5.12 (bs, 1H), 4.50 (d, 1H), 4.36 (d, 1H), 3.78 (t, 1H), 3.31 (dd, 1H).

Example 5.1

5-(4-fluoro-phenyl-3-[4-(4-pyridin-2-yl-piperazine-1-carbonyl)-benzyl]-oxazolidin-2-one

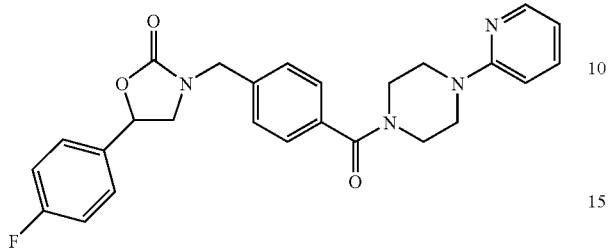

The carboxylic acid (35 mg, 111 mmol) obtained by the hydrolysis of 4-[5-(4-Fluoro-phenyl)-2-oxo-oxazolidin-3-yl methyl]-benzoic acid methyl ester was coupled with the 1-pyridin-2-yl-piperazine (1.1 eq.) using EDCI (1.1 eq) and HOBT (1.1 eq) in DMF (1 mL) at RT, overnight. The reaction mixture was diluted with dichloromethane (7 mL), washed with water (3 mL), aq. saturated sodium bicarbonate solution (3 mL), brine (3 mL), dried over anhydrous sodium sulphate and concentrated in vacuo to get the product. It was purified by chromatography on silica gel, eluting with dichloromethane containing 1-3% 2M ammonic in methanol, to yield the desired product as white powder (47 mg, 93%). $^1$H NMR (300 MHz, CDCl$_3$): δ 8.22 (d, 1H), 7.54 (m, 1H), 7.46 (d, 2H), 7.32 (m, 4H), 7.10 (t, 2H), 6.69 (m, 2H), 5.50 (t, 1H), 4.62 (d, 1H), 4.47 (d, 1H), 3.90 (bs, 2H), 3.80 (t, 1H), 3.58 (bs, 6H), 3.32 (dd, 1H).

In a similar fashion the following compounds were synthesized:

Example 6.1

3-(4-bromomethyl-benzyl)-5-(R)-phenyl-oxazolidin-2-one

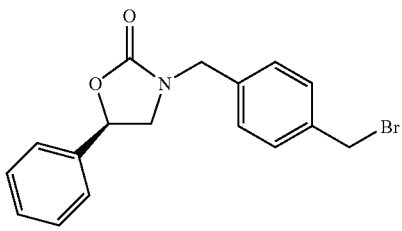

General Procedure (4): A suspension of 5-(R)-Phenyl-oxazolidin-2-one (400 mg, 2.45 mmol), α,α-dibromo-p-xylene (5.1 g, 19.6 mmol) and Cesium carbonate (2.4 g, 7.35 mmol) in anhydrous acetonitrile (200 mL) was heated with at 70° C. for 4 h. The solid was filtered off and the filtrate was concentrated in vacuo. The residue was taken up in dichloromethane (35 mL), washed with water (10 mL), brine (10 mL), dried over anhydrous sodium sulphate and concentrated in vacuo to get the product. Purification of the product by chromatography on silica gel, eluting with 5-30% ethyl acetate/hexanes, yielded the title compound (595 mg, 70%). $^1$H NMR (300 MHz, CDCl$_3$): δ 7.38 (m, 9H), 5.51 (t, 1H), 4.58 (d, 1H), 4.51 (s, 2H), 4.41 (d, 1H), 3.80 (t, 1H), 3.3 (dd, 1H).

| Ex. No. | Structure | Name | Form |
|---|---|---|---|
| 5.2 | 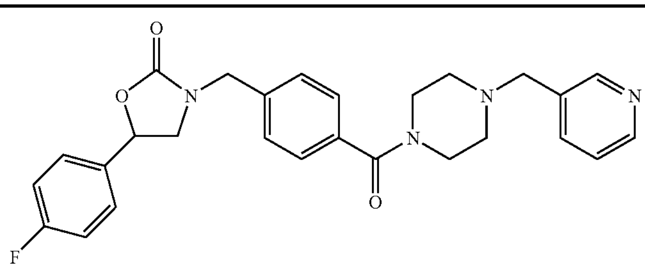 | 5-(4-Fluoro-phenyl)-3[4-(4-pyridin-3-ylmethyl-piperazine-1-carbonyl)-benzyl]-oxazolidin-2-one | 51 mg, 97%. White solid. |
| NMR | 8.53(m, 2H), 7.65(m, 1H), 7.33(m, 7H), 7.06(t, 2H), 5.46(t, 1H), 4.56(d, 1H), 4.42 (d, 1H), 3.76(m, 3H), 3.55(s, 2H), 3.41(bs, 2H), 3.28(dd, 1H), 2.53(bs, 2H), 2.39 (bs, 2H). | | |
| 53 | 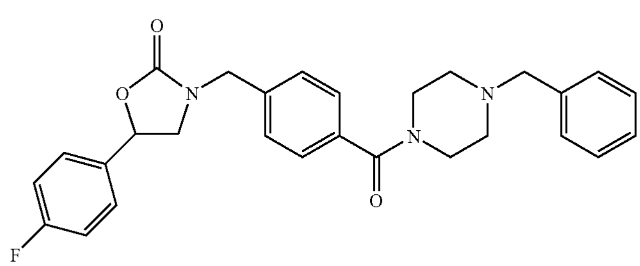 | 3-[4-(4-Benzyl-piperazine-1-carbonyl)-benzyl]-5-(4-fluoro-phenyl)-oxazolidin-2-one | 49 mg, 93% White solid |
| NMR | 7.34(m, 11H), 7.08(m, 2H), 5.47(t, 1H), 4.57(d, 1H), 4.43(d, 1H), 3.77(m, 3H), 3.55(s, 2H), 3.32(bs, 2H), 3.29(dd, 1H), 2.54(bs, 2H), 2.39(bs, 2H). | | |

The following compounds were made in a similar manner:

| Ex. No. | Structure | Name | Form |
|---|---|---|---|
| 6.2 | 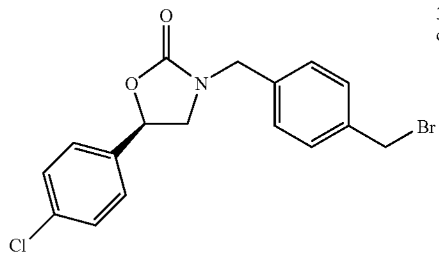 | 3-(4-Bromomethylbenzyl)-5-(R)-(4-chlorophenyl)-oxazolidin-2-one | 69 mg, 39%, white solid |
| NMR | 7.40(m, 4H), 7.26(m, 4H), 5.47(t, 1H), 4.55(d, 1H), 4.52(s, 2H), 4.40(d, 1H), 3.79 (t, 1H), 3.28(dd, 1H). | | |
| 6.3 | 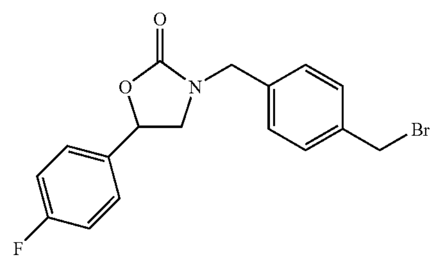 | 3-(4-bromomethylbenzyl)-5-(4-fluorophenyl)-oxazolidin-2-one | 212 mg, 53%, white powder |
| NMR | 7.39(m, 4H), 7.30(m, 4H), 7.08(m, 2H), 5.48(t, 1H), 4.56(d, 1H), 4.49(s, 2H), 4.41 (d, 1H), 3.79(t, 1H), 3.29(dd, 1H). | | |

Example 7.1

3-(morpholin-4-ylmethyl-benzyl)-5-(R)-phenyl-oxazolidin-2-one

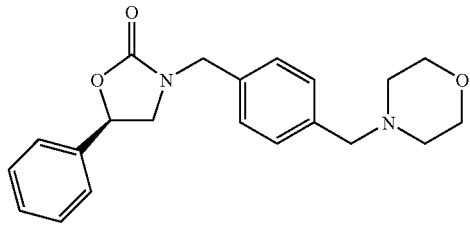

A solution of 3-(4-bromomethyl-benzyl)-5-(R)-phenyl-oxazolidin-2-one (30 mg, 0.086 mmol) and morpholine (0.038 mL, 0.433 mmol) in acetonitrile (2 mL) was heated at 70° C. for 4 hours. The reaction mixture was diluted with ethyl acetate (6 mL), washed with water (4 mL), brine (4 mL), dried over anhydrous sodium sulfate and concentrated to get the product. It was purified by chromatography on silica gel, eluting with 30-60% ethyl acetate in hexanes, to yield the title compound as a white solid (21 mg, 69%).

Note: where N-Boc protected precursors were prepared, the final free base was obtained by cleaving off the Boc protection using trifluoro acetic acid in dichloromethane. $^1$H NMR (300 MHz, CDCl$_3$): δ 7.37 (m, 9H), 5.49 (t, 1H), 4.56 (d, 1H), 4.41 (d, 2H), 3.79 (t, 1H), 3.72 (m, 4H), 3.50 (s, 2H), 3.33 (dd, 1H), 2.45 (m, 4H).

The following compounds were made in a similar fashion:

| Ex. No. | Structure | Name | Form |
|---|---|---|---|
| 7.2 | 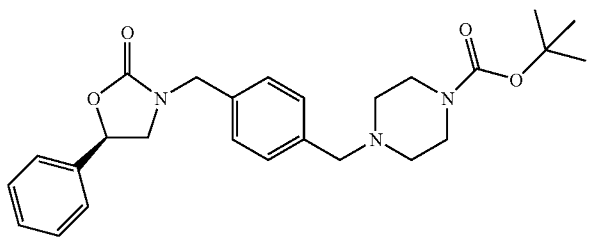 | 4-[4-(2-Oxo-5-(R)-phenyl-oxazolidin-3-ylmethyl)-benzyl]-piperazine-1-carboxylic acid tert-butyl-ester | 28 mg, 72% White solid |
| NMR | 7.37(m, 9H), 5.49(t, 1H), 4.56(d, 1H), 4.40(d, 1H), 3.79(t, 1H), 3.50(s, 2H), 3.44(m, 4H), 3.33(dd, 1H), 2.38(m, 4H), 1.47(s, 9H). | | |

| Ex. No. | Structure | Name | Form |
|---|---|---|---|
| 7.3 | 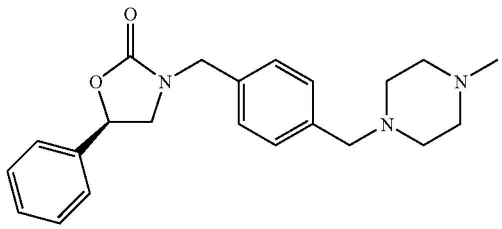 | 3-[4-(4-Methyl-piperazin-1-yhnethyl)-benzyl]-5-(R)-phenyl-oxazolidin-2-one | 28 mg, 88% White solid |
| NMR | 7.37(m, 9H), 5.49(t, 1H), 4.56(d, 1H), 4.40(d, 1H), 3.78(t, 1H), 3.51(s, 2H), 3.32(dd, 1H), 2.48(m, 8H), 2.31(s, 3H). | | |
| 7.4 | 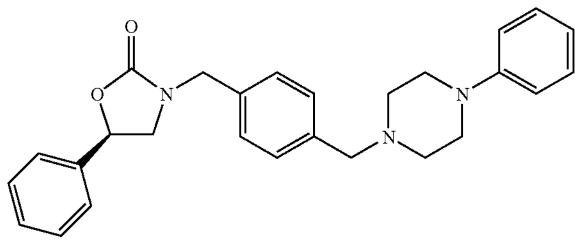 | 5-(R)-Phenyl-3-[4-(4-phenyl-piperazin-1-ylmethyl)-benyl]-oxazolidin-2-one | 37 mg, quantitative yield. White solid |
| NMR | 7.36(m, 11H), 6.96(m, 3H), 5.50(t, 1H), 4.57(d, 1H), 4.42(d, 1H), 3.80(t, 1H), 3.58(s, 2H), 3.34(dd, 1H), 3.22(m, 4H), 2.62(m, 4H). | | |
| 7.5 | 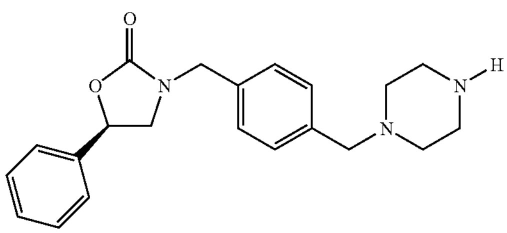 | 5-(R)-Phenyl-3-(4-piperazin-1-ylmethyl-benzyl)-oxazolidin-2-one | 28 mg, 88% White solid |
| NMR | 7.37(m, 9H), 5.49(t, 1H), 4.56(d, 1H), 4.40(d, 1H), 3.79(t, 1H), 3.49(s, 2H), 3.32(dd, 1H), 2.90(m, 4H), 2.42(bs, 4H). | | |
| 7.6 | 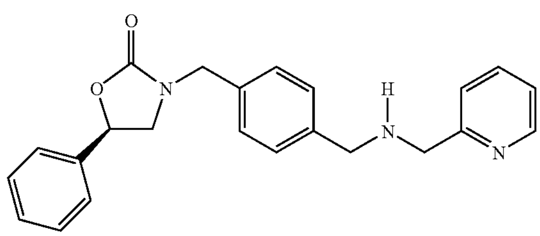 | 5-(R)-Phenyl-3-(4-{[(pyridine-2-yl methyl)-amino]-methyl}-benzyl)-oxazolidin-2-one | 36 mg, 83% Pale yellow oil. |
| NMR | 8.57(d, 1H), 7.65(m, 1H), 7.37(m, 10H), 7.27(m, 1H), 5.48(t, 1H), 4.55(d, 1H), 4.40(d, 1H), 3.93(s, 2H), 3.84(s, 2H), 3.78(t, 1H), 3.31(dd, 1H), 2.18(bs, 1H). | | |
| 7.7 | 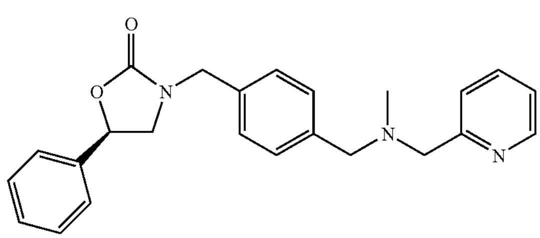 | 3-{4-[(Methyl-pyridin-2-ylmethyl-amino)-methyl]-benzyl}-5-(R)-phenyl-oxazolidine-2-one | 27 mg, 61% Colorless oil. |
| NMR | 8.54(d, 1H), 7.67(m, 1H), 7.53(d, 1H), 7.37(m, 9H), 7.17(m, 1H), 5.48(t, 1H), 4.55(d, 1H), 4.39(d, 1H), 3.78(t, 1H), 3.69(s, 2H), 3.59(s, 2H), 3.31(dd, 1H), 2.25(s, 3H). | | |

Example 8.1

5-(R)-phenyl-3-[4-(pyridine-3-yloxymethyl)-benzyl]-oxazolidin-2-one

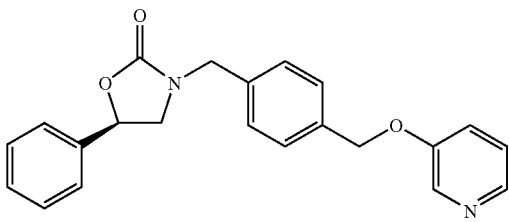

A solution of 3-hydroxypyridine (23 mg, 0.24 mmol) in DMF (1 mL) was added to a suspension of 3-(4-bromomethyl-benzyl)-5-(R)-phenyl-oxazolidin-2-one (70 mg, 0.20 mmol) (synthesized according to procedure 4) and sodium hydride (60%) (9 mg, 0.22 mmol) in DMF (1.5 mL) and the reaction mixture was stirred overnight at RT. It was diluted with dichloromethane (6 mL), washed with water (2×5 mL), dried over anhydrous sodium sulfate and concentrated in vacuo. The product was purified by chromatography on silica gel, eluting with dichloromethane containing 0.25-1% of methyl alcohol, to yield the title compound as a white solid (33 mg, 45%). $^1$H NMR (300 MHz, CDCl$_3$): δ 8.40 (s, 1H), 8.25 (s, 1H), 7.38 (m, 1H), 5.50 (dd, 1H), 5.11 (s, 2H), 4.59 (d, 1H), 4.43 (d, 1H), 3.80 (t, 1H), 3.34 (dd, 1H).

The following compounds were made in a similar fashion:

| Ex. No. | Structure | Name | Form |
|---|---|---|---|
| 8.2 | 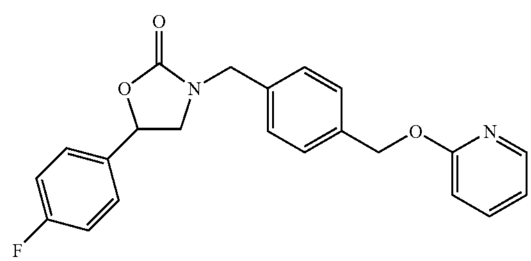 | 5-(4-Fluoro-phenyl)-3-[4-(pyridine-2-yloxymethyl)-benzyl]-oxazolidin-2-one | 38 mg, 73%. White solid. |
| NMR | 7.30(m, 8H), 7.07(m, 2H), 6.64(m, 1H), 6.19(t, 1H), 5.45(t, 1H), 5.14(s, 2H), 4.55 (d, 1H), 4.38(d, 1H), 3.76(t, 1H), 3.28(dd, 1H). | | |
| 8.3 | 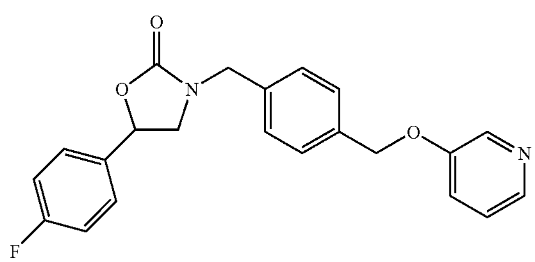 | {5-(4-Fluoro-phenyl)-3-[4-(pyridine-3-yloxylnethyl)-benzyl]-oxazolidin-2-one | 25 mg, 48%. White solid. |
| NMR | 8.40(d, 1H), 8.25(d, 1H), 7.45(d, 2H), 7.27(m, 6H), 7.08(t, 2H), 5.48(t, 1H), 5.18(s, 2H), 4.58(d, 1H), 4.44(d, 1H), 3.79(t, 1H), 3.31(dd, 1H). | | |
| 8.4 | 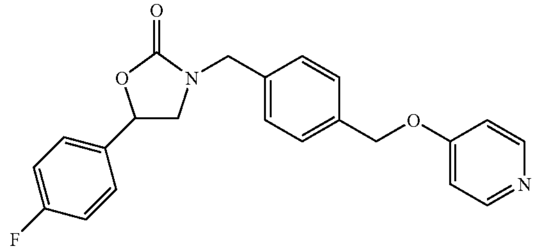 | 5-(4-Fluoro-phenyl)-3-[4-(pyridine-4-yloxymethyl)-benzyl]-oxazolidin-2-one | 20 mg, 39%. White solid. |
| NMR | 7.33(m, 6H), 7.19(d, 2H), 7.08(m, 2H), 6.40(m, 2H), 5.49(t, 1H), 4.95(s, 2H), 4.58 (d, 1H), 4.41(d, 1H), 3.79(t, 1H), 3.31(dd, 1H). | | |

-continued

| Ex. No. | Structure | Name | Form |
|---|---|---|---|
| 8.5 | 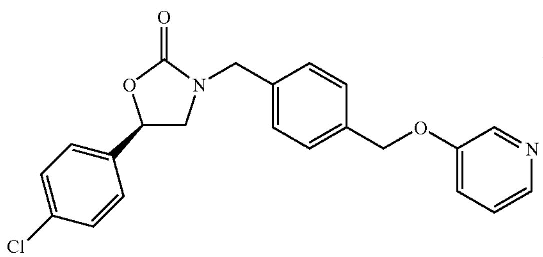 | 5-(R)-(4-Chloro-phenyl)-3-[4-(pyridine-3-yloxylmethyl)-benzyl]-oxazolidin-2-one | 12 mg, 17%. White solid. |
| NMR | 8.40(d, 1H), 8.26(m, 1H), 7.28(m, 10H), 5.46(t, 1H), 5.12(s, 2H), 4.56(d, 1H), 4.43 (d, 1H), 3.80(t, 1H), 3.29(dd, 1H). | | |

Example 9

3-(4-phenoxymethyl-benzyl)-5-(R)-phenyl-oxazolidin-2-one

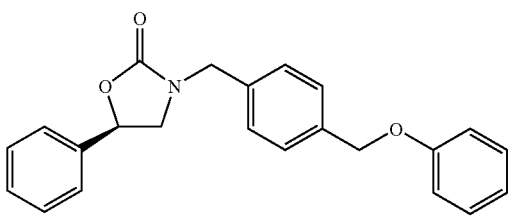

A suspension of 3-(4-bromomethyl-benzyl)-5-(R)-phenyl-oxazolidin-2-one (30 mg, 0.086 mmol, prepared according to procedure 4), phenol (10 mg, 0.1 mmol), potassium carbonate (25 mg, 0.18 mmol), potassium iodide (3 mg, 0.008 mmol) and 2-butanone was heated at 80° C. overnight. The reaction mixture was allowed to cool down to RT, mixed with water (5 mL), organic phase was separated and the aq. phase was extracted with ethyl acetate (3×8 mL). The combined organic phase was washed with brine (5 mL), dried over anhydrous sodium sulfate and concentrated in vacuo to get the product. Purification by chromatography on silica gel, eluting with 5-20% ethyl acetate in hexanes yielded the title compound (22 mg, 59%) as a white solid. $^1$H NMR (300 MHz, CDCl$_3$): δ 7.38 (m, 11H), 6.99 (m, 3H), 5.50 (t, 1H), 5.08 (s, 2H), 4.59 (d, 1H), 4.44 (d, 1H), 3.80 (m, 1H), 3.34 (m, 1H).

Example 10.1

5-(R)-Phenyl-3-(4-Pyridin-4-yl-benzyl)-oxazolidin-2-one

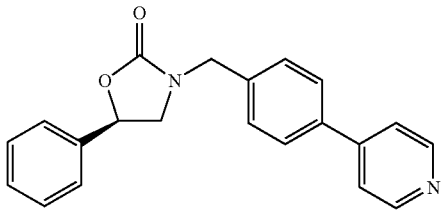

General Procedure (5): To a solution of 3-(4-Iodo-benzyl)-5-(R)-phenyl-oxazolidin-2-one (30 mg, 79 mmol) and 4-(4,4,5,5-tetramethyl-[1,3,2]dioxaborolan-2-yl)-pyridine (24 mg, 118 mmol) in dimethoxy ethane (1 mL), was added 2M aq. sodium carbonate solution (1 mL) and tetrakis(triphenyl phosphine)palladium(0). The reaction mixture was heated at 100-110° C. for 1.5 h. It was then cooled to room temperature, diluted with dichloromethane (6 mL), washed with water (2×3 mL), brine (3 mL), dried over anhydrous sodium sulphate and concentrated in vacuo to yield the product, which was purified by chromatography on silica gel, eluting with either hexane/ethyl acetate solvent system or dichloromethane/ammonia in methanol solvent system to yield the desired product as an off white solid. (13.5 mg, 52%). Note: where N-Boc protected precursors were prepared, the final free base was obtained by cleaving off the Boc protection using trifluoro acetic acid in dichloromethane. $^1$H NMR (300 MHz, CDCl$_3$): δ 8.67 (m, 2H), 7.66 (m, 2H), 7.45 (m, 9H), 5.53 (t, 1H), 4.63 (d, 1H), 4.50 (d, 1H), 3.84 (t, 1H), 3.38 (t, 1H).

In a similar fashion the following compounds were synthesized:

| Ex. No. | Structure | Name | Form |
|---|---|---|---|
| 10.2 | 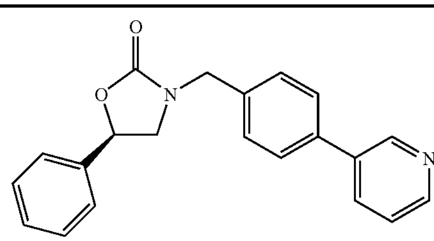 | 5-(R)-Phenyl-3-(4-Pyridin-3-yl-benzyl)-oxazolidin-2-one | 14 mg, 54% Waxy solid |
| NMR | 8.85(m, 1H), 8.62(d, 1H), 7.90(d, 1H), 7.59(d, 1H), 7.38(m, 8H), 5.53(t, 1H), 4.63 (d, 1H), 4.49(d, 1H), 3.85(t, 1H), 3.38(t, 1H). | | |

| Ex. No. | Structure | Name | Form |
|---|---|---|---|
| 10.3 | 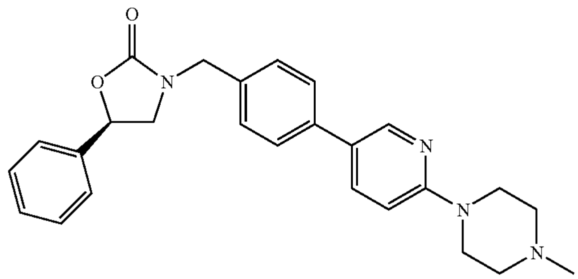 | 3-{4-[6-(4-methyl-piperazin-1-yl)-pyridin-3-yl]-benzyl}-5-(R)-phenyl-oxazolidin-2-one | 22 mg, 49% Off white solid |
| NMR | 8.44(d, 1H), 7.71(m, 1H), 7.51(d, 1H), 7.36(m, 7H), 6.73(d, 1H), 5.49(t, 1H), 4.59 (d, 1H), 4.43(d, 1H), 3.81(t, 1H), 3.63(m, 4H), 3.35(dd, 1H), 2.55(m, 4H), 2.37(s, 3H). | | |
| 10.4 | 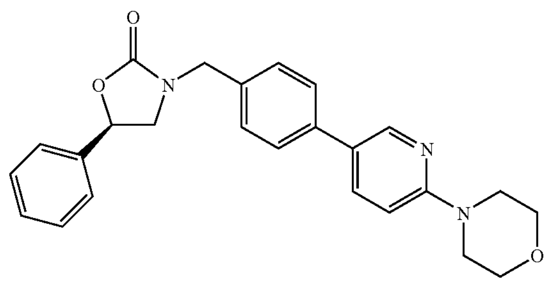 | 3-[4-(6-Morpholin-4-yl-pyridin-3-yl)-benzyl]-5-(R)-phenyl-oxazolidin-2-one | 28 mg, 64% White solid |
| NMR | 8.46(d, 1H), 7.74(dd, 1H), 7.51(d, 1H), 7.37(m, 7H), 6.73(d, 1H), 5.51(t, 1H), 4.60 (d, 1H), 4.45(d, 1H), 3.83(m, 5H), 3.57(m, 4H), 3.36(t, 1H). | | |
| 10.5 | 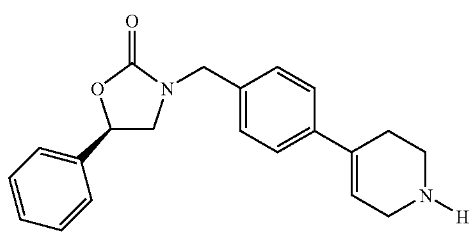 | 5-(R)-Phenyl-3-[4-(1,2,3,6-tetrahydro-pyridin-4-yl)-benzyl]-oxazolidin-2-one | 24 mg, 40% White solid |
| NMR | 7.35(m, 9H), 6.16(m, 1H), 5.49(t, 1H), 4.55(d, 1H), 4.40(d, 1H), 3.78(t, 1H), 3.55 (m, 2H), 3.32(dd, 1H), 3.12(t, 2H), 2.46(m, 2H), 1.88(bs, 1H). | | |
| 10.6 | 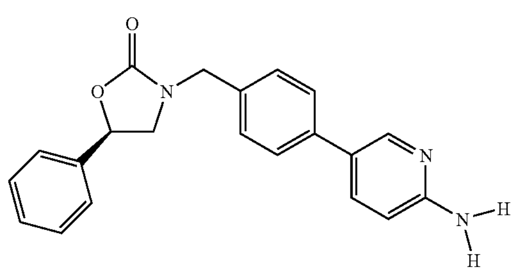 | 3-[4-(6-Amino-pyridin-3-yl)-benzyl]-5-(R)-phenyl-oxazolidin-2-one | 21 mg, 58% Off white solid |
| NMR | 8.33(m, 1H), 7.68(m, 1H), 7.50(m, 2H), 7.38(m, 7H), 6.60(m, 1H), 5.52(t, 1H), 4.61(d, 1H), 4.53(bs, 2H), 4.45(d, 1H), 3.83(t, 1H), 3.36(dd, 1H). | | |
| 10.7 | 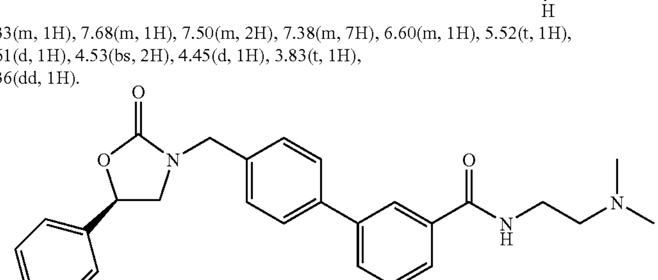 | 4'-(2-Oxo-5-(R)-phenyl-oxazolidin-3-ylmethyl) biphenyl-3-carboxylic acid(2-dimethylamino-ethyl)-amide | 33 mg, 71% White solid |
| NMR | 8.05(s, 1H), 7.34(m, 2H), 7.63(m, 2H), 7.52(t, 1H), 7.36(m, 7H), 6.90(bs, 1H), 5.53 (t, 1H), 4.63(d, 1H), 4.48(d, 1H), 3.85(t, 1H), 3.56(m, 2H), 3.38(t, 1H), 2.56(t, 2H), 2.30(s, 6H). | | |

| Ex. No. | Structure | Name | Form |
|---|---|---|---|
| 10.8 | 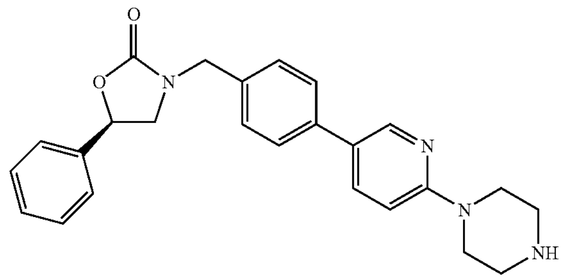 | 5-(R)-Phenyl-3-[4-(6-piperazin-1-yl-pyridin-3-yl)-benzyl]-oxazolidin-2-one | 32 mg, 74% Off white solid |
| NMR | 8.44(d, 1H), 7.71(m, 1H), 7.51(m, 2H), 7.37(m, 8H), 6.72(d, 1H), 5.50(t, 1H), 4.60 (d, 1H), 4.43(d, 1H), 3.82(t, 1H), 3.57(m, 4H), 3.35(dd, 1H), 3.02(m, 4H). | | |
| 10.9 | 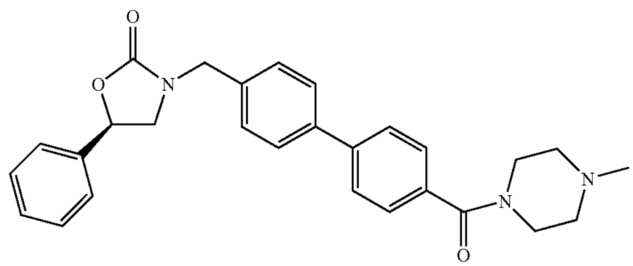 | 3-[4'-(4-Methyl-piperazine-1-carbonyl)-biphenyl-4-ylmethyl]-5-(R)-phenyl-oxazolidin-2-one | 31 mg, 65% White solid |
| NMR | 7.61(m, 4H), 7.51(m, 2H), 7.38(m, 8H), 5.53(t, 1H), 4.63(d, 1H), 4.48(d, 1H), 3.85(m, 3H), 3.53(m, 2H), 3.38(dd, 1H), 2.45(m, 4H), 2.36(s, 3H). | | |
| 10.10 | 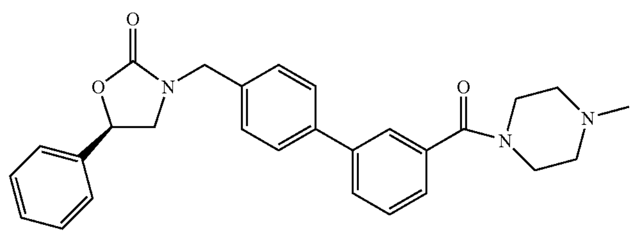 | 3-[3'-(4-Methyl-piperazine-1-carbonyl)-biphenyl-4-ylmetbyl]-5-(R)-phenyl-oxazolidin-2-one | 34 mg, 71% White solid |
| NMR | 7.61(m, 4H), 7.40(m, 1H), 7.38(m, 9H), 5.53(t, 1H), 4.60(d, 1H), 4.48(d, 1H), 3.84(m, 3H), 3.50(m, 2H), 3.37(dd, 1H), 2.52(m, 2H), 2.35(s, 5H). | | |
| 10.11 | 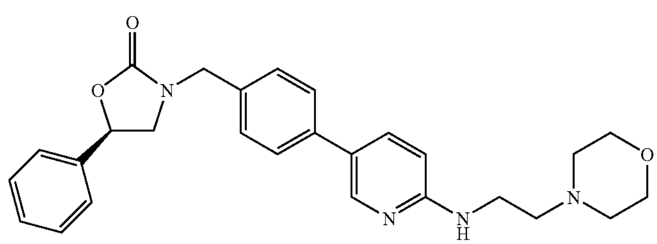 | 3-{4-[6-(2-Morpholin-4-yl-ethylamino)-pyridin-3-yl]-benzyl}-5-(R)-phenyl-oxazolidin-2-one | 26 mg, 54% White solid |
| NMR | 8.36(d, 1H), 7.66(m, 1H), 7.50(m, 2H), 7.37(m, 7H), 6.50(m, 1H), 5.52(t, 1H), 5.21 (m, 1H), 4.60(d, 1H), 4.45(d, 1H), 3.83(t, 1H), 3.76(m, 4H), 3.39(m, 3H), 2.67(t, 2H), 2.53(m, 4H). | | |
| 10.12 | 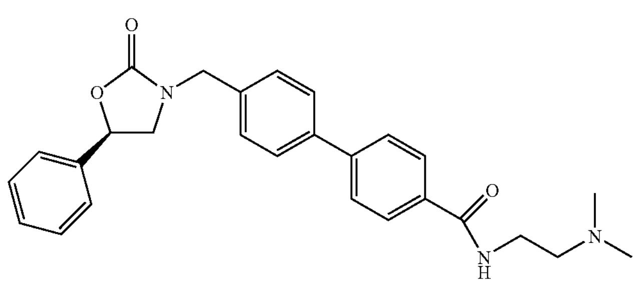 | 4'-(2-Oxo-5-(R)-phenyl-oxazolidin-3-ylmethyl) biphenyl-4-carboxylic acid (2-dimethylamino-ethyl)-amide | 34 mg, 73% White solid |
| NMR | 7.89(d, 2H), 7.63(m, 4H), 7.39(m, 7H), 6.88(bs, 1H), 5.53(t, 1H), 4.63(d, 1H), 4.48 (d, 1H), 3.84(t, 1H), 3.56(m, 2H), 3.38(dd, 1H), 2.56(t, 2H), 2.30(s, 6H). | | |

| Ex. No. | Structure | Name | Form |
|---|---|---|---|
| 10.13 | 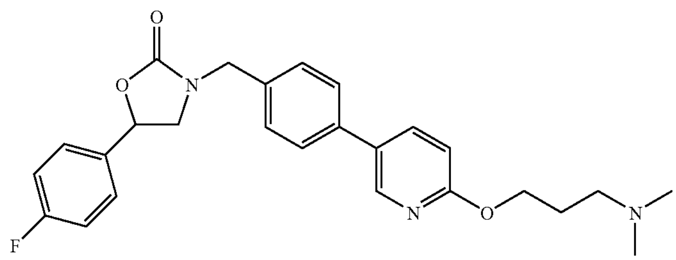 | 3-{4-[6-(3-Dimethyl amino-propoxy)-pyridin-3-yl]-benzyl}-5-(4-fluoro-phenyl-oxazolidin-2-one | 55 mg, 98% Off white solid |
| NMR | 8.36(m, 1H), 7.76(m, 1H), 7.51(d, 2H), 7.33(m, 1H), 7.07(m, 2H), 6.82(m, 1H), 5.48(1, 1H), 4.59(d, 1H), 4.40(m, 3H), 3.81(t, 1H), 3.52(dd, 1H), 2.46(m, 2H), 2.27 (s, 6H), 1.98(m, 2H). | | |
| 10.14 | 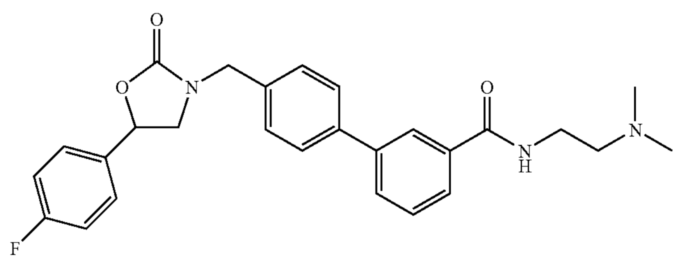 | 4'-[5-(4-Fluoro-phenyl)-2-oxo-oxazolidin-3-yl methyl]-biphenyl-3-carboxylic acid(2-dimethylamino-ethyl) amide | 40 mg, 69% white solid |
| NMR | 8.05(s, 1H), 7.71(m, 2H), 7.63(m, 2H), 7.53(m, 1H), 7.40(m, 2H), 7.33(m, 2H), 7.10(m, 2H), 6.88(bs, 1H), 5.51(t, 1H), 4.62(d, 1H), 4.48(d, 1H), 3.83(t, 1H), 3.56 (m, 2H), 3.35(t, 1H), 2.57(t, 2H), 2.30(s, 6H). | | |
| 10.15 | 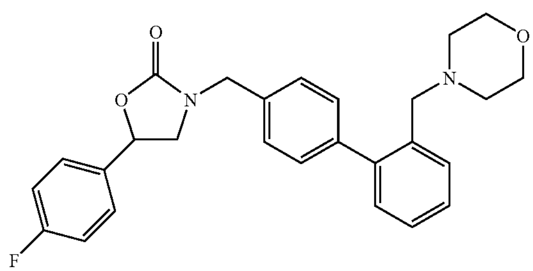 | 5-(4-Fluoro-phenyl)-3-(2'-morpholin-4-ylmethyl-biphenyl-4-ylmethyl)-oxazolidin-2-one | 37 mg, 66% Colorless oil |
| NMR | 7.43(m, 1H), 7.36(m, 2H), 7.29(m, 1H), 7.10(m, 2H), 5.52(t, 1H), 4.63(d, 1H), 4.48(d, 1H), 3.87(t, 1H), 3.65(m, 4H), 3.37(m, 3H), 2.36(m, 4H). | | |
| 10.16 | 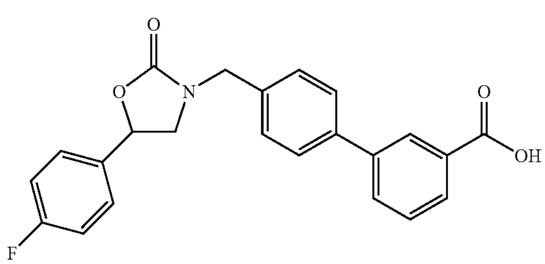 | 4'-[5-(4-Fluoro-phenyl)-2-oxo-oxazolidin-3-yl methyl]-biphenyl-3-carboxylic acid. | 92 mg, 37% white solid |
| NMR (DMSO-D6) | 13.14(bs, 1H), 8.18(m, 1H), 7.95(m, 2H), 7.73(m, 2H), 7.62(m, 1H), 7.44(m, 4H), 7.25(m, 2H), 5.64(t, 1H), 4.53(d, 1H), 4.42(d, 1H), 3.89(t, 1H), 3.35(m, 1H). | | |
| 10.17 | 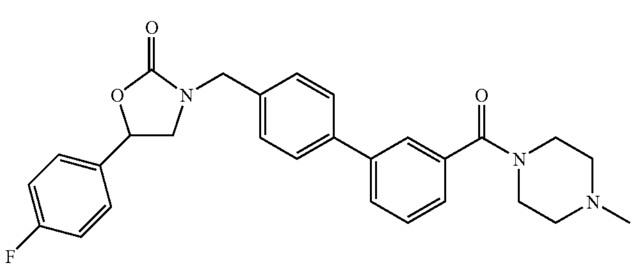 | 5-(4-Fluoro-phenyl)-3-[3'-(4-methyl-piperazine-1-carbonyl)-biphenyl-4-ylmethyl]-oxazolidin-2-one. | 55 mg, 93% white solid |
| NMR | 7.62(m, 4H), 7.47(m, 1H), 7.39(m, 3H), 7.30(m, 2H), 7.07(m, 2H), 5.49(t, 1H), 4.58(d, 1H), 4.46(d, 1H), 3.82(m, 3H), 3.49(m, 2H), 3.33(dd, 1H), 2.51(m, 2H), 2.35(m, 5H). | | |

| Ex. No. | Structure | Name | Form |
|---|---|---|---|
| 10.18 | 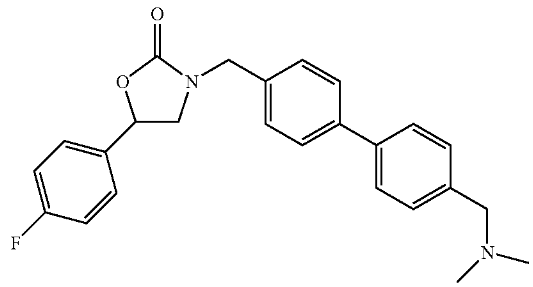 | 3-(4'-Dimethylamino methyl-biphenyl-4-ylmethyl)-5-(4-fluoro-phenyl)-oxazolidin-2-one. | 36 mg, 89% white solid |
| NMR | 7.58(m, 4H), 7.36(m, 6H), 7.08(m, 2H), 5.49(t, 1H), 4.60(d, 1H), 4.47(d, 1H), 3.82 (t, 1H), 3.50(s, 2H), 3.33(dd, 1H), 2.30(s, 6H). | | |
| 10.19 | 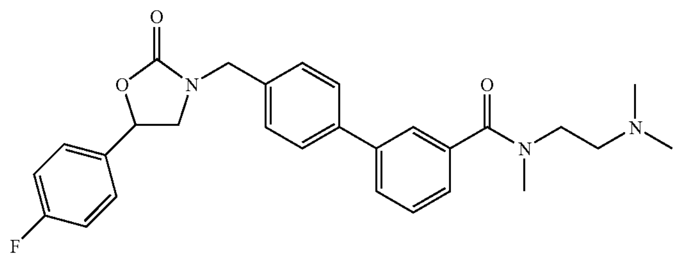 | 4'-[5-(4-Fluoro-phenyl)-2-oxo-oxazolidin-3-yl methyl]-biphenyl-3-carboxylic acid(2-dimethylamino-ethyl)-methyl-amide | 49 mg, 82% colorless oil |
| NMR | 7.62(m, 4H), 7.48(m, 1H), 7.37(m, 5H), 7.10(m, 2H), 5.50(t, 1H), 4.59(d, 1H), 4.47(d, 1H), 3.82(t, 1H), 3.69(m, 1H), 3.38(m, 2H), 3.09(d, 3H), 2.61(bs, 1H), 2.39 (m, 4H), 2.05(s, 3H). | | |
| 10.20 | 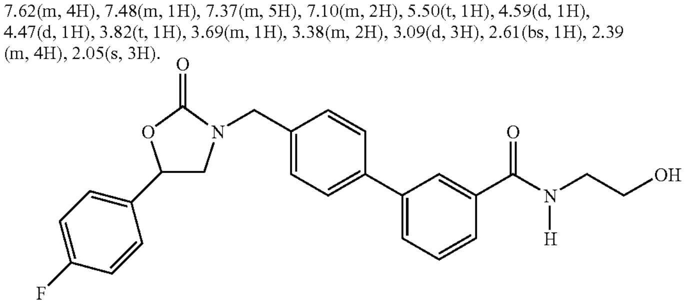 | 4'-[5-(4-Fluoro-phenyl)-2-oxo-oxazolidin-3-yl methyl]-biphenyl-3-carboxylic acid(2-hydroxy-ethyl)-amide | 27 mg, 50% pale yellow solid. |
| NMR | 8.04(s, 1H), 7.75(m, 2H), 7.61(m, 2H), 7.53(m, 1H), 7.32(m, 4H), 7.07(m, 2H), 6.85(bs, 1H), 5.49(t, 1H), 4.60(d, 1H), 4.46(d, 1H), 3.87(m, 3H), 3.79(m, 2H), 3.34 (t, 1H), 2.77(bs, 1H). | | |
| 10.21 | 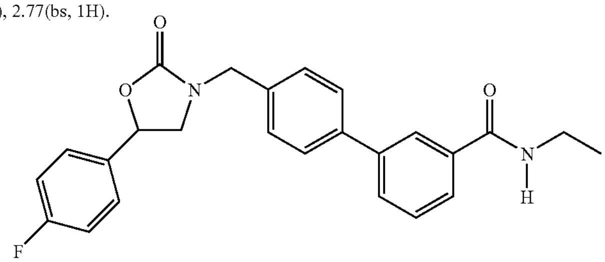 | 4'-[5-(4-Fluoro-phenyl)-2-oxo-oxazolidin-3-yl methyl]-biphenyl-3-carboxylic acid ethylamine | 27 mg, 50% white solid |
| NMR | 8.02(s, 1H), 7.71(m, 2H), 7.62(m, 2H), 7.52(m, 1H), 7.32(m, 4H), 7.10(m, 2H), 6.23(bs, 1H), 5.50(t, 1H), 4.60(d, 1H), 4.47(d, 1H), 3.83(m, 1H), 3.55(m, 2H), 3.34 (t, 1H), 1.27(m, 3H). | | |
| 10.22 | 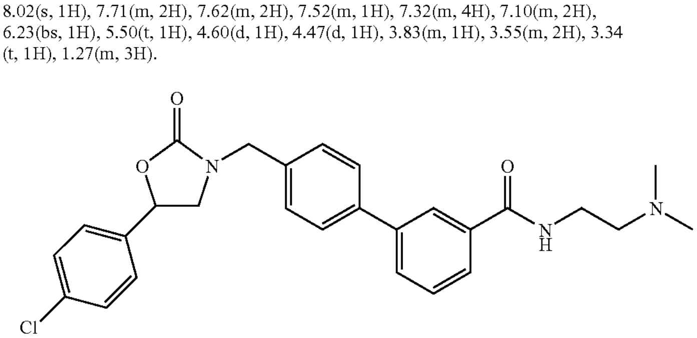 | 4'-[5-(R)-(4-Chloro-phenyl)-2-oxo-oxazolidin-3-yl methyl] biphenyl-3-carboxylic acid(2-dimethylamino-ethyl)-amide | 32 mg, 55% white solid |
| NMR | 8.05(s, 1H), 7.63(m, 2H), 7.56(m, 2H), 7.52(m, 1H), 7.38(m, 4H), 7.28(m, 2H), 6.94(bs, 1H), 5.49(t, 1H), 4.60(d, 1H), 4.47(d, 1H), 3.83(t, 1H), 3.55(m, 2H), 3.31 (t, 1H), 2.52(m, 2H), 2.28(s, 6H). | | |

-continued

| Ex. No. | Structure | Name | Form |
|---|---|---|---|
| 10.23 | 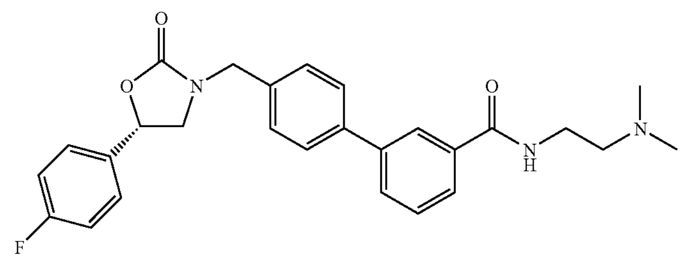 | 4'-[5-(S)-(4-Fluoro-phenyl)-2-oxo-oxazolidin-3-yl methyl] biphenyl-3-carboxylic acid(2-dimethylamnino-ethyl)-amide | 102 mg<br>Pale brown solid |
| NMR | Obtained by the HPLC separation of Example 10n on chiralpak AD column.<br>8.06(s, 1H), 7.73(m, 2H), 7.62(m, 2H), 7.52(m, 1H), 7.33(m, 4H), 7.05(m, 3H),<br>5.49(t, 1H), 4.60(d, 1H), 4.46(d, 1H), 3.82(t, 1H), 3.56(m, 2H), 3.33(t, 1H), 2.56(t, 2H), 2.29(s, 6H). | | |
| 10.24 | 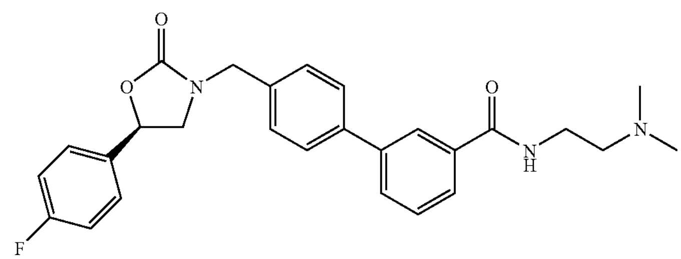 | 4'-[5-(R)-(4-Fluoro-oxazolidin-3-yl methyl] biphenyl-3-carboxylic acid(2-dimethylamino-ethyl)-amide | 112 mg<br>Pale brown solid |
| NMR | Obtained by the HPLC separation of Example 10n on chiralpak AD column.<br>8.06(s, 1H), 7.62(m, 4H), 7.50(m, 1H), 7.33(m, 4H), 7.05(m, 3H), 5.47(t, 1H), 4.58<br>(d, 1H), 4.46(d, 1H), 3.81(t, 1H), 3.70(m, 2H), 3.33(t, 1H), 2.50(t,2H), 2.29(s, 6H). | | |
| 10.25 | 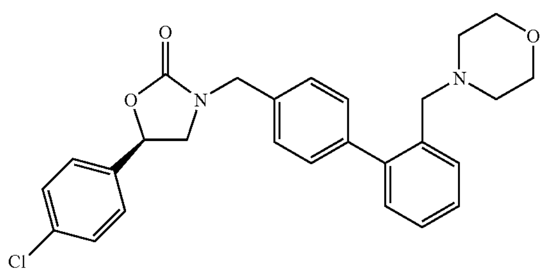 | 5-(R)-(4-Chloro-phenyl)-3-(2'-morpholin-4-ylmethyl-biphenyl-4-ylmethyl)-oxazolidin-2-one | 43 mg, 97%<br>Colorless oil |
| NMR | 7.42(m, 1H), 7.36(m, 11H), 5.51(t, 1H), 4.62(d, 1H), 4.48(d, 1H), 3.88(t, 1H), 3.65<br>(m, 4H), 3.38(m, 3H), 2.36(m, 4H). | | |
| 10.26 | 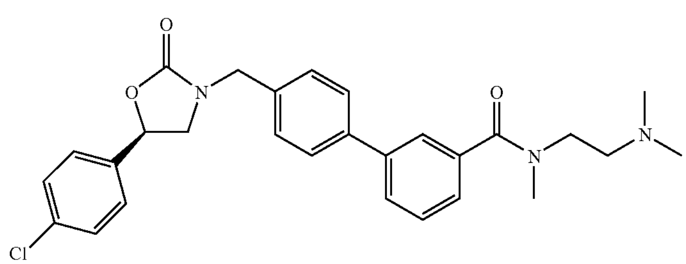 | 4'-[5-(R)-(4-Chloro-phenyl)-2-oxo-oxazolidin-3-yl methyl] biphenyl-3-carboxylic acid(2-dimethylamino-ethyl)-methyl-amide | 49 mg, 82%<br>white solid |
| NMR | 7.59(m, 4H), 7.45(m, 1H), 7.37(m, 5H), 7.28(m, 2H), 5.48(t, 1H), 4.57(d, 1H),<br>4.45(d, 1H), 3.82(t, 1H), 3.68(m, 1H), 3.38(m, 1H), 3.30(dd, 1H), 3.02(d, 3H), 2.61<br>(m, 1H), 2.38(m, 4H), 2.07(s, 3H). | | |
| 10.27 | 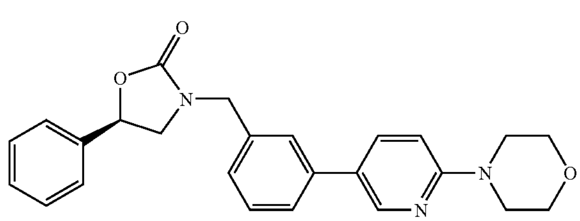 | 3-[3-(6-Morpholin-4-yl-pyridin-3-yl)-benzyl]-5-(R)-phenyl-oxazolidin-2-one | 60 mg, 73%<br>brown solid |
| NMR | 8.44(d, 1H), 7.71(d, 1H), 7.47-7.33(m, 9H), 7.25(d, 1H), 6.72(d,1H), 5.51(t, 1H),<br>4.62(d, 1H), 4.47(d, 1H), 3.88-3.81(m, 5H), 3.59-3.56(m, 4H), 3.36(t, 1H). | | |

-continued

| Ex. No. | Structure | Name | Form |
|---|---|---|---|
| 10.28 | 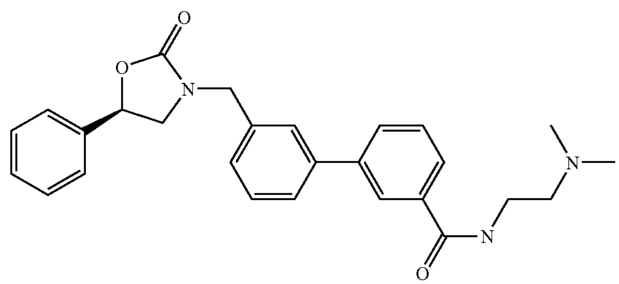 | 3'-(2-Oxo-5-(R)-phenyl-oxazolidin-3-yl methyl)-biphenyl-3-carboxylic acid(2-dimethylamino-ethyl)-amide | 90mg, 100% colourless gum |
| NMR | 8.05(s, 1H), 7.80-7.70(dd, 2H), 7.56-7.46(m, 9H), 6.92(br s, 1H) 5.50(1, 1H), 4.64 (d, 1H), 4.47(d, 1H), 3.84(t, 1H), 3.56(g, 2H), 3.36(t, 1H), 2.56(t, 2H), 2.29(s, 6H). | | |
| 10.29 | 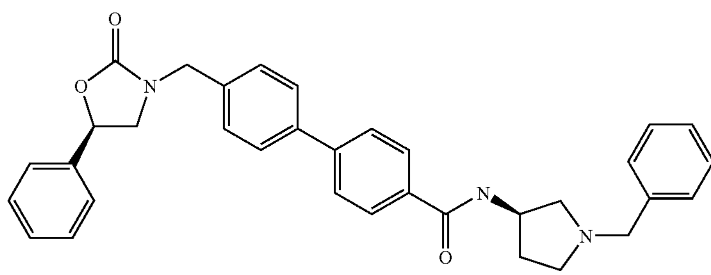 | 4'-(2-Oxo-5-(R)-phenyl-oxazolidin-3-yl methyl)-biphenyl-4-carboxylic acid(1-benzyl-pyrrolidin-3-(S)-yl)-amide | 19 mg, 34% off white solid |
| NMR | 7.86(d, 2H), 7.63(1,4H), 7.42-7.32(m, 11H), 6.67(d, 1H), 5.53(t, 1H), 4.636(br s, 1H), 4.63(d, 1H), 4.48(d, 1H), 3.84(t, 1H), 3.67(s, 2H), 3.37(t, 1H), 2.98(m, 1H), 2.75(m, 1H), 2.69-2.64(m, 1H), 2.41-2.32(m, 2H), 2.13(br s, 1H), 1.77(br s, 1H). | | |
| 10.30 | 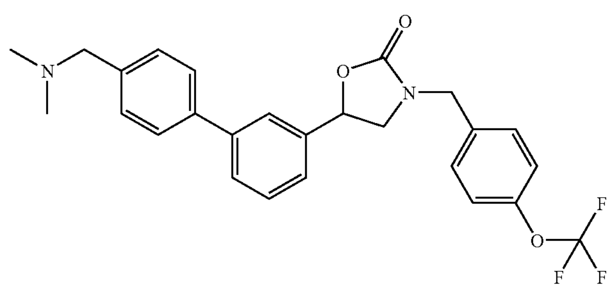 | 5-(4'-Dimethylamino methyl-biphenyl-3-yl)-3-(4-trifluoromethoxy-benzyl)-oxazolidm-2-one | 10 mg, 17% yellow oil |
| NMR | 7.58-7.51(m, 4H), 7.49-7.29(m, 6H), 7.28(d, 1H), 7.22(d, 1H), 5.58(1, 1H), 4.69(d, 1H), 4.43(d, 1H), 3.85(t, 1H), 3.50(5, 2H), 2.29(s, 6H). | | |

Example 11.1

3-[4'-(4-Methyl-piperazin-1-ylmethyl)-biphenyl-4-ylmethyl]-5-phenyl-oxazolidin-2-one

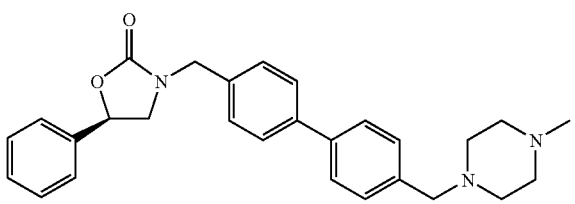

General Procedure (6): A solution of 2-(4-Bromomethyl-phenyl)-4,4,5,5-tetramethyl-[1,3,2]dioxaborolane (60 mg, 212 mmol) in N-methyl piperazine (0.5 mL) was heated at 70-75° C. for 3 h. The reaction mixture was cooled down to RT, diluted with dichloromethane (6 mL), washed with water (2×2 mL), brine (2 mL), dried over anhydrous sodium sulphate and concentrated in vacuo to yield 1-methyl-4-[4-(4,4,5,5-tetramethyl-[1,3,2]dioxborolan-2-yl)-benzyl]-piperazine in reasonably good purity. This boronate ester was used for Suzuki coupling reaction with 3-(4-Iodo-benzyl)-5-(R)-phenyl)-oxazolidin-2-one (40 mg, 105 mmol), without any purification, as described in General Procedure (5). The desired product was isolated as a white solid (28 mg, 60%) by silica gel column chromatography. $^1$H NMR (300 MHz, CDCl$_3$): δ 7.56 (m, 4H), 7.38 (m, 9H), 5.52 (t, 1H), 4.61 (d, 1H), 4.46 (d, 1H), 3.83 (t, 1H), 3.57 (s, 2H), 3.37 (dd, 1H), 2.53 (bs, 8H), 2.32 (s, 3H). (Note: where N-Boc protected piperazine was used as the base, the final product was obtained by cleaving off the Boc group using trifluoro acetic acid in dichloromethane.)

In a similar fashion the following compounds were synthesized:

| Ex. No. | Structure | Name | Form |
|---|---|---|---|
| 11.2 | 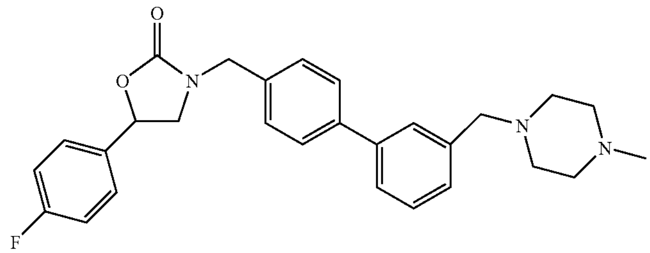 | 5-(4-Fluoro-phenyl)-3-[3'-(4-methyl-piperazin-1-ylmethyl)-biphenyl-4-ylmethyl]-oxazolidin-2-one | 29 mg, 60% Colorless oil. |
| NMR | 7.45(m, 4H), 7.32(m, 6H), 7.08(t, 2H), 5.49(t, 1H), 4.60(d, 1H), 4.48(d, 1H), 3.82 (t, 1H), 3.60(s, 2H), 3.31(dd, 1H), 2.39(bs, 8H), 2.33(s, 3H). | | |
| 11.3 | 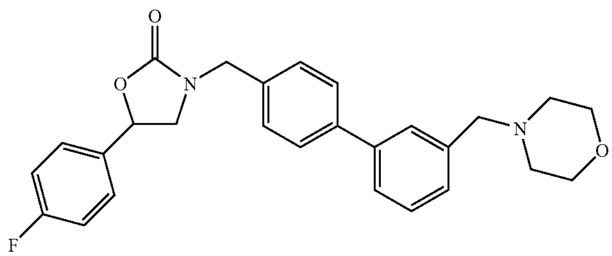 | 5-(4-Fluoro-phenyl)-3-(3'-morpholin-4-yl methyl-biphenyl-4-ylmethyl)-oxazolidin-2-one | 23 mg, 48% Colorless oil. |
| NMR | 7.56(m, 4H), 7.36(m, 6H), 7.09(t, 2H), 5.50(t, 1H), 4.61(d, 1H), 4.48(d, 1H), 3.82 (t, 1H), 3.74(m, 4H), 3.58(s, 2H), 3.34(dd, 1H), 2.50(m, 4H). | | |
| 11.4 | 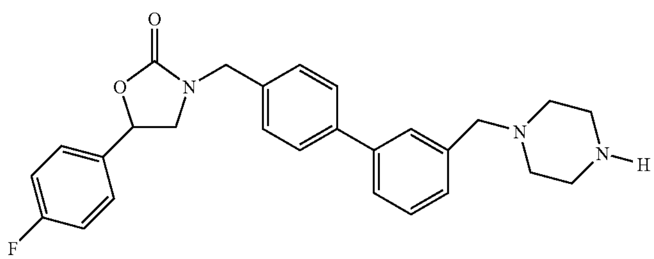 | 5-(4-Fluoro-phenyl)-3-(3'-piperazin-1-ylmethyl)-biphenyl-4-ylmethyl)-oxazolidin-2-one | 18 mg, 25% Colorless oil. |
| NMR | 7.55(m, 4H), 7.38(m, 6H), 7.09(t, 2H), 5.50(t, 1H), 4.61(d, 1H), 4.48(d, 1H), 3.82 (t, 1H), 3.58(s, 2H), 3.34(dd, 1H), 2.95(m, 4H), 2.59(bs, 1H), 2.50(bs, 4H). | | |
| 11.5 | 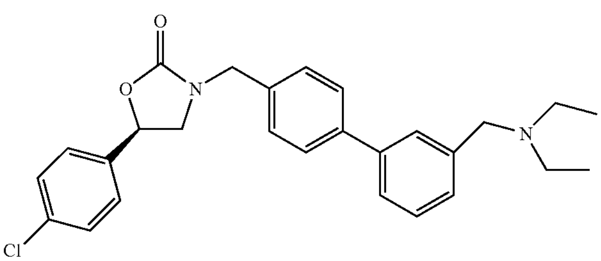 | 5-(R)-(4-Chloro-phenyl)-3-(3'-diethylamino methyl-biphenyl-4-ylmethyl)-oxazolidin-2-one | 31 mg, 71% Waxy white solid |
| NMR | 7.60(m, 3H), 7.45(m, 1H), 7.38(m, 6H), 7.28(m, 2H), 5.48(t, 1H), 4.60(d, 1H), 4.47(d, 1H), 3.82(t, 1H), 3.65(s, 2H), 3.31(dd, 1H), 2.58(q, 4H), 1.09(t, 6H). | | |
| 11.6 | 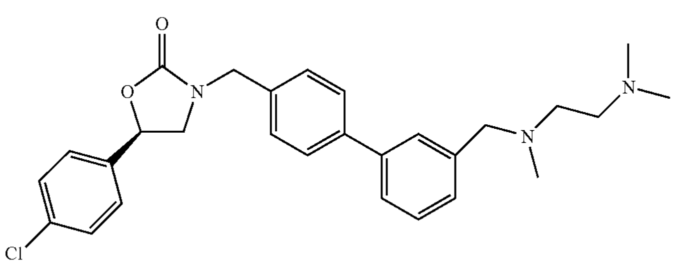 | 5-(R)-(4-Chloro-phenyl)-3-(3'-{[dimethylamino-ethyl)-methyl-amino]-methyl}biphenyl-4-ylmethyl)-oxazolidin-2-one | 27 mg, 58% Pale brown oil |
| NMR | 7.59(m, 3H), 7.39(m, 1H), 7.37(m, 6H), 7.27(m, 2H), 5.48(t, 1H), 4.59(d, 1H), 4.47(d, 1H), 3.82(t, 1H), 3.60(s, 2H), 3.31(dd, 1H), 2.51(m, 4H), 2.29(s, 3H), 2.24(s, 6H). | | |

-continued

| Ex. No. | Structure | Name | Form |
|---|---|---|---|
| 11.7 | 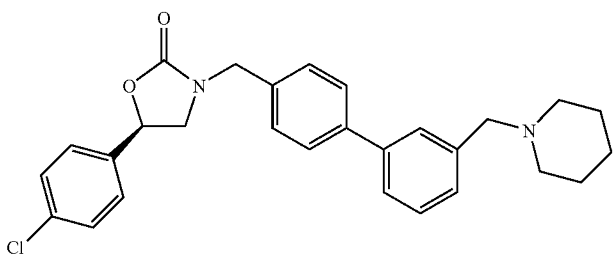 | 5-(R)-(4-Chloro-phenyl)-3-(3'-piperidin-1-yl methyl-biphenyl-4-ylmethyl)-oxazolidin-2-one | 37 mg, 83% Pale brown oil. |
| NMR | 7.61(m, 2H), 7.55(s, 1H), 7.40(m, 1H), 7.38(m, 6H), 7.28(m, 2H), 5.49(t, 1H), 4.60 (d, 1H), 4.47(d, 1H), 3.83(t, 1H), 3.55(s, 2H), 3.11(dd, 1H), 2.42(m, 4H), 1.60(m, 4H), 1.47(m, 2H). | | |
| 11.8 | 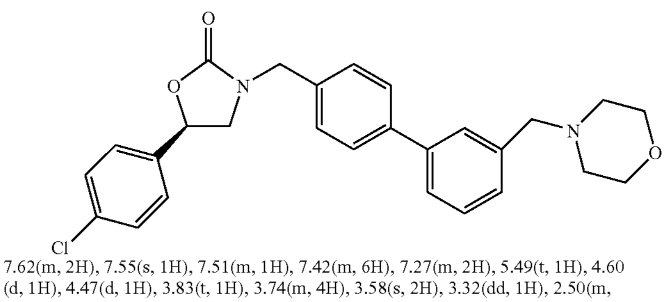 | 5-(R)-(4-Chloro-phenyl)-3-(3'-morpholin-4-yl methyl-biphenyl-4-ylmethyl)-oxazolidin-2-one | 37 mg, 83% White solid. |
| NMR | 7.62(m, 2H), 7.55(s, 1H), 7.51(m, 1H), 7.42(m, 6H), 7.27(m, 2H), 5.49(t, 1H), 4.60 (d, 1H), 4.47(d, 1H), 3.83(t, 1H), 3.74(m, 4H), 3.58(s, 2H), 3.32(dd, 1H), 2.50(m, 4H). | | |
| 11.9 | 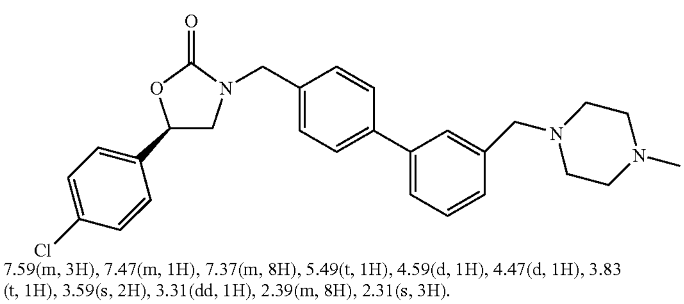 | 5-(R)-(4-Chloro-phenyl)-3-[3'-(4-methyl-piperazin-1-ylmethyl)-biphenyl-4-ylmethyl]-oxazolidin-2-one | 38 mg, 89% Brown oil |
| NMR | 7.59(m, 3H), 7.47(m, 1H), 7.37(m, 8H), 5.49(t, 1H), 4.59(d, 1H), 4.47(d, 1H), 3.83 (t, 1H), 3.59(s, 2H), 3.31(dd, 1H), 2.39(m, 8H), 2.31(s, 3H). | | |
| 11.10 | 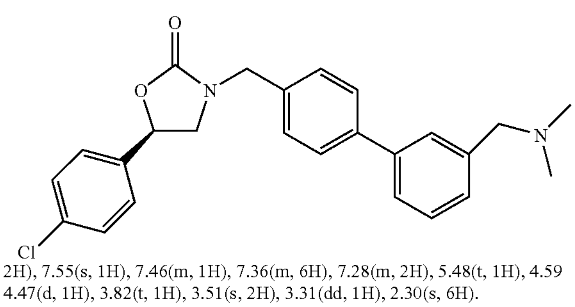 | 5-(R)-(4-Chloro-phenyl)-3-(3'-dimethylamino-methyl)-oxazolidin-2-methyl-biphenyl-4-one | 43 mg, 53% Pale brown oil. |
| NMR | 7.61(m, 2H), 7.55(s, 1H), 7.46(m, 1H), 7.36(m, 6H), 7.28(m, 2H), 5.48(t, 1H), 4.59 (d, 1H), 4.47(d, 1H), 3.82(t, 1H), 3.51(s, 2H), 3.31(dd, 1H), 2.30(s, 6H). | | |
| 11.11 | 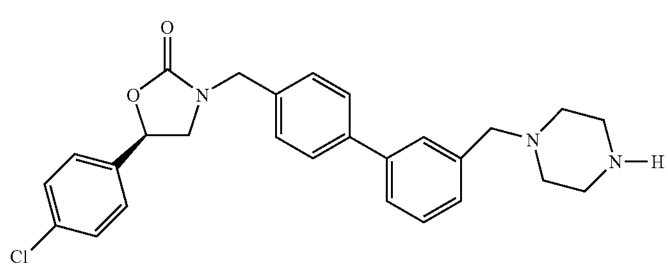 | 5-(R)-(4-Chloro-phenyl)-3-(3'-piperazin-1-ylmethyl)-biphenyl-4-ylmethyl)-oxazolidin-2-one | 53 mg, 59% White foamy solid. |
| NMR | 7.60(m, 2H), 7.55(s, 1H), 7.47(m, 1H), 7.38(m, 6H), 7.27(m, 2H), 5.48(t, 1H), 4.59 (d, 1H), 4.47(d, 1H), 3.82(t, 1H), 3.57(s, 2H), 3.31(dd, 1H), 2.91(bs, 4H), 2.47(bs, 4H). | | |

| Ex. No. | Structure | Name | Form |
|---|---|---|---|
| 11.12 | 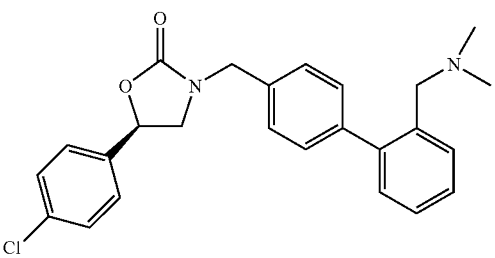 | 5-(R)-(4-Chloro-phenyl)-3-(2'-dimethylamino methyl-biphenyl-4-ylmethyl)-oxazolidin-2-one. | 30 mg, 69% Pale yellow oil. |
| NMR | 7.40(d, 1H), 7.36(m, 11H), 5.52(t, 1H), 4.62(d, 1H), 4.48(d, 1H), 3.88(t, 1H), 3.35 (m, 3H), 2.16(s, 6H). | | |
| 11.13 | 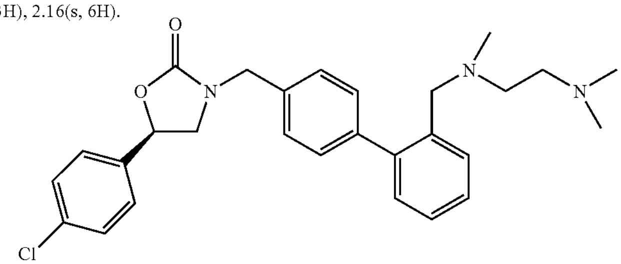 | 5-(R)-(4-Chloro-phenyl)-3-(2'-{[(2-dimethylamino-ethyl)-methyl-amino]-methyl} biphenyl-4-yl methyl) oxazolidin-2-one. | 40 mg, 87% Colorless oil. |
| NMR | 7.39(d, 1H), 7.33(m, 1OH), 7.28(d, 1H), 5.51(t, 1H), 4.64(d, 1H), 4.46(d, 1H), 3.87 (t, 1H), 3.53(s, 2H), 3.35(dd, 1H), 2.35(m, 4H), 2.18(s, 6H), 2.14(s, 3H). | | |
| 11.14 | 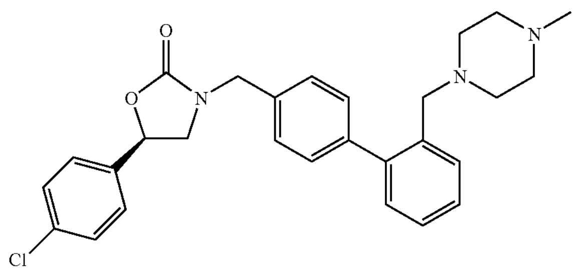 | 5-(R)-(4-Chloro-phenyl)-{3-[2'-(4-methyl-piperazin-1-yl methyl) biphenyl-4-ylmethyl)-oxazolidin-2-one | 38 mg, 83% Colorless oil. |
| NMR | 7.42(d, 1H), 7.33(m, 11H), 5.51(t, 1H), 4.63(d, 1H), 4.46(d, 1H), 3.86(t, 1H), 3.42 (s, 2H), 3.34(dd, 1H), 2.33(bs, 8H), 1.27(s, 3H). | | |
| 11.15 | 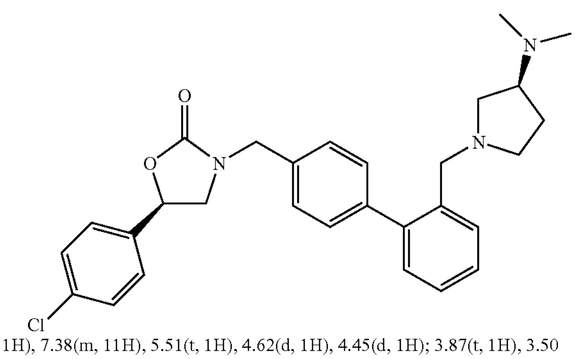 | 5-(R)-(4-Chloro-phenyl)-3-[2'-(3-(S)-dimethylamino-pyrrolidin-1-yl methyl)-1-biphenyl-4-ylmethyl]-oxazolidin-2-one | 42 mg, 87% Pale yellow oil. |
| NMR | 7.42(d, 1H), 7.38(m, 11H), 5.51(t, 1H), 4.62(d, 1H), 4.45(d, 1H); 3.87(t, 1H), 3.50 (s, 2H), 3.34(dd, 1H), 2.73(m, 2H), 2.62(m, 1H), 2.43(m, 1H), 2.28(d, 2H), 1.92(s, 6H), 1.67(m, 1H). | | |
| 11.16 | 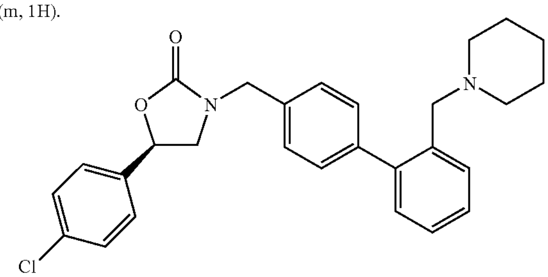 | 5-(R)-(4-Chloro-phenyl)-3-(2'-piperidin-1-yl methyl-biphenyl-4-ylmethyl)-oxazolidin-2-one | 20 mg, 45% Waxy white solid |
| NMR | 7.43(d, 1H), 7.33(m, 11H), 5.51(t, 1H), 4.62(d, 1H), 4.48(d, 1H), 3.87(t, 1H), 3.34 (m, 3H), 2.28(bs, 4H), 1.39(m, 4H), 1.27(m, 2H). | | |

| Ex. No. | Structure | Name | Form |
|---|---|---|---|
| 11.17 | 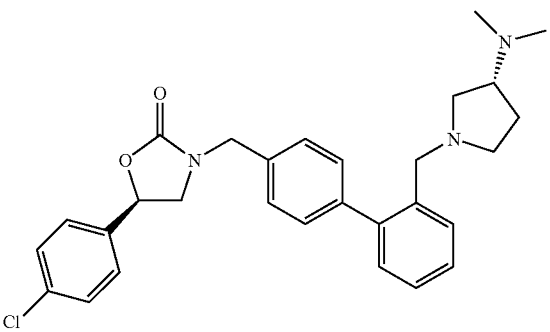 | 5-(R)-(4-Chloro-phenyl)-3-[2'-(3-(R)-dimethylamino-pyrrolidin-1-ylmethyl)-oxazolidin-2-one | 32 mg, 66% Pale yellow oil. |
| NMR | 7.41(d, 1H), 7.37(m, itH), 5.51(t, 1H), 4.63(d, 1H), 4.44(d, 1H), 3.87(t, 1H), 3.49 (s, 2H), 3.35(dd, 1H), 2.72(m, 2H), 2.62(m, 1H), 2.42(m, 1H), 2.27(d, 2H), 1.92(s, 6H), 1.67(m, 1H). | | |
| 11.18 | 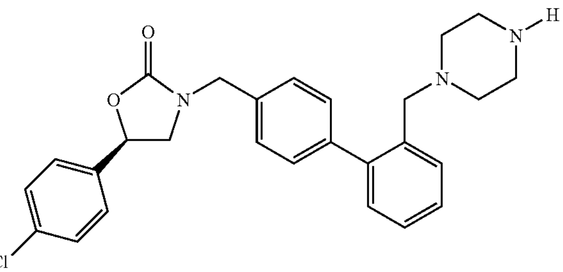 | 5-(R)-(4-Chloro-phenyl)-3-(2'-piperazin-1-yl methyl-biphenyl-4-ylmethyl)-oxazolidin-2-one | 55 mg, 84% White foamy solid. |
| NMR | 7.43(d, 1H), 7.34(m, 11H), 5.51(1, 1H), 4.62(d, 1H), 4.47(d, 1H), 3.87(t, 1H), 3.34 (m, 3H), 2.81(m, 4H), 2.31(bs, 4H). | | |
| 11.19 | 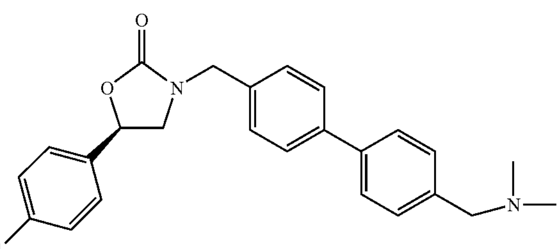 | 5-(R)-(4-Chloro-phenyl)-3-(4'-dimethylamino methyl-biphenyl-4-ylmethyl)-oxazolidin-2-one. | 40 mg, 98% White solid. |
| NMR | 7.60(m, 4H), 7.38(m, 6H), 7.27(m, 2H), 5.48(t, 1H), 4.60(d, 1H), 4.46(d, 1H), 3.82 (t, 1H), 3.49(s, 2H), 3.31(dd, 1H), 2.3(s, 6H). | | |
| 11.20 | 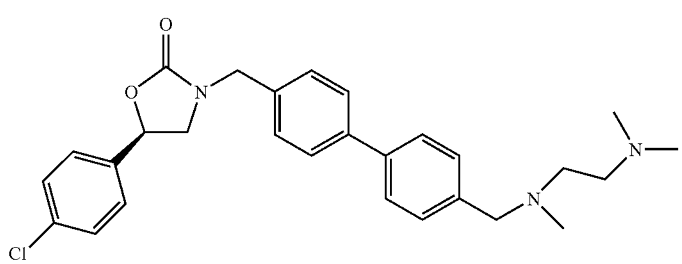 | 5-(R)-(4-Chloro-phenyl)-3-(4'-{[(2-dimethylamino-ethyl)-methyl-amino]-methyl}-biphenyl-4-yl methyl)-oxazolidin-2-one. | 28 mg, 54% Yellow solid. |
| NMR | 7.55(m, 4H), 7.37(m, 6H), 7.25(m, 2H), 5.48(t, 1H), 4.59(d, 1H), 4.46(d, 1H), 3.82 (t, 1H), 3.54(s, 2H), 3.31(dd, 1H), 2.44(t, 2H), 2.33(t, 2H), 2.23(s, 3H), 2.21(s, 6H). | | |
| 11.21 | 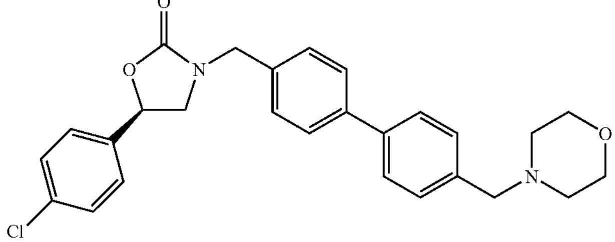 | 5-(R)-(4-Chloro-phenyl)-3-(4'-morpholin-4-yl methyl-biphenyl-4-ylmethyl)-oxazolidin-2-one. | 17 mg, 38% White solid. |
| NMR | 7.57(m, 4H), 7.38(m, 6H), 7.27(m, 2H), 5.49(t, 1H), 4.60(d, 1H), 4.47(d, 1H), 3.84 (t, 1H), 3.75(m, 4H), 3.56(s, 2H), 3.32(dd, 1H), 2.50(m, 4H). | | |

-continued

| Ex. No. | Structure | Name | Form |
|---|---|---|---|
| 11.22 | 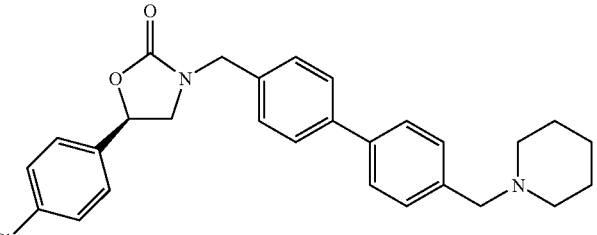 NMR 7.56(m, 1H), 7.38(m, 6H), 7.28(m, 2H), 5.48(t, 1H), 4.60(d, 1H), 4.46(d, 1H), 3.83 (t, 1H), 3.53(s, 2H), 3.32(dd, 1H), 2.42(bs, 4H), 1.61(m, 4H), 1.48(m, 2H). | 5-(R)-(4-Chloro-phenyl)-3-(4'-piperidin-1-yl methyl-biphenyl-4-ylmethyl)-oxazolidin-2-one | 30 mg, 67% White solid. |
| 11.23 | 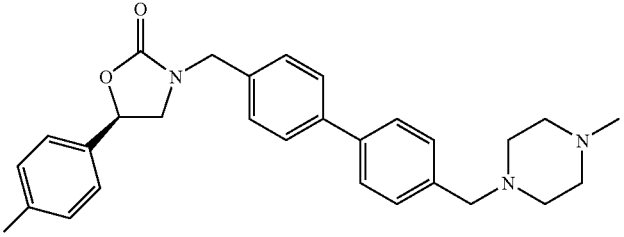 NMR 7.56(m, 4H), 7.37(m, 6H), 7.27(m, 2H), 5.47(t, 1H), 4.60(d, 1H), 4.46(d, 1H), 3.83 (t, 1H), 3.57(s, 2H), 3.31(dd, 1H), 2.51 s, 8H), 2.31 (s, 3H). | 5-(R)-(4-Chloro-phenyl)-3-[4'-(4-methyl-piperazin-1-yl methyl)-biphenyl-4-ylmethyl)-oxazolidin-2-one | 31 mg, 67% White solid. |
| 11.24 | 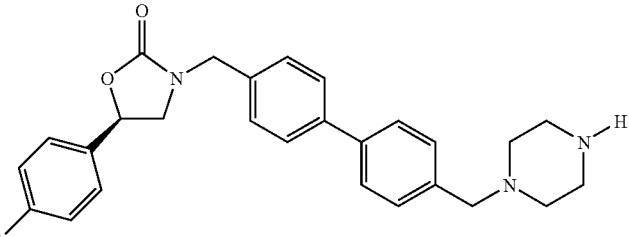 NMR 7.56(m, 1H), 7.38(m, 6H), 7.27(m, 2H), 5.48(t, 1H), 4.60(d, 1H), 4.46(d, 1H), 3.83 (t, 1H), 3.55(s, 2H), 3.31(dd, 1H), 2.92(m, 4H), 2.46(bs, 4H). | 5-(R)-(4-Chloro-phenyl)-3-(4'-piperazin-1-yl methyl-biphenyl-4-ylmethyl)-oxazolidin-2-one | 37 mg, 51% White solid. |

Example 12

5-(4-fluoro-phenyl)-3-(3'-hydroxymethyl-biphenyl-4-ylmethyl)-oxazolidin-2-one

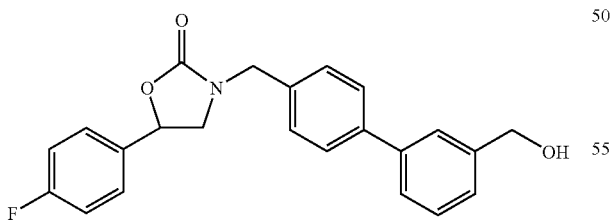

To a solution of 4'-[5-(4-Fluoro-phenyl)-2-oxo-oazolidin-3-ylmethyl]-biphenyl-3-carbaldehyde (40 mg, 0.1 mmol, synthesized by the Suzuki coupling protocol described in General Procedure (5) in methanol was added 0.13 mL (0.13 mmol) of sodium cyanoborohydride (1 M in THF) and the reaction flask was stirred overnight at RT. The reaction mixture was concentrated; the residue was taken up in dichloromethane (4 mL), washed with saturated aqueous sodium bicarbonate solution (2 mL), dried over anhydrous sodium sulfate and concentrated in vacuo. Purification of the product by chromatography on silica gel, eluting with 10-40% ethyl acetate yielded the title compound as a white solid (29 mg, 73%). $^1$H NMR (300 MHz, CDCl$_3$): δ 7.61 (m, 3H), 7.50 (m, 2H), 7.38 (m, 5H), 7.08 (m, 2H), 5.48 (t, 1H), 4.78 (s, 2H), 4.59 (d, 1H), 4.46 (d, 1H), 3.81 (t, 1H), 3.33 (dd, 1H).

Example 13.1

5-(4-fluoro-phenyl)-3-[4-(pyrazin-2-yloxy)-benzyl]-oxazolidin-2-one

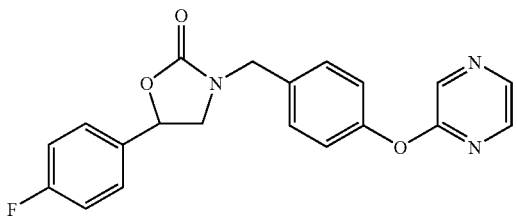

Sodium cyanoborohydride (0.62 mL, 1 M in THF) was added to a solution of 2-amino-1-(4-fluoro-phenyl)-ethanol (80 mg, 0.52 mmol), 4-(Pyrazin-2-yloxy)-benzaldehyde (103 mg, 0.52 mmol) and glacial acetic acid (0.5 mL), in methanol (3 mL) at RT and the flask was stirred overnight. The reaction mixture was concentrated in vacuo; the residue was quenched with saturated aqueous sodium bicarbonate solution and then extracted with dichloromethane (3×4 mL). The combined organic phases were dried over anhydrous sodium sulfate and concentrated again in vacuo to yield 1-(4-fluoro-phenyl)-2-[4(pyrazin-2-yloxy)-benzyl amino]-ethanol as a white solid 62 mg, 35%).

To a solution of the intermediate obtained above in dichloromethane (3 mL) at 5° C., was added diisopropyl ethylamine (0.1 mL, 60 mmol) followed by Tri phosgene (60 mg, 0.2 mmol) and the flask was stirred overnight at RT. The reaction mixture was quenched with 1 N HCl, then neutralized with saturated aqueous sodium bicarbonate solution and extracted with dichloromethane (2×4 mL). The organic phase was dried over anhydrous sodium sulfate and concentrated in vacuo. The residue is purified by chromatography on silica gel, eluting with 30-50% ethyl acetate in hexanes, to yield the title compound as a white solid (31 mg, 46%). $^1$H NMR (300 MHz, CDCl$_3$): δ 8.46 (s, 1H), 8.36 (d, 1H), 8.11 (m, 1H), 7.37 (m, 4H), 7.2 (m, 4H), 5.49 (t, 1H), 4.60 (d, 1H), 4.43 (d, 1H), 3.84 (t, 1H), 3.35 (dd, 1H).

The following compounds were made in a similar manner:

| Ex. No. | Structure | Name | Form |
|---|---|---|---|
| 13.2 | 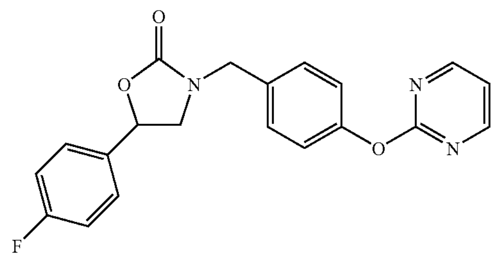 | 5-(4-fluoro-phenyl)-3-[4-(pyrimidin-2-yloxy)-benzyl]-oxazolidin-2-one | 38 mg, 40%. Colorless oil. |
| NMR | 8.57(d, 2H), 7.34(m, 4H), 7.22(m, 2H), 7.08(m, 3H), 5.49(t, 1H), 4.60(d, 1H), 4.41 (d, 1H), 3.84(t, 1H), 3.35(dd, 1H). | | |
| 13.3 | 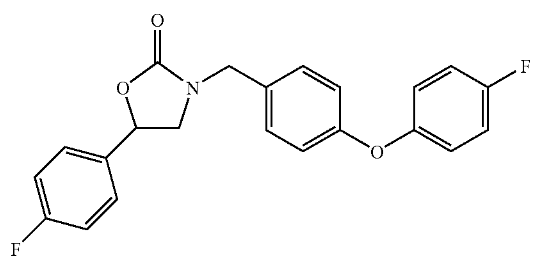 | 3-[4-(4-fluoro-phenoxy)-benzyl]-5-(4-fluoro-phenyl)-oxazolidin-2-one | 65 mg, 63%. Colorless oil. |
| NMR | 7.27(m, 4H), 7.05(m, 8H), 5.47(t, 1H), 4.52(d, 1H), 4.39(d, 1H), 3.80(t, 1H), 3.31 (dd, 1H). | | |
| 13.4 | 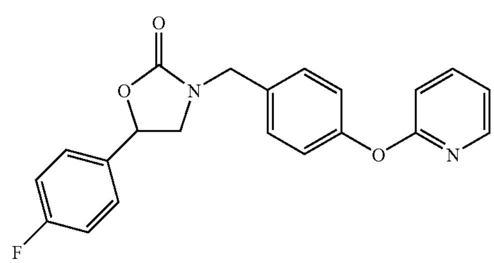 | 5-(4-Fluoro-phenyl)-3-[4-(pyridin-2-yloxy)-benzyl]-oxazolidin-2-one | 25 mg, 42%. Colorless oil. |
| NMR | 8.19(m, 1H), 7.70(m, 1H), 7.35(m, 4H), 7.05(m, 5H), 6.95(d, 1H), 5.48(t, 1H), 4.58(d, 1H), 4.41(d, 1H), 3.83(t, 1H~i, 3.34(dd, 1H). | | |
| 13.5 | 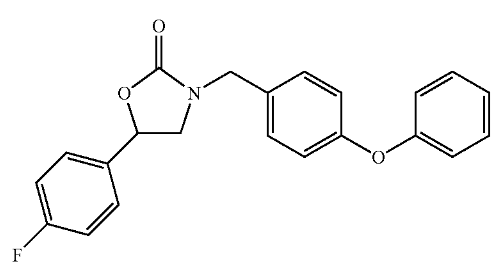 | 5-(4-Fluoro-phenyl)-3-(4-phenoxy-benzyl)-oxazolidin-2-one | 69 mg, 75%. Colorless oil. |
| NMR | 7.37(m, 6H), 7.05(m, 7H), 5.48(t, 1H), 4.54(d, 1H), 4.40(d, 1H), 3.80(t, 1H), 3.31 (dd, 1H). | | |

Example 14

5-(R)-(4-chlorophenyl)-3-[4-(4-pyridin-2-ylmethyl-piperazin-1-yl)-benzyl]-oxazolidin-2-one

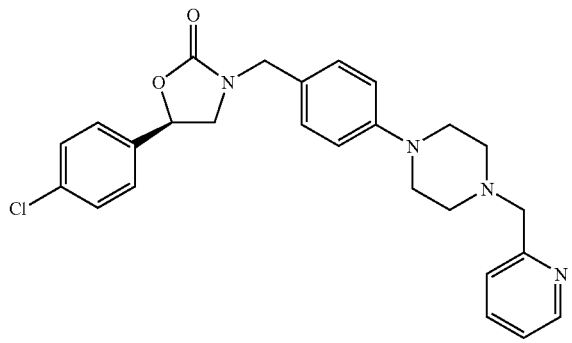

To a suspension of 5-(R)-(4-Chloro-phenyl)-3-(4-Iodo-benzyl)-oxazolidin-2-one (50 mg, 0.12 mmol), lead acetate (3 mg, 0.012 mmol), 2-(dicyclohexyl phosphino) biphenyl (5 mg, 0.014 mmol) and cesium carbonate (118 mg, 0.36 mmol) in toluene (2.5 mL), was added 2-pyridyl methyl piperazine and the reaction flask was heated at 100° C. for 3 h. The reaction mixture was diluted with dichloromethane (6 mL), washed with water (3 mL), brine (3 mL), dried over anhydrous sodium sulfate and concentrated in vacuo. The residue was purified by chromatography on silica gel, eluting with dichloromethane containing 0.5-2% ammonia (2 M) in methanol The title compound was isolated as an off white solid (30 mg, 54%). $^1$H NMR (300 MHz, CDCl$_3$): δ 8.6 (m, 1H), 7.69 (m, 1H), 7.44 (d, 1H), 7.35 (m, 2H), 7.25 (m, 5H), 6.88 (m, 2H), 5.42 (t, 1H), 4.45 (d, 1H), 4.33 (d, 1H), 3.75 (m, 3H), 3.24 (m, 5H), 2.69 (m, 4H).

Example 15

3-(4-Morpholin-4-yl-benzyl)-5-(R)-phenyl-oxazolidin-2-one

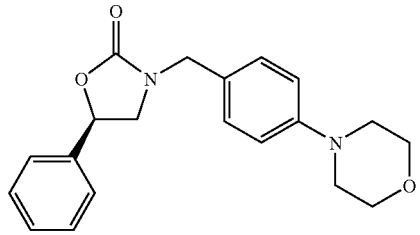

Palladium Acetate (3 mg, 0.013 mmol) and BINAP (8 mg, 0.013 mmol) were suspended in Toluene (2 mL) and stirred under argon for 10 minutes. The suspension was then added to a stirring suspension of 3-(4-Iodo-benzyl)-5-(R)-phenyl)-oxazolidin-2-one (50 mg, 0.132 mmol), morpholine (14 μL, 0.158 mmol), and cesium carbonate (43 mg, 0.396 mmol) in toluene (1 mL). Stirring continued for 5 minutes at room temperature and the mixture was then heated at 115° C. for 2 hours. The mixture was then cooled to room temperature, diluted with dichloromethane, filtered and concentrated in vacuo. The residue was purified by chromatography on silica gel, eluting with 30-40% ethyl acetate in hexanes. The title compound was isolated as a yellow solid (14 mg, 31%). $^1$H NMR (300 MHz, CDCl$_3$): δ 7.40-7.31 (m, 5H), 7.23 (d, 2H), 6.89 (d, 2H), 5.47 (t, 1H), 4.50-4.33 (q, 2H), 3.89-3.86 (m, 4H), 3.76 (t, 1H), 3.30 (t, 1H), 3.19-3.16 (m, 4H).

Example 16.1

3-[4-(4-Methyl-piperazin-1-yl)-benzyl]-5-(R)-phenyl-oxazolidin-2-one

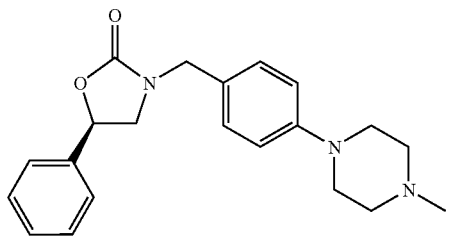

To a stirring suspension of palladium acetate (3 mg, 0.011 mmol), cesium carbonate (103 mg, 0.318 mmol), 3-(4-Iodo-benzyl)-5-(R)-phenyl)-oxazolidin-2-one (40 mg, 0.106 mmol), and Biphenyl-2-yl-dicyclohexyl-phosphane (4 mg, 0.011 mmol) in toluene was added 1-Methyl-piperazine (14 μL, 0.126 mmol). The mixture stirred at 100° C. for 3 hours and was then cooled to room temperature, diluted with water and extracted with ethyl acetate. The organics were washed with brine, dried over anhydrous sodium sulfate, filtered and concentrated in vacuo. The residue was purified by chromatography on silica gel, eluting with 30-40% ethyl acetate in hexanes. The title compound was isolated as a brown solid (14 mg, 38%). $^1$H NMR (300 MHz, CDCl$_3$): δ 7.40-7.30 (m, 5H), 7.21 (d, 2H), 6.91 (d, 2H), 5.46 (t, 1H), 4.50-4.31 (q, 2H), 3.76 (t, 1H), 3.30 (t, 1H), 3.27-3.21 (m, 4H), 2.61-2.58 (m, 4H), 2.37 (s, 3H).

The following compounds were made in a similar manner:

| | | | |
|---|---|---|---|
| 16.2 | 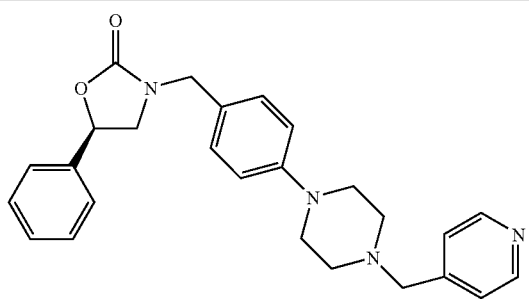 | 5-(R)-Phenyl-3-[4-(4-pyridin-4-ylmethyl-piperazin-1-yl)-benzyl]-oxazolidin-2-one | 32 mg, 38% brown oil |

NMR 8.58(d, 2H), 7.39-7.29(m, 7H), 7.20(d, 2H), 6.90(d, 2H), 5.46(t, 1H), 4.49(d, 1H), 4.36(d, 1H), 3.76(t, 1H), 3.58(s, 2H), 3.30(t, 1H), 3.27-3.21(m, 4H), 2.64-2.61(m, 4H)

| | | | |
|---|---|---|---|
| 16.3 | 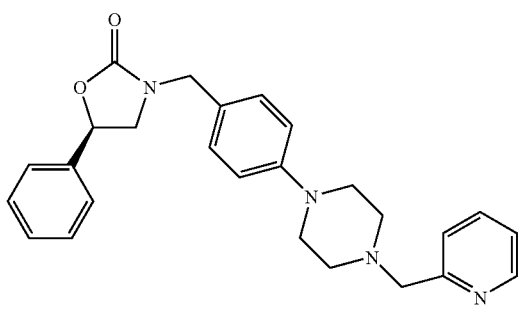 | 5-(R)-Phenyl-3-[4-(4-pyridin-2-ylmethyl-piperazin-1-yl)-benzyl]-oxazolidin-2-one | 41 mg, 48% brown oil |
| NMR | 8.60(d, 1H), 7.68(t, 1H), 7.45(d, 1H), 7.39-7.29(m, 5H), 7.28-7.17(m, 3H), 6.89(d, 2H), 5.46(t, 1H), 4.48(d, 1H), 4.34(d, 1H), 3.78-3.72(m, 3H), 3.31-3.23(m, 5H), 2.70-2.67(m, 4H) | | |
| 16.4 | 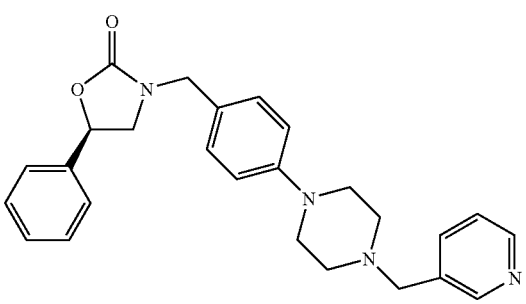 | 5-(R)-Phenyl-3-[4-(4-pyridin-3-ylmethyl-piperazin-1-yl)-benzyl]-oxazolidin-2-one | 39 mg, 46% yellow solid |
| NMR | 8.55(d, 2H), 7.72(d, 1H), 7.39-7.28(m, 6H), 7.19(d, 2H), 6.89(d, 2H), 5.46(t, 1H), 4.49(d, 1H), 4.35(d, 1H), 3.75(t, 1H), 3.59(s, 1H), 3.28(t, 1H), 3.26-3.19(m, 4H), 2.64-2.60(m, 4H) | | |
| 16.5 | 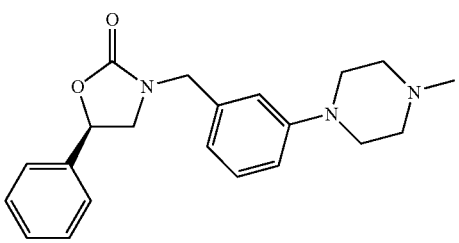 | 3-[3-(4-Methyl-iperazin-1-yl)-benzyl]-5-(R)-phenyl-oxazolidin-2-one | 21 mg, 30% brown oil |
| NMR | 7.39-7.32(m, 5H), 7.25(t, 1H), 6.85(d, 2H), 6.77(d, 1H), 5.49(t, 1H), 4.48(d, 1H), 4.34(d, 1H), 3.79(t, 1H), 3.33(t, 1H), 3.21-3.18(m, 4H), 2.59-2.56(m, 4H), 2.37(s, 3H) | | |
| 16.6 | 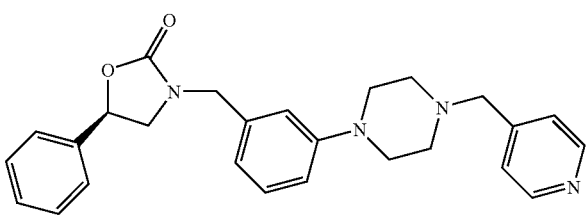 | 5-(R)-Phenyl-3-[3-(4-pyridin-4-ylmethyl-piperazin-1-yl)-benzyl]-oxazolidin-2-one | 24 mg, 29% brown oil |
| NMR | 8.58(d, 2H), 7.45-7.22(m, 8H), 6.84(d, 2H), 6.76(d, 1H), 5.49(t, 1H), 4.48(d, 1H), 4.34(d, 1H), 4.13(t, 1H), 3.33(t, 1H), 3.20-3.18(m, 4H), 2.63-2.60(m, 4H). | | |
| 16.7 | 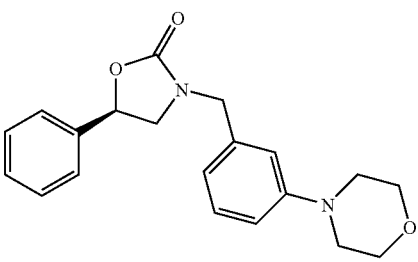 | 3-(3-Morpholin-4-yl-benzyl)-5-(R)-phenyl-oxazolidin-2-one | 25 mg, 37% brown oil |
| NMR | 7.40-7.33(m, 5H), 7.27(t, 1H), 6.85-6.80(m, 3H), 5.50(1, 1H), 4.49-4.40(dd, 2H), 3.88-3.78(m, 5H), 3.35(t, 1H), 3.16-3.12(m, 4H) | | |

-continued

| 16.8 | 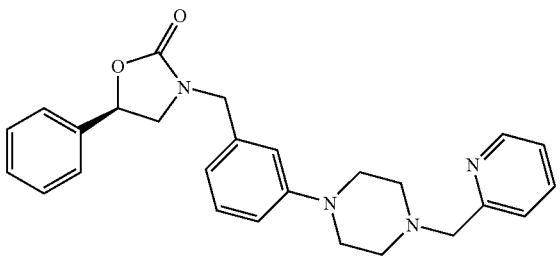 | 5-(R)-Phenyl-3-[4-(4-pyridin-2-lmethyl-piperazin-1-yl methyl)-benzyl]-oxazolidin-2-one | 45 mg, 49% yellow solid |
|---|---|---|---|
| NMR | 8.56(d, 1H), 7.65(t, 1H), 7.41-7.32(m, 8H), 7.29(d, 2H), 7.23(m, 1H), 5.48(t, 1H), 4.55(d, 1H), 4.39(d, 1H), 3.78(t, 1H), 3.68(s, 2H), 3.52(s, 2H), 3.31(t, 1H), 2.53(br s, 8H) | | |
| 16.9 | 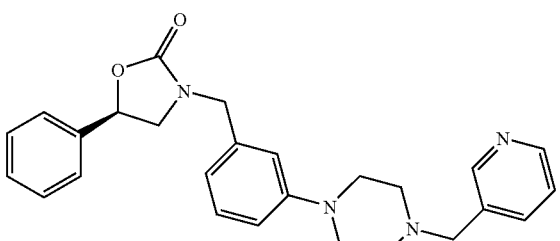 | 5-(R)-Phenyl-3-[4-(4-pyridin-3-ylmethyl-piperazin-1-ylmethyl)-benzyl]-oxazolidin-2-one | 49 mg, 53% yellow oil |
| NMR | 8.55-8.50(m, 2H), 7.65(d, 1H), 7.39-7.22(m, 10H), 5.48(t, 1H), 4.55,(d, 1H), 4.39 (d, 1H), 3.78(t, 1H), 3.53(d, 4H), 3.32(t, 1H), 2.34(br s, 8H). | | |

Example 17.1

5-(R)-Phenyl-3-[4-(4,4,5,5-tetramethyl-[1,3,2]dioxaborolan-2-yl)-benzyl]-oxazolidin-2-one

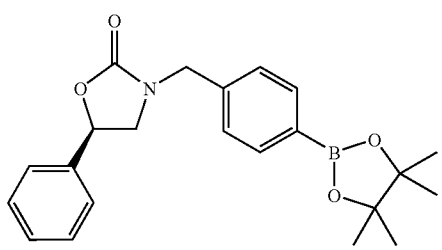

A flask containing 3-(4-Iodo-benzyl)-5-(R)-phenyl)-oxazolidin-2-one (390 mg, 1.03 mmol), 4,4,5,5,4',4',5',5'-Octamethyl-[2,2']bi[[1,3,2]dioxaborolanyl] (339 mg, 1.34 mmol), 1,1'-bis(diphenylphosphinoferrocene-dichloropalladium(II) (84 mg, 0.103 mmol), and potassium acetate (303 mg, 3.04 mmol) in DMF was heated at 110° C. for 2 hours. The mixture was then cooled to room temperature, diluted with water and extracted with ethyl acetate. The organics were washed with water (2×) and brine, dried over anhydrous sodium sulfate, filtered and concentrated in vacuo. The residue was purified by chromatography on silica gel, eluting with 30-50% ethyl acetate in hexanes. The title compound was isolated as a colourless solid (205 mg, 53%). $^1$H NMR. (300 MHz, CDCl$_3$): δ 7.81 (d, 2H), 7.39-7.29 (m, 7H), 5.47 (t, 1H), 4.52-4.48 (dd, 2H), 3.76 (t, 1H), 3.29 (t, 1H), 1.35 (12H).

The following compounds were made in a similar manner:

| 17.2 | 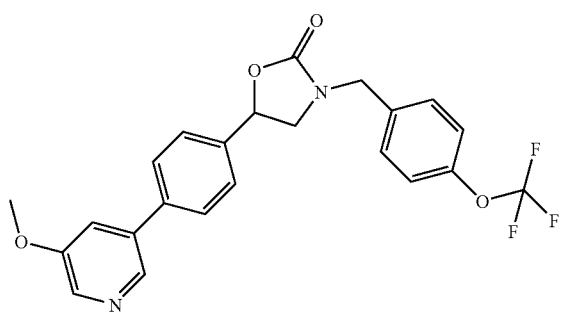 | 5-[4-(5-Methoxy-pyridin-3-yl)-phenyl]-3-(4-trifluoromethoxy-benzyl)-oxazolidin-2-one | 48 mg, 91% beige solid |
|---|---|---|---|
| NMR | 8.44(d, 1H), 8.33(d, 1H), 7.60(d, 2H), 7.43(d, 2H), 7.37-7.34(m, 3H), 7.24(d, 2H), 5.58(t, 1H), 4.59(d, 1H), 4.44(d, 1H), 3.93(s, 3H), 3.85(t, 1H), 3.37(t, 1H). | | |

| | | | |
|---|---|---|---|
| 17.3 | 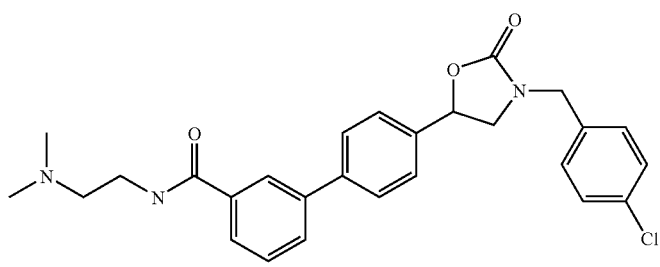 | 4'-[3-(4-Chloro-benzyl)-2-oxo-oxazolidin-5-yl]-biphenyl-3-carboxylic acid (2-dimethylamino-ethyl)-amide | 8 mg, 15% yellow oil |
| | NMR 8.05(s, 1H), 7.75-7.64(m, 5H), 7.53(t, 1H), 7.42-7.34(m, 4H), 7.26(d, 2H), 6.95(br s, 1H), 5.56(t, 1H), 4.55(d, 1H), 4.42(d, 1H), 3.82(t, 1H), 3.57(q, 2H), 3.36(t, 1H), 2.56(q, 2H), 2.30(s, 6H). | | |

Example 18

(3-S)-4-Iodo-N-(1-benzyl-3-pyrrolidinyl)benzamide

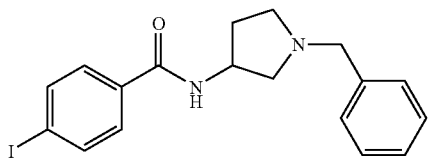

To a solution of 4-iodobenzoyl chloride (10 g, 37 mmol) in ether (400 mL) at 0° C. was added triethylamine (4.7 g, 45 mmol). (3-S)-1-Benzyl-3-aminopyrrolidine (7.3 g, 41 mmol) in ether (100 mL) was then added slowly via dropping funnel at 0° C. After the addition was complete, the mixture was further stirred for 18 hrs. Water (200 mL) was added and the mixture extracted with methylene chloride (3×200 mL) dried and concentrated to give the title compound (9.7 g, 64%) as beige powder. $^1$H NMR (CDCl3) δ: 7.79 (m, 2H), 7.47 (m, 2H), 7.26-7.35 (m, 5H), 6.51 (d, 1H, J=8.8 Hz), 4.62-4.68 (m, 1H), 3.63 (s, 2H), 2.91-2.96 (m, 1H), 2.70-2.74 (m, 1H), 2.58-2.63 (m, 1H), 2.25-2.44 (m, 2H), 1.68-1.77 (m, 1H).

Example 19.1

2-Amino-1-(4-bromo-phenyl)-ethanol

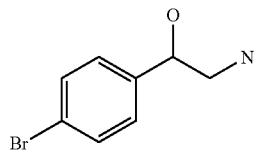

Sodium borohydride (227 mg, 6.00 mmol) was dissolved in methanol (10 mL) and 5% potassium hydroxide in methanol (4.49 mL, 4.00 mmol) was carefully added. To this solution was added 2-Amino-1-(4-bromo-phenyl)-ethanone hydrochloride (1.0 g, 4.00 mmol) dissolved in methanol (10 mL) and stirring continued for 0.2 hours at room temperature. The mixture was concentrated, and quenched with saturated sodium bicarbonate (10 mL) and extracted with dichloromethane several times. The organics were combined, dried over anhydrous sodium sulfate, filtered, and concentrated in vacuo. The title compound was isolated as a yellow solid (677 mg, 77%). $^1$H NMR (300 MHz, CDCl$_3$): 7.51-7.47 (d. 2H), 7.27-7.23 (d, 2H), 4.63-4.59 (m, 1H), 3.03 (dd, 1H), 2.76 (dd, 1H)

The following compound was made in a similar manner:

| | | | |
|---|---|---|---|
| 19.2 | | 2-Bromo-1-(3-bromo-phenyl)-ethanol | 4.72 g, 94% yellow oil |
| | 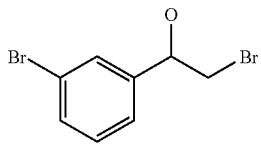 | | |
| | NMR 7.59(s, 1H), 7.50-7.47(m, 1H), 7.33-7.23(m, 2H), 4.95-4.90(m, 1H), 3.68-3.63(dd, 1H), 3.56-3.50(dd, 1H), 2.69(d. 1H). | | |

Example 20

[2-Bromo-1-(3-bromo-phenyl)-ethoxy]-trimethyl-silane

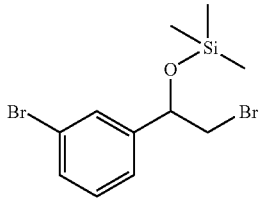

To a solution of 2-Bromo-1-(3-bromo-phenyl)-ethanol (4.72 g, 16.9 mmol), imidazole (5.75 g, 84.5 mmol) and dimethylaminopyridine (1.03 g, 8.45 mmol) in DMF at 0° C. was added Chloro-trimethyl-silane (4.56 mL, 3.90 mmol) dropwise. Stirring continued at 0° C. for 2 hours and was then warmed to RT. The mixture was diluted with saturated sodium bicarbonate and extracted with ethyl acetate. The organics were washed with water and brine, dried over anhydrous sodium sulfate, filtered and concentrated in vacuo. The title compound was isolated as a yellow oil (5.85 g, quantitative). $^1$H NMR (300 MHz, CDCl$_3$): 7.52 (s, 1H), 7.44 (d, 1H), 7.28-7.23 (m, 2H), 4.83 (t, 1H), 3.43 (d, 2H) 0.109 (s, 9H).

Example 21

2-Azido-1-(3-bromo-phenyl)-ethanol

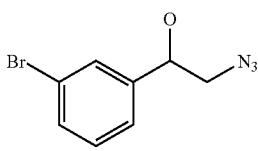

[2-Bromo-1-(3-bromo-phenyl)-ethoxy]-trimethyl-silane (5.85 g, 16.6 mmol and tetrabutyl sodium iodide (613 mg, 1.66 mmol) were dissolved in DMSO and sodium azide (2.16 g, 33.2 mmol) was slowly added. The mixture stirred at 80° C. for 4 hours and then at room temperature for 18 hours. The mixture was quenched with saturated sodium bicarbonate and extracted with ethyl acetate. The organics were washed with water brine and 1M HCl, then again with water and brine, dried over anhydrous sodium sulfate, filtered and concentrated in vacuo. The residue was purified by chromatography on silica gel, eluting with 5-10% ethyl acetate in hexanes. The title compound was isolated as a yellow oil (3.38 g, 83%). $^1$H NMR (300 MHz, CDCl$_3$): 7.57 (s, 1H), 7.48 (d, 1H), 7.31-7.29 (m, 2H), 4.87 (m, 1H), 3.49 (d, 2H), 2.45 (d, 1H).

Example 22

2-Amino-1-(3-bromo-phenyl)-ethanol

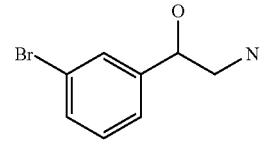

To a solution of 2-Azido-1-(3-bromo-phenyl)-ethanol (3.38 g, 13.8 mmol) in THF (40 mL) was added water (2.48 ml, 138 mmol) and triphenylphosphine (7.26 g, 27.7 mmol). The mixture stirred for 2 hours at 50° C. and was then cooled to room temperature, diluted with water and extracted with ethyl acetate. The organics were washed with 1M HCl (2×) and the aqueous washes were combined and neutralized with 1N sodium hydroxide. The aqueous mixture was extracted with ethyl acetate and the organics were washed with water and brine, dried over anhydrous sodium sulfate, filtered and concentrated in vacuo. The title compound was isolated as a yellow oil (2.53 g, 85%). $^1$H NMR (300 MHz, CDCl$_3$): 7.55 (s, 1H), 7.41 (d, 1H), 7.31-7.20 (m, 2H), 4.62 (m, 1H), 3.02 (d, 1H), 2.79 (m, 1H).

What is claimed is:

1. A compound according to Formula I:

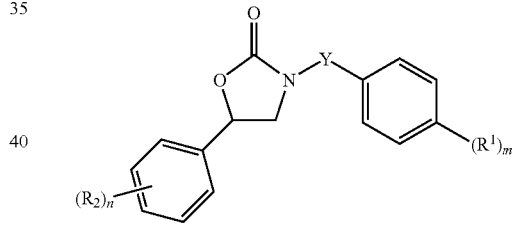

wherein:
$R^1$ is an optionally substituted phenyl group having one or more independently selected $R^6$ substituents;
$R^2$ is selected from the group consisting of H, F, Cl, Br, I, alkyl and alkylhalo substituents;
$R^6$ is independently selected from the group consisting of H, hydroxy, F, Cl, Br, I, nitro, CN, oxo, alkyl, alkylhalo, O-alkyl, O-alkylhalo, alkenyl, O-alkenyl, alkynyl, O-alkynyl, cycloalkyl, alkylene-cycloalkyl, O-cycloalkyl, O-alkyl-cycloalkyl, heterocycloalkyl, alkylene-heterocycloalkyl, O-heterocycloalkyl, O-alkylene-heterocycloalkyl, aryl, alkylenearyl, O-aryl, O-alkylenearyl, heteroaryl, alkyleneheteroaryl, O-heteroaryl, O-alkyleneheteroaryl, alkyleneOR$^4$, O-alkyleneOR$^4$, (CO)R$^3$, O(CO)R$^3$, alkyleneO(CO)R$^3$, alkylene(CO)R$^3$, O-alkylene(CO)R$^3$, CO$_2$R$^4$, alkyleneCO$_2$R$^3$, O-alkyleneCO$_2$R$^3$, alkylenecyano, O-alkylenecyano, NR$^4$R$^5$, alkyleneNR$^4$R$^5$, O-alkyleneNR$^4$R$^5$, (CO)NR$^4$R$^5$, alkylene(CO)NR$^4$R$^5$, O—(CO)NR$^4$R$^5$, O-alkylene(CO)NR$^4$R$^5$, NR$^4$(CO)R$^3$, alkyleneNR$^4$(CO)R$^3$, O-alkyleneNR$^4$(CO)R$^3$, NR$^4$(CO)NR$^4$R$^{13}$, alkyleneNR$^4$(CO)NR$^4$R$^5$, SR$^4$, alkyleneSR$^5$, O-alkyleneSR$^4$, (SO)R³, alkylene(SO)R³, O-alkylene(SO)R³, SO₂R³, alkyleneSO₂R³, O-alkyleneSO₂R³, (SO₂)NR⁴R⁵, alkylene(SO₂)NR⁴R⁵, O-alkylene(SO₂)NR⁷R⁸, NR⁷(SO₂)R⁸, alkyleneNR⁷(SO₂)R⁸, O-alkyleneNR⁴(SO₂)R⁵, NR⁴(SO₂)NR⁴R⁵, alkyleneNR⁴(SO₂)NR⁴R⁵, O-alkyleneNR⁴(SO₂)NR⁴R⁵, NR⁴(CO)OR⁵, alkylNR⁴(CO)OR⁵, O-alkylNR⁴(CO)OR⁵, SO₃R⁴ and any cyclic moiety may be further substituted with a substituent selected from the group consisting of alkyl, O-alkyl or haloalkyl;

R³ is independently selected from the group consisting of H, hydroxy, alkyl, alkylhalo, O-alkyl, O-alkylhalo, alkenyl, O-alkenyl, alkynyl, O-alkynyl, cycloalkyl, O-cycloalkyl, alkylenecycloalkyl, O-alkylene-cycloalkyl, heterocycloalkyl, O-heterocycloalkyl, alkyleneheterocycloalkyl, O-alkyleneheterocycloalkyl, aryl, O-aryl, alkylenearyl, O-alkylenearyl, heteroaryl, O-heteroaryl, alkyleneheteroaryl, O-alkyleneheteroaryl and any cyclic moiety may be further substituted with a substituent selected from the group consisting of alkyl, halo, haloalkyl O-alkyl, aryl, alkylenearyl, heteroaryl, alkyleneheteroaryl, and any cyclic moiety may be further substituted with a substituent selected from the group consisting of halo, alkyl, O-alkyl, haloalkyl, O-haloalkyl and NR⁴R⁵;

R⁴ and R⁵ are independently selected from the group consisting of H, alkyl, alkylhalo, alkenyl, alkynyl, cycloalkyl, alkylenecycloalkyl, heterocycloalkyl, alkyleneheterocycloalkyl, aryl, alkylenearyl, heteroaryl, and alkyleneheteroaryl, NR⁷R⁸, alkyleneNR⁷R⁸, OR⁷, alkyleneOR⁷, and any cyclic moiety may be further substituted with a substituent selected from the group consisting of alkyl, halo, haloalkyl O-alkyl, O-haloalkyl, aryl, alkylenearyl, heteroaryl, alkyleneheteroaryl; R⁷ and R⁸ are independently selected from the group consisting of H and alkyl;

Y is —CH₂—; and m is 1, and n is 0, 1, 2, 3 or 4;

or a pharmaceutically acceptable salt thereof.

2. A compound according to claim 1 wherein R² is H, Cl or F, or a pharmaceutically acceptable salt thereof.

3. A compound according to claim 2 wherein R² is Cl, or a pharmaceutically acceptable salt thereof.

4. A compound according to claim 1 selected from the group consisting of:

3-Biphenyl-4-ylmethyl-5-(R)-phenyl-oxazolidin-2-one;
4'-(2-Oxo-5-(R)-phenyl-oxazolidin-3-ylmethyl) biphenyl-3-carboxylic acid (2-dimethylamino-ethyl)-amide;
3-[4'-(4-Methyl-piperazine-1-carbonyl)-biphenyl-4-ylmethyl]-5-(R)-phenyl-oxazolidin-2-one;
3-[3'-(4-Methyl-piperazine-1-carbonyl)-biphenyl-4-ylmethyl]-5-(R)-phenyl-oxazolidin-2-one;
4'-(2-Oxo-5-(R)-phenyl-oxazolidin-3-ylmethyl) biphenyl-4-carboxylic acid (2-dimethylamino-ethyl)-amide;
4'-[5-(4-Fluorophenyl)-2-oxo-oxazolidin-3-yl methyl]-biphenyl-3-carboxylic acid (2-dimethylamino-ethyl)-amide;
5-(4-Fluorophenyl)-3-(2'-morpholin-4-ylmethyl-biphenyl-4-ylmethyl)-oxazolidin-2-one;
4'-[5-(4-Fluorophenyl)-2-oxo-oxazolidin-3-yl methyl]-biphenyl-3-carboxylic acid;
5-(4-Fluorophenyl)-3-[3'-(4-methyl-piperazine-1-carbonyl)-biphenyl-4-ylmethyl]-oxazolidin-2-one;
3-(4'-Dimethylamino methyl-biphenyl-4-ylmethyl)-5-(4-fluorophenyl)-oxazolidin-2-one;
4'-[5-(4-Fluorophenyl)-2-oxo-oxazolidin-3-yl methyl]-biphenyl-3-carboxylic acid (2-dimethylamino-ethyl)-methyl-amide;
4'-[5-(4-Fluorophenyl)-2-oxo-oxazolidin-3-yl methyl]-biphenyl-3-carboxylic acid (2-hydroxyethyl)-amide;
4'-[5-(4-Fluorophenyl)-2-oxo-oxazolidin-3-yl methyl]-biphenyl-3-carboxylic acid ethylamine;
4'-[5-(R)-(4-Chlorophenyl)-2-oxo-oxazolidin-3-yl methyl]-biphenyl-3-carboxylic acid (2-dimethylamino-ethyl)-amide;
3'-(2-oxo-5-(R)-phenyl-oxazolidin-3-ylmethyl)-biphenyl-3-carboxylic acid (2-dimethylamino-ethyl)-amide;
4'-(2-oxo-5-(R)-phenyl-oxazolidin-3-ylmethyl)-biphenyl-4-carboxylic acid (1-benzyl-pyrrolidin-3-(S)-yl)-amide;
4'-[5-(S)-(4-Fluorophenyl)-2-oxo-oxazolidin-3-yl methyl]-biphenyl-3-carboxylic acid (2-dimethylamino-ethyl)-methyl-amide;
4'-[5-(R)-(4-Fluorophenyl)-2-oxo-oxazolidin-3-yl methyl]-biphenyl-3-carboxylic acid (2-dimethylamino-ethyl)-methyl-amide;
5-(R)-(4-Chlorophenyl)-3-(2'-morpholin-4-ylmethyl-biphenyl-4-ylmethyl)-oxazolidin-2-one;
4'-[5-(R)-(4-Chlorophenyl)-2-oxo-oxazolidin-3-yl methyl]-biphenyl-3-carboxylic acid (2-dimethylamino-ethyl)-methyl-amide;
3-[4'-(4-Methyl-piperazin-1-ylmethyl)-biphenyl-4-yl methyl]-5-phenyl-oxazolidin-2-one;
5-(4-Fluorophenyl)-3-[3'-(4-methyl-piperazin-1-ylmethyl)-biphenyl-4-ylmethyl]-oxazolidin-2-one;
5-(4-Fluorophenyl)-3-(3'-morpholin-4-yl methyl-biphenyl-4-ylmethyl)-oxazolidin-2-one;
5-(4-Fluorophenyl)-3-(3'-piperazin-1-ylmethyl)-biphenyl-4-ylmethyl)-oxazolidin-2-one;
5-(R)-(4-Chlorophenyl)-3-(3'-diethylaminomethyl-biphenyl-4-ylmethyl)-oxazolidin-2-one;
5-(R)-(4-Chlorophenyl)-3-(3'-{[dimethylaminoethyl)-methylamino]-methyl} biphenyl-4-ylmethyl)-oxazolidin-2-one;
5-(R)-(4-Chlorophenyl)-3-(3'-piperidin-1-yl methyl-biphenyl-4-ylmethyl)-oxazolidin-2-one;
5-(R)-(4-Chlorophenyl)-3-(3'-morpholin-4-yl methyl-biphenyl-4-ylmethyl)-oxazolidin-2-one;
5-(R)-(4-Chlorophenyl)-3-[3'-(4-methyl-piperazin-1-yl-methyl)-biphenyl-4-ylmethyl]-oxazolidin-2-one;
5-(R)-(4-Chlorophenyl)-3-(3'-dimethylaminomethyl-biphenyl-4-ylmethyl)-oxazolidin-2-one;
5-(R)-(4-Chlorophenyl)-3-(3'-piperazin-1-ylmethyl)-biphenyl-4-ylmethyl)-oxazolidin-2-one;
5-(R)-(4-Chlorophenyl)-3-(2'-dimethylaminomethyl-biphenyl-4-ylmethyl)-oxazolidin-2-one;
5-(R)-(4-Chlorophenyl)-3-(2'-{[(2-dimethylaminoethyl)-methyl-amino]-methyl}-biphenyl-4-yl methyl)-oxazolidin-2-one;
5-(R)-(4-Chlorophenyl)-3-(2'-(4-methyl-piperazin-1-yl methyl)-biphenyl-4-ylmethyl)-oxazolidin-2-one;
5-(R)-(4-Chlorophenyl)-3-[2'-(3-(S)-dimethylamino-pyrrolidin-1-yl methyl)-1-biphenyl-4-ylmethyl]-oxazolidin-2-one;
5-(R)-(4-Chlorophenyl)-3-(2'-piperidin-1-yl methyl-biphenyl-4-ylmethyl)-oxazolidin-2-one;
5-(R)-(4-Chlorophenyl)-3-[2'-(3-(R)-dimethylamino-pyrrolidin-1-yl methyl)-1-biphenyl-4-ylmethyl]-oxazolidin-2-one;
5-(R)-(4-Chlorophenyl)-3-(2'-piperazin-1-yl methyl-biphenyl-4-ylmethyl)-oxazolidin-2-one;

5-(R)-(4-Chlorophenyl)-3-(4'-dimethylaminomethyl-biphenyl-4-ylmethyl)-oxazolidin-2-one;

5-(R)-(4-Chlorophenyl)-3-(4'-{[(2-dimethylamino ethyl)-methyl-amino]-methyl}-biphenyl-4-yl methyl)-oxazolidin-2-one;

5-(R)-(4-Chlorophenyl)-3-(4'-morpholin-4-yl methyl-biphenyl-4-ylmethyl)-oxazolidin-2-one;

5-(R)-(4-Chlorophenyl)-3-(4'-piperidin-1-yl methyl-biphenyl-4-ylmethyl)-oxazolidin-2-one;

5-(R)-(4-Chlorophenyl)-3-[4'-(4-methyl-piperazin-1-yl methyl)-biphenyl-4-ylmethyl)-oxazolidin-2-one;

5-(R)-(4-Chlorophenyl)-3-(4'-piperazin-1-yl methyl-biphenyl-4-ylmethyl)-oxazolidin-2-one, and 5-(4-Fluorophenyl)-3-(3'-hydroxymethyl-biphenyl-4-yl-methyl)-oxazolidin-2-one or a pharmaceutically acceptable salt of any foregoing compound.

5. A pharmaceutical composition comprising a compound or a pharmaceutically acceptable salt thereof according to claim 1 and a pharmaceutically acceptable carrier or excipient.

6. A pharmaceutical composition comprising a compound or a pharmaceutically acceptable salt thereof according to claim 4 and a pharmaceutically acceptable carrier or excipient.

* * * * *